United States Patent
Long et al.

(10) Patent No.: US 10,653,144 B2
(45) Date of Patent: May 19, 2020

(54) PESTICIDAL AND PARASITICIDAL VINYL ISOXAZOLINE COMPOUNDS

(71) Applicant: BOEHRINGER INGELHEIM ANIMAL HEALTH USA INC., Duluth, GA (US)

(72) Inventors: Alan Long, Flowery Branch, GA (US); Loic Patrick Le Hir de Fallois, Atlanta, GA (US)

(73) Assignee: BOEHRINGER INGELHEIM ANIMAL HEALTH USA INC., Duluth, GA (US)

(*) Notice: Subject to any disclaimer, the term of this patent is extended or adjusted under 35 U.S.C. 154(b) by 0 days.

(21) Appl. No.: 16/340,795

(22) PCT Filed: Oct. 11, 2017

(86) PCT No.: PCT/US2017/056130
§ 371 (c)(1),
(2) Date: Apr. 10, 2019

(87) PCT Pub. No.: WO2018/071535
PCT Pub. Date: Apr. 19, 2018

(65) Prior Publication Data
US 2019/0281829 A1 Sep. 19, 2019

Related U.S. Application Data

(60) Provisional application No. 62/408,221, filed on Oct. 14, 2016.

(51) Int. Cl.
| | |
|---|---|
| A01N 43/80 | (2006.01) |
| A61P 33/14 | (2006.01) |
| A01N 43/90 | (2006.01) |
| C07D 261/04 | (2006.01) |
| C07D 471/04 | (2006.01) |
| A61P 33/00 | (2006.01) |

(52) U.S. Cl.
CPC ............ *A01N 43/80* (2013.01); *A01N 43/90* (2013.01); *A61P 33/00* (2018.01); *A61P 33/14* (2018.01); *C07D 261/04* (2013.01); *C07D 471/04* (2013.01); *C07B 2200/07* (2013.01)

(58) Field of Classification Search
None
See application file for complete search history.

(56) References Cited

FOREIGN PATENT DOCUMENTS

| | | |
|---|---|---|
| CN | 102911131 B | 10/2014 |
| EP | 2186804 A1 | 5/2010 |
| JP | 2007016017 A | 1/2007 |
| WO | 2007/070606 A2 | 6/2007 |
| WO | WO-2008137139 A1 * | 11/2008 ........... C07D 413/10 |
| WO | 2010025998 A1 | 3/2010 |
| WO | 2010070068 A2 | 6/2010 |
| WO | 2016/155831 A1 | 10/2016 |
| WO | WO-2016155831 A1 * | 10/2016 ............ A01N 43/80 |

OTHER PUBLICATIONS

Written Opinion of the International Searching Authority for PCT/US2017/056130 dated Nov. 11, 2017.*

* cited by examiner

*Primary Examiner* — Zinna Northington Davis
(74) *Attorney, Agent, or Firm* — Judy Jarecki-Black; John Ezcurra

(57) ABSTRACT

The present invention relates to pesticidal and parasiticidal isoxazoline of formula (I) and salts thereof:

(I)

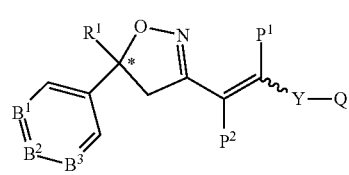

wherein variables $B^1$, $B^2$, $B^3$, $R^1$, $P^1$, $P^2$, Y and Q are described herein are as defined in the description. The invention also relates to parasiticidal and pesticidal compositions comprising the isoxazoline compounds of formula (I), processes for their preparation and their uses to prevent or treat parasitic infections or infestations in animals and as pesticides.

22 Claims, No Drawings

PESTICIDAL AND PARASITICIDAL VINYL ISOXAZOLINE COMPOUNDS

CROSS REFERENCE TO RELATED APPLICATIONS

This application claims the benefit of priority to U.S. Provisional Application No. 62/408,221, filed Oct. 14, 2016, which is incorporated herein by reference.

FIELD OF THE INVENTION

The present invention relates to novel and inventive pesticidal and parasiticidal isoxazoline compounds of formula (I):

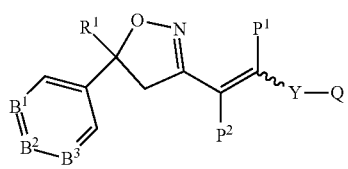

wherein, $B^1$, $B^2$, $B^3$, $R^1$, $P^1$, $P^2$, Y and Q are as defined below, and compositions comprising at least one compound of formula (I) in combination with a pharmaceutically acceptable or agriculturally acceptable carrier. The invention also relates to uses of the compounds and methods comprising the compounds for the treatment and prevention of parasitic infections or infestations in or on animals and for controlling pests in crops, plants, plant propagation material and material derived from wood.

BACKGROUND OF THE INVENTION

Animals such as mammals and birds are often susceptible to parasite infestations/infections. These parasites may be ectoparasites, such as insects, and endoparasites such as nematodes and other worms. Domesticated animals, such as cats and dogs, are often infested with one or more of the following ectoparasites:
- fleas (e.g. *Ctenocephalides* spp., such as *Ctenocephalides felis* and the like);
- ticks (e.g. *Rhipicephalus* spp., *Ixodes* spp., *Dermacentor* spp., *Amblyomma* spp., and the like);
- mites (e.g. *Demodex* spp., *Sarcoptes* spp., *Otodectes* spp., and the like);
- lice (e.g. *Trichodectes* spp., *Cheyletiella* spp., *Linognathus* spp. and the like);
- mosquitoes (*Aedes* spp., *Culex* spp., *Anopheles* spp. and the like); and
- flies (*Haematobia* spp., *Musca* spp., *Stomoxys* spp., *Dermatobia* spp., *Cochliomyia* spp. and the like).

Fleas are a particular problem because not only do they adversely affect the health of the animal or human, but they also cause a great deal of psychological stress. Moreover, fleas may also transmit pathogenic agents to animals and humans, such as tapeworm (*Dipylidium caninum*).

Similarly, ticks are also harmful to the physical and psychological health of the animal or human. However, the most serious problem associated with ticks is that they are vectors of pathogenic agents in both humans and animals. Major diseases which may be transmitted by ticks include borreliosis (Lyme disease caused by *Borrelia burgdorferi*), babesiosis (or piroplasmosis caused by *Babesia* spp.) and rickettsioses (e.g. Rocky Mountain spotted fever). Ticks also release toxins which cause inflammation or paralysis in the host. Occasionally, these toxins are fatal to the host.

Likewise, farm animals are also susceptible to parasite infestations. For example, a parasite which is prevalent among cattle in some regions are ticks of the genus *Rhipicephalus*, especially those of the species *microplus* (cattle tick), *decoloratus* and *annulatus*. Ticks such as *Rhipicephalus microplus* (formerly *Boophilus microplus*) are difficult to control because they lay eggs in the pasture where farm animals graze. This species of ticks is considered a one-host tick and spends immature and adult stages on one animal before the female engorges and falls off the host to lay eggs in the environment. In addition to cattle, *Rhipicephalus microplus* may infest buffalo, horses, donkeys, goats, sheep, deer, pigs, and dogs. A heavy tick burden on animals can decrease production and damage hides as well as transmit diseases such as babesiosis ("cattle fever") and anaplasmosis.

Invertebrate pests also destroy growing and harvested crops and attack wooden dwellings and commercial structures, causing large economic loss to the food supply and to property. While a large number of pesticidal agents are known, due to the ability of target pests to develop resistance to said agents, there is an ongoing need for new agents for combating animal pests. In particular, pests such as insects and acaridae are difficult to be effectively controlled. However, it is a continuing objective to provide further pesticidal compounds which, at least in some aspects, offer advantages over the known compounds.

Various patent publications have described isoxazoline compounds having pesticidal properties. Recently, isoxazole and isoxazoline-containing compounds have been demonstrated to be effective against parasites that harm animals. For example, U.S. Pat. No. 7,964,204 (to DuPont, incorporated by reference herein in its entirety) discloses isoxazoline compounds according to Formula (I) below, which are active against ectoparasites and/or endoparasites.

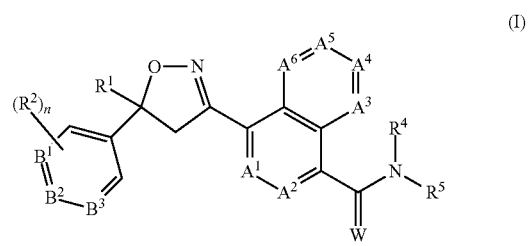

In addition, published patent application nos. US 2010/0254960 A1, WO 2007/070606 A2, WO 2007/123855 A2, WO 2010/003923 A1, U.S. Pat. No. 7,951,828 & U.S. Pat. No. 7,662,972, US 2010/0137372 A1, US 2010/0179194 A2, US 2011/0086886 A2, US 2011/0059988 A1, US 2010/0179195 A1 and WO 2007/075459 A2 and U.S. Pat. Nos. 7,951,828 and 7,662,972 describe various other parasiticidal isoxazoline compounds. Other published patent applications that describe various other parasiticidal isoxazoline compounds and formulations comprising the same include WO 2007/079162 A1, WO 2008/154528 A1, WO 2009/002809 A2, WO 2011/149749 A1, WO 2014/439475 A1, U.S. Pat. No. 8,466,115, WO 2012/120399, WO 2014/039484, WO 2014/189837, (Zoetis) and WO2012 120135A1 (Novartis). WO 2012/089623 describes topical localized isoxazoline formulations comprising glycofurol. WO 2013/039948 A1 provides for topical veterinary compositions comprising at least one isoxazoline active agent and WO 2013/119442 A1 provides for oral veterinary compositions such as a soft chew, which comprise at least one isoxazoline active agent.

More recently, WO 2016/155831 A1 described compounds of formula (I) below, which are described to have pesticidal properties.

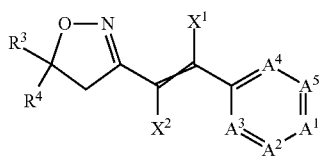

Although the publication describes in general terms that the compounds may be useful for controlling invertebrate parasites that infest animals, only examples that demonstrate that the compounds are effective against pests that infest plants and crops are included. The publication does not include any examples that demonstrate that the compounds are effective against external parasites (e.g. fleas and ticks) or internal parasites (e.g. nematodes and filarial worms) that infest and infect animals.

Although some of these publications describe compounds containing a substituted isoxazoline ring having pesticidal and parasiticidal properties, none of the foregoing publications describe compounds of formula (I), that possess parasiticidal and pesticidal activity, particularly for controlling endoparasites or ectoparasites in or on animals.

The foregoing documents and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. Citation or identification of any document in this application is not an admission that such document is available as prior art to the present invention.

SUMMARY OF THE INVENTION

The present invention provides novel and inventive isoxazoline compounds of formula (I), shown below that are biologically active against parasites that harm animals and against pests that damage crops, plants, plant propagation material and material derived from wood. Accordingly, the application provides parasiticidal and pesticidal isoxazoline compounds and compositions comprising the isoxazoline compounds in combination with a pharmaceutically acceptable carrier or an agriculturally acceptable carrier. The present invention also provides methods for the treatment and/or prevention of a parasitic infection or infestation in an animal and for controlling pests that harm plants, plant propagation material and material derived from wood, which comprise administering an effective amount of a compound of the invention to the animal or to the plants, plant propagation material, the soil in which the infected plant grows, or the wood-derived material, with a pesticidally effective amount of a compound of formula (I).

A first object of the invention is to provide parasiticidal and pesticidal novel and inventive isoxazoline compounds of formula (I):

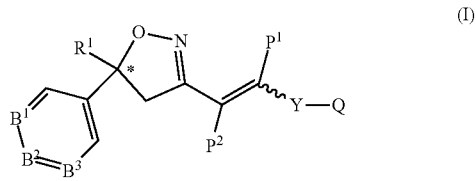

wherein:

the asterisk (*) signifies a quaternary chiral center;

the squiggly bond ( ~~~ ) signifies that the double bond may be in the E- or Z-configuration;

$B^1$, $B^2$ and $B^3$ are each independently C—R or N;

each R is independently H, halogen, cyano, —$NO_2$, alkyl, haloalkyl, alkoxy, haloalkoxy, alkylthio, haloalkylthio, alkylsulfinyl, haloalkylsulfinyl, alkylsulfonyl, haloalkylsulfonyl, —$SF_5$, —C(=S)—$NH_2$, alkylamino, dialkylamino or alkoxycarbonyl;

$R^1$ is $C_1$-$C_3$alkyl or $C_1$-$C_3$haloalkyl;

$P^1$ and $P^2$ are independently hydrogen, halogen, cyano, nitro, alkyl, haloalkyl, alkenyl, haloalkenyl, alkynyl, haloalkynyl, cycloalkyl, alkoxy, haloalkoxy, alkylthio, haloalkylthio, alkylsulfinyl, haloalkylsulfinyl, alkylsulfonyl or haloalkylsulfonyl;

Y is an optionally substituted phenylene, naphthylene, indanylene, a 5- or 6-membered heteroarylene or an 8-10-membered fused heterobicylylene, wherein the optional substituents are selected from the group consisting of halogen, alkyl, haloalkyl, cycloalkyl, halocycloalkyl, alkoxy, haloalkoxy, alkylthio, haloalkylthio, alkylsulfinyl, haloalkylsulfinyl, alkylsulfonyl, haloalkylsulfonyl, alkylamino, dialkylamino, alkylcarbonyl, haloalkylcarbonyl, alkoxycarbonyl, haloalkoxycarbonyl, —$SF_5$, —CN, —$NO_2$ and —C(=S)—$NH_2$;

Q is X—$NR^2R^3$, the group (—$CH_2$—)(—$CH_2$—)N—$R^3$, which for avoidance of doubt represents the following structure herein:

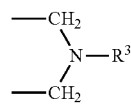

wherein each methylene group is bonded to a tetravalent atom of Y to form a spirocyclic group, OH, $NH_2$, alkoxy, haloalkoxy, alkylamino, haloalkylamino, dialkylamino, dihaloalkylamino, thiol, alkylthio, haloalkylthio, alkylsulfinyl, haloalkylsulfinyl, alkylsulfonyl, haloalkylsulfonyl, —$SF_5$, —C(=S)—$NH_2$, or an optionally substituted 5- or 6-membered carbocyclyl, heterocyclyl, heteroaryl ring, wherein the optional substituents of said carbocyclyl, heterocyclyl or heteroaryl ring are selected from halogen, alkyl, haloalkyl, alkoxy, haloalkoxy, alkylthio, haloalkylthio, alkylsulfinyl, haloalkylsulfinyl, alkylsulfonyl, haloalkylsulfonyl, alkylamino, dialkylamino, alkylcarbonyl, haloalkylcarbonyl, alkoxycarbonyl, haloalkoxycarbonyl, —$SF_5$, —CN or —$NO_2$ and —C(=S)—$NH_2$;

or the groups T1 or T2:

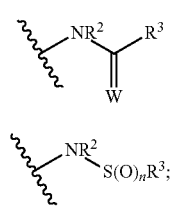

W is O or S;

X is $(CH_2)_n$, $CH(CH_3)$, $CH(CN)$, $C(=O)$ or $C(=S)$;

$R^2$ is H, alkyl, alkenyl, alkynyl, cycloalkyl, alkylcycloalkyl, cycloalkylalkyl, alkylcarbonyl or alkoxycarbonyl;

$R^3$ is H, $OR^7$, $NR^8R^9$ or $Q^1$; or alkyl, haloalkyl, alkenyl, haloalkenyl, alkynyl, cycloalkyl, alkylcycloalkyl, cycloalkylalkyl, alkylcarbonyl, alkoxycarbonyl, aminocarbonyl, alkylaminocarbonyl or dialkylaminocarbonyl, each optionally substituted with one or more substituents independently selected from $R^4$; or when Q is $X$—$NR^2R^3$, $R^2$ and $R^3$ taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of alkyl, haloalkyl, halogen, —CN, —$NO_2$ alkoxy and halolakoxy;

each $R^4$ is independently halogen; alkyl, cycloalkyl, alkoxy, haloalkoxy, alkylthio, haloalkylthio, alkylsulfinyl, haloalkylsulfinyl, alkylsulfonyl, haloalkylsulfonyl, alkylamino, haloalkylamino, dialkylamino, dihaloalkylamino, cycloalkylamino, alkylcarbonyl, alkoxycarbonyl, alkylaminocarbonyl, dialkylaminocarbonyl, haloalkylcarbonyl, haloalkoxycarbonyl, haloalkylaminocarbonyl, dihaloalkylaminocarbonyl, hydroxy, —$SF_5$, —$C(=S)NH_2$, —$NH_2$, —CN or —$NO_2$; or $Q^2$;

each $R^5$ is independently halogen, alkoxy, haloalkoxy, alkylthio, haloalkylthio, alkylsulfinyl, haloalkylsulfinyl, alkylsulfonyl, haloalkylsulfonyl, alkylamino, dialkylamino, alkoxycarbonyl, —$SF_5$, —$C(=S)NH_2$, —CN or —$NO_2$;

each $R^6$ is independently halogen, alkyl, haloalkyl, cycloalkyl, halocycloalkyl, alkoxy, haloalkoxy, alkylthio, haloalkylthio, alkylsulfinyl, haloalkylsulfinyl, alkylsulfonyl, haloalkylsulfonyl, alkylamino, dialkylamino, —$SF_5$, —$C(=S)NH_2$, —CN, —$NO_2$, phenyl or pyridinyl;

$R^7$ is H; or alkyl, alkenyl, alkynyl, cycloalkyl, alkylcycloalkyl or cycloalkylalkyl, each optionally substituted with one of more halogen;

$R^8$ is H, alkyl, alkenyl, alkynyl, cycloalkyl, alkylcycloalkyl, cycloalkylalkyl, alkylcarbonyl or alkoxycarbonyl;

$R^9$ is H; $Q^3$; or alkyl, alkenyl, alkynyl, cycloalkyl, alkylcycloalkyl or cycloalkylalkyl, each optionally substituted with one or more substituents independently selected from $R^4$; or $R^8$ and $R^9$ taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of alkyl, haloalkyl, halogen, —CN, —$NO_2$ haloalkoxy and alkoxy;

$Q^1$ is a phenyl ring, a 5- or 6-membered heterocyclic ring, or an 8-, 9- or 10-membered fused bicyclic ring system optionally containing one to three heteroatoms selected from up to 1 O, up to 1 S and up to 3 N, each ring or ring system optionally substituted with one or more substituents independently selected from $R^5$;

$Q^2$ is independently a phenyl ring or a 5- or 6-membered heterocyclic ring, each ring optionally substituted with one or more substituents independently selected from $R^6$;

$Q^3$ is a phenyl ring or a 5- or 6-membered heterocyclic ring, each ring optionally substituted with one or more substituents independently selected from $R^6$; and n is 0, 1 or 2.

Further, this invention provides for antiparasitic compositions for the treatment or prevention of parasitic infections and/or infestations in animals comprising a parasiticidally effective amount of at least one compound of formula (I), in combination with a pharmaceutically acceptable carrier. The compositions may be formulated for oral, subcutaneous, parenteral, sublingual or buccal delivery and topical administration including spot-on and pour-on administration.

Another object of the invention is to provide pesticidal compositions comprising at least one compound of formula (I), for combating pests that are harmful to plants, plant propagation material or material derived from wood in combination with a pesticidally effective carrier.

Another object of the invention is to provide veterinary and agricultural compositions comprising at least one compound of formula (I) for combating pests and parasites comprising a pesticidally or parasiticidally effective amount of the compounds of the invention, or veterinarily or agriculturally acceptable salts thereof, in combination with one or more other active agent and a veterinarily or agriculturally acceptable carrier or diluent.

Another object of the invention is to provide plant propagation material (e.g. seed), comprising at least one compound of formula (I) or agriculturally acceptable salts thereof, and plant propagation material that has been treated with at least one compound of formula (I) or a composition comprising the compound.

Another object of this invention is to provide methods of treatment and/or prevention of parasitic infections or infestations in or on an animal, which comprise treating the infected or infested animal with a parasiticidally effective amount of a compound of formula (I).

Another object of this invention is to provide methods for combating pests on crops, plants, plant propagation material or material derived from wood, which comprises treating the infected plant, or the soil in which the infected plant grows, or the wood-derived material with a pesticidally effective amount of a compound of formula (I).

Another object of the invention is to provide methods for combating or controlling pests at a locus (excluding an animal), comprising administering a pesticidally or parasiticidally effective amount of a compound of formula (I), or veterinarily or agriculturally acceptable salts thereof, to the locus.

Another object of the invention is to provide a compound of formula (I) for use in the treatment and/or prevention of a parasitic infection or infestation in or on an animal. Still another object of the invention is use of a compound of formula (I), in the preparation of a medicament for the treatment and/or prevention of a parasitic infestation or infection in or on an animal.

Still another object of this invention is to provide processes for the preparation of isoxazoline compounds of formula (I).

The present invention does not intend to encompass within the scope of the invention any previously disclosed compound, product, process of making the product or method of using the product, which meets the written description and enablement requirements of the USPTO (35 U.S.C. 112, first paragraph) or the EPO (Article 83 of the EPC), such that the applicant(s) reserve the right and hereby disclose a disclaimer of any previously described product, method of making the product or process of using the product. It is therefore an intention of the invention to not explicitly cover compounds, products, processes of making products or compounds, or methods of using products or compounds that are explicitly disclosed in the prior art or whose novelty is destroyed by prior art, including without limitation any prior art herein mentioned; and the applicant(s) explicitly reserve the right to introduce into any claim a disclaimer as to any previously disclosed compound, product, process of making the product or method of using the product. Specifically, the compounds of the invention are not intended to encompass isoxazoline compounds that have been previously disclosed in the art.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law; e.g., they allow for elements not explicitly recited, but exclude elements that are found in the prior art or that affect a basic or novel characteristic of the invention. These and other embodiments are disclosed or are obvious from and encompassed by, the following Detailed Description.

DETAILED DESCRIPTION OF THE INVENTION

The novel and inventive isoxazoline compounds of formula (I) are active against pests, including parasites that cause harm to animals, and pests that damage plants, plant propagation material and material containing wood or derived from wood. Accordingly, the compounds of the invention are useful for preventing and/or treating a parasitic infestation/infection in an animal and for controlling and eradicating pests that damage plants, plant propagation material and material derived from wood.

The present invention provides novel and inventive isoxazoline compounds and compositions comprising the compounds. Furthermore, the invention provides methods for preventing and/or treating a parasitic infestation or infection in an animal, and the use of the compounds for treating a parasitic infestation or infection in an animal or the use of the compounds in the manufacture of a medicament for treating a parasitic infestation or infection in an animal.

In one embodiment, the invention provides novel and inventive isoxazoline compounds that are effective against ectoparasites that harm animals. Thus, the compounds described herein may be used to treat and prevent parasitic infestations in or on animals.

In another embodiment, the present invention provides uses of the compounds of formula (I) for controlling and eradicating pests that cause damage to plants, plant propagation material and material derived from wood. In still another embodiment, the present invention provides uses of the isoxazoline compounds of formula (I) to control environmental pests at a locus.

A first object of the invention is to provide novel and inventive parasiticidal and pesticidal isoxazoline compounds of formula (I):

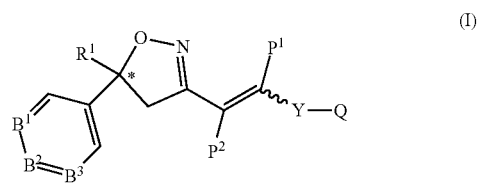

wherein:
the asterisk (*) signifies a quaternary chiral center;
the squiggly bond ($\sim$) signifies that the double bond may be in the E- or Z-configuration;
$B^1$, $B^2$ and $B^3$ are each independently C—R or N;
each R is independently H, halogen, cyano, —$NO_2$, alkyl, haloalkyl, alkoxy, haloalkoxy, alkylthio, haloalkylthio, alkylsulfinyl, haloalkylsulfinyl, alkylsulfonyl, haloalkylsulfonyl, —$SF_5$, —C(=S)—$NH_2$, alkylamino, dialkylamino or alkoxycarbonyl;
$R^1$ is $C_1$-$C_3$alkyl or $C_1$-$C_3$haloalkyl;
$P^1$ and $P^2$ are independently hydrogen, halogen, cyano, nitro, alkyl, haloalkyl, alkenyl, haloalkenyl, alkynyl, haloalkynyl, cycloalkyl, alkoxy, haloalkoxy, alkylthio, haloalkylthio, alkylsulfinyl, haloalkylsulfinyl, alkylsulfonyl or haloalkylsulfonyl;
Y is an optionally substituted phenylene, naphthylene, indanylene, a 5- or 6-membered heteroarylene or an 8-10-membered fused heterobicyclylene, wherein the optional substituents are selected from the group consisting of halogen, alkyl, haloalkyl, cycloalkyl, halocycloalkyl, alkoxy, haloalkoxy, alkylthio, haloalkylthio, alkylsulfinyl, haloalkylsulfinyl, alkylsulfonyl, haloalkylsulfonyl, alkylamino, dialkylamino, alkylcarbonyl, haloalkylcarbonyl, alkoxycarbonyl, haloalkoxycarbonyl, —$SF_5$, —CN, —$NO_2$ and —C(=S)—$NH_2$;
Q is X—$NR^2R^3$, the group (—$CH_2$—)(—$CH_2$—)N—$R^3$, which for avoidance of doubt represents the following structure herein:

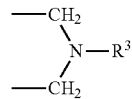

wherein each methylene group is bonded to a tetravalent atom of Y to form a spirocyclic group, OH, $NH_2$, alkoxy, haloalkoxy, alkylamino, haloalkylamino, dialkylamino, dihaloalkylamino, thiol, alkylthio, haloalkylthio, alkylsulfinyl, haloalkylsulfinyl, alkylsulfonyl, haloalkylsulfonyl, —$SF_5$, —C(=S)—$NH_2$, or an optionally substituted 5- or 6-membered carbocyclyl, heterocyclyl, heteroaryl ring, wherein the optional substituents of said carbocyclyl, heterocyclyl or heteroaryl ring are selected from halogen, alkyl, haloalkyl, alkoxy, haloalkoxy, alkylthio, haloalkylthio, alkylsulfinyl, haloalkylsulfinyl, alkylsulfonyl, haloalkylsulfonyl, alkylamino, dialkylamino, alkylcarbonyl, haloalkylcarbonyl, alkoxycarbonyl, haloalkoxycarbonyl, —$SF_5$, —CN, —$NO_2$ and —C(=S)—$NH_2$;
or the groups T1 or T2:

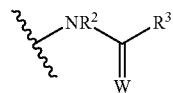

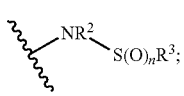

W is O or S;

X is $(CH_2)_n$, $CH(CH_3)$, $CH(CN)$, $C(=O)$ or $C(=S)$;

$R^2$ is H, alkyl, alkenyl, alkynyl, cycloalkyl, alkylcycloalkyl, cycloalkylalkyl, alkylcarbonyl or alkoxycarbonyl;

$R^3$ is H, OR, $NR^8R^9$ or $Q^1$; or alkyl, haloalkyl, alkenyl, haloalkenyl, alkynyl, cycloalkyl, alkylcycloalkyl, cycloalkylalkyl, alkylcarbonyl, alkoxycarbonyl, aminocarbonyl, alkylaminocarbonyl or dialkylaminocarbonyl, each optionally substituted with one or more substituents independently selected from $R^4$; or when Q is $X-NR^2R^3$, $R^2$ and $R^3$ taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of alkyl, haloalkyl, halogen, —CN, —$NO_2$, alkoxy and haloalkoxy;

each $R^4$ is independently halogen; alkyl, cycloalkyl, alkoxy, haloalkoxy, alkylthio, haloalkylthio, alkylsulfinyl, haloalkylsulfinyl, alkylsulfonyl, haloalkylsulfonyl, alkylamino, haloalkylamino, dialkylamino, dihaloalkylamino, cycloalkylamino, alkylcarbonyl, alkoxycarbonyl, alkylaminocarbonyl, dialkylaminocarbonyl, haloalkylcarbonyl, haloalkoxycarbonyl, haloalkylaminocarbonyl, dihaloalkylaminocarbonyl, hydroxy, —$SF_5$, —$C(=S)NH_2$, —$NH_2$, —CN or —$NO_2$; or $Q^2$;

each $R^5$ is independently halogen, alkoxy, haloalkoxy, alkylthio, haloalkylthio, alkylsulfinyl, haloalkylsulfinyl, alkylsulfonyl, haloalkylsulfonyl, alkylamino, dialkylamino, alkoxycarbonyl, —$SF_5$, —$C(=S)NH_2$, —CN or —$NO_2$;

each $R^6$ is independently halogen, alkyl, haloalkyl, cycloalkyl, halocycloalkyl, alkoxy, haloalkoxy, alkylthio, haloalkylthio, alkylsulfinyl, haloalkylsulfinyl, alkylsulfonyl, haloalkylsulfonyl, alkylamino, dialkylamino, —$SF_5$, —$C(=S)NH_2$, —CN, —$NO_2$, phenyl or pyridinyl;

$R^7$ is H; or alkyl, alkenyl, alkynyl, cycloalkyl, alkylcycloalkyl or cycloalkylalkyl, each optionally substituted with one or more halogen;

$R^8$ is H, alkyl, alkenyl, alkynyl, cycloalkyl, alkylcycloalkyl, cycloalkylalkyl, alkylcarbonyl or alkoxycarbonyl;

$R^9$ is H; $Q^3$; or alkyl, alkenyl, alkynyl, cycloalkyl, alkylcycloalkyl or cycloalkylalkyl, each optionally substituted with one or more substituents independently selected from $R^4$; or $R^8$ and $R^9$ taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of alkyl, haloalkyl, halogen, —CN, —$NO_2$, alkoxy and haloalkoxy;

$Q^1$ is a phenyl ring, a 5- or 6-membered heterocyclic ring, or an 8-, 9- or 10-membered fused bicyclic ring system optionally containing one to three heteroatoms selected from up to 1 O, up to 1 S and up to 3 N, each ring or ring system optionally substituted with one or more substituents independently selected from $R^5$;

$Q^2$ is independently a phenyl ring or a 5- or 6-membered heterocyclic ring, each ring optionally substituted with one or more substituents independently selected from $R^6$;

$Q^3$ is a phenyl ring or a 5- or 6-membered heterocyclic ring, each ring optionally substituted with one or more substituents independently selected from $R^6$; and n is 0, 1 or 2.

In one embodiment, in the compound of formula (I), as described above, $P^1$ and $P^2$ will be in a trans-relationship with respect to the double bond in the compound. For avoidance of doubt, when $P^1$ and $P^2$ are in a trans-relationship to each other they are on opposite sides of the double bond as shown below:

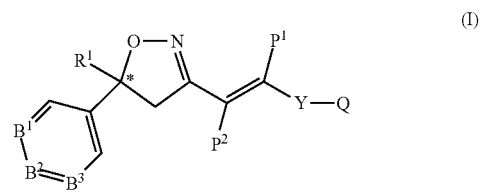

(I)

In another embodiment, $P^1$ and $P^2$ in the compound of formula (I), as described above, will be in a cis-relationship with respect to the double bond. Furthermore, in various embodiments, the isoxazoline compound of formula (I) will be present as mixture of trans- and cis-isomers with respect to variables $P^1$ and $P^2$. In one embodiment, the compound of formula (I) will be present in a mixture of trans- and cis-isomers in a weight:weight ratio of about 99:1 to about 1:99, trans-isomer to cis-isomer. In another embodiment, the compound of formula (I) will be present as a mixture of trans- and cis-isomers in a weight:weight ratio of about 95:5 to about 5:95, trans-isomer to cis-isomer. In yet other embodiments, the compound of formula (I) will be present as a mixture of trans- and cis-isomers in a weight:weight ratio of about 90:10 to about 10:90, about 70:30 to about 30:70, or about 60:40 to about 40:60, trans-isomer to cis-isomer.

In yet another embodiment, the compound of formula (I) will be present as a mixture of trans- and cis-isomers in a weight:weight ratio of about 99:1 to about 80:20, about 99:1 to about 85:15 or about 99:1 to about 90:10, trans-isomer to cis-isomer. In one embodiment, the compound of formula (I) will have less than about 1% by weight of the cis-isomer In other embodiments, the compound of formula (I) will have less than about 0.5% or less than about 0.1% of the cis-isomer.

In yet another embodiment, the compound of formula (I) will be present as a mixture of trans- and cis-isomers in a weight:weight ratio of about 99:1 to about 80:20, about 99:1 to about 85:15 or about 99:1 to about 90:10, cis-isomer to trans-isomer. In one embodiment, the compound of formula (I) will have less than about 1% by weight of the trans-isomer In other embodiments, the compound of formula (I) will have less than about 0.5% or less than about 0.1% of the trans-isomer.

In one embodiment, the invention provides compounds of formula (I) wherein Y is selected from Y-1, Y-2 where $Z^1$, $Z^2$, $Z^3$, $Z^4$, $Z^5$ and $Z^6$ are independently N or CH and wherein at most 3 Z groups are nitrogen, Y-3, Y-4 where Z is N or CH, Y-5 or Y-6 where $R^{10}$ and $R^{11}$ are independently H, $C_1$-$C_3$alkyl or $C_1$-$C_3$haloalkyl:

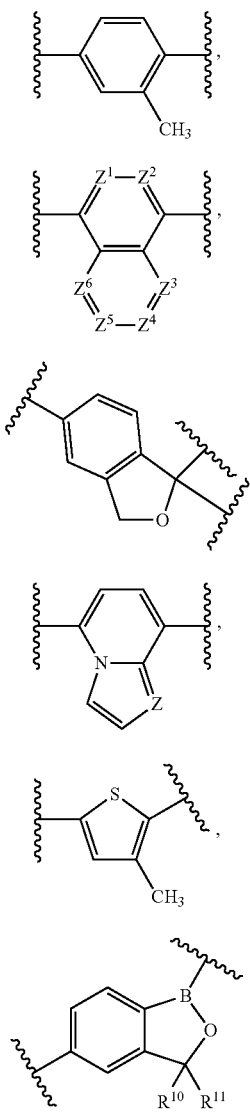

Y-1
Y-2
Y-3
Y-4
Y-5
Y-6

In one embodiment of the invention comprising an isoxazoline compound of formula (I), the group Q is X—$NR^2R^3$. In another embodiment, Q is X—$NR^2R^3$ wherein $R^2$ is H or $C_1$-$C_3$alkyl and $R^3$ is $C_1$-$C_3$alkyl optionally substituted by $R^4$. In yet another embodiment, Q is X—$NR^2R^3$ wherein $R^2$ is H and $R^3$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylcarbonyl, alkoxycarbonyl, alkylaminocarbonyl, dialkylaminocarbonyl, haloalkylcarbonyl, haloalkoxycarbonyl, haloalkylaminocarbonyl or dihaloalkylaminocarbonyl. In another embodiment, Q is X—$NR^2R^3$ wherein $R^2$ is H and $R^3$ is $C_1$-$C_3$alkyl optionally substituted by halogen, alkylthio, haloalkylthio, alkylaminocarbonyl, dialkylaminocarbonyl, haloalkylaminocarbonyl or dihaloalkylaminocarbonyl. In another embodiment, Q is X—$NR^2R^3$ wherein $R^2$ is H or $C_1$-$C_3$alkyl and $R^3$ is alkylcarbonyl, haloalkylcarbonyl. In another embodiment, Q is —C(O)$NHCH_2CF_3$. In another embodiment, Q is —C(O)$NHCH_2CH_2CF_3$. In yet another embodiment, Q is —C(O)$NHCF_3$. In still another embodiment, Q is —C(O)$NHCH_2C(O)NHCH_2CF_3$. In yet another embodiment, Q is —C(O)$CH_2S(O)_2CH_3$. In another embodiment, Q is —C(O)$NHCH_2CH_2SCH_3$. In another embodiment wherein Y is Y-3, Q is the group (—$CH_2$—)($CH_2$—)N—C(=O)$CH_2S(O)_2CH_3$.

In one embodiment, $P^1$ and $P^2$ are each independently hydrogen, halogen, cyano, $C_1$-$C_8$alkyl, $C_1$-$C_8$haloalkyl or $C_3C_8$cycloalkyl. In another embodiment, $P^1$ and $P^2$ are independently hydrogen, halogen, $C_1$-$C_4$alkyl or $C_1$-$C_4$haloalkyl. In yet another embodiment, $P^1$ and $P^2$ are independently hydrogen, halogen, $C_1$-$C_2$alkyl or $C_1$-$C_2$haloalkyl. In yet another embodiment, $P^1$ and $P^2$ are independently hydrogen, methyl, ethyl, chloro, bromo or trifluoromethyl. In another embodiment, $P^1$ and $P^2$ are both hydrogen.

In one embodiment, $R^1$ is $C_1$-$C_3$haloalkyl. In yet another embodiment, $R^1$ is $CFCl_2$. In another embodiment $R^1$ is $CF_2Cl$. In another embodiment, $R^1$ is $CFBr_2$. In another embodiment, $R^1$ is $CF_2Br$. In a particularly preferred embodiment, $R^1$ is $CF_3$.

In one embodiment of the compounds of formula (I), Y is Y-2 wherein $Z^1$ to $Z^6$ are all C—H. In another embodiment, Y is Y2 wherein $Z^1$ is N and $Z^2$ to $Z^6$ are C—H. In another embodiment, Y is Y-2 wherein $Z^2$ is N and $Z^1$ and $Z^3$ to $Z^6$ are C—H. In yet another embodiment, Y is Y-2 wherein $Z^3$ is N and $Z^1$, $Z^2$ and $Z^4$ to $Z^6$ are C—H. In still another embodiment, $Z^4$ is N and $Z^1$, $Z^2$, $Z^3$, $Z^5$ and $Z^6$ are C—H. In another embodiment, $Z^5$ is N and $Z^1$ to $Z^4$ and $Z^6$ are C—H.

In another embodiment, Y is Y2 wherein $Z^1$ and $Z^2$ are N and $Z^3$ to $Z^6$ are C—H. In another embodiment, Y is Y-2 wherein $Z^4$ and $Z^5$ are N and $Z^1$, $Z^2$, $Z^3$ and $Z^6$ are C—H. In yet another embodiment, Y is Y-2 wherein $Z^5$ and $Z^6$ are N and $Z^1$ to $Z^4$ are C—H. In still another embodiment, $Z^3$ and $Z^4$ are N and $Z^1$, $Z^2$, $Z^5$ and $Z^6$ are C—H.

In one embodiment, Y is Y-6 where $R^{10}$ and $R^{11}$ are both H. In another embodiment, Y is Y-6 wherein $R^{10}$ and $R^{11}$ are both $C_1$-$C_3$alkyl. In another embodiment, Y is Y-6 wherein $R^{10}$ and $R^{11}$ are independently $C_1$-$C_3$alkyl or $C_1$-$C_3$haloalkyl. In another embodiment, Y is Y-6 wherein $R^{10}$ and $R^{11}$ are independently H, methyl or ethyl. In yet another embodiment, Y is Y-6 wherein $R^{10}$ and $R^{11}$ are both methyl.

In one embodiment, the invention provides compounds of formula (I) wherein:
Y is Y-1;
$B^1$, $B^2$ and $B^3$ are each independently N, C—H, C-halogen or C—$C_1$-$C_3$haloalkyl;
$R^1$ is $CF_3$;
$P^1$ and $P^2$ are each independently hydrogen, halogen, cyano, $C_1$-$C_8$alkyl, $C_1$-$C_8$haloalkyl or $C_3C_8$cycloalkyl; and
Q is X—$NR^2R^3$ where $R^2$ is hydrogen and $R^3$ is alkyl optionally substituted by $R^4$.

In another embodiment, the invention provides compounds of formula (I) wherein:
Y is Y-1;
$B^1$, $B^2$ and $B^3$ are each independently N, C—H, C-halogen or C—$C_1$-$C_3$haloalkyl;
$R^1$ is $CF_3$;
$P^1$ and $P^2$ are each independently hydrogen, halogen, cyano, $C_1$-$C_4$alkyl, $C_1$-$C_4$haloalkyl or $C_3C_8$cycloalkyl; and
Q is X—$NR^2R^3$ where $R^2$ is hydrogen and $R^3$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylcarbonyl, alkoxycarbonyl, alkylaminocarbonyl, dialkylaminocarbonyl, haloalkylcarbonyl, haloalkoxycarbonyl, haloalkylaminocarbonyl or dihaloalkylaminocarbonyl.

In another embodiment, the invention provides compounds of formula (I) wherein:

Y is Y-1;
B$^1$, B$^2$ and B$^3$ are each independently C—H, C—Cl, C—F or C—CF$_3$;
R$^1$ is CF$_3$;
P$^1$ and P$^2$ are each independently hydrogen, halogen, cyano, C$_1$-C$_4$alkyl, C$_1$-C$_4$haloalkyl or C$_3$C$_8$cycloalkyl; and
Q is X—NR$^2$R$^3$ where R$^2$ is hydrogen and R$^3$ is C$_1$-C$_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylcarbonyl, haloalkoxycarbonyl, haloalkylaminocarbonyl or dihaloalkylaminocarbonyl.

In another embodiment, the invention provides compounds of formula (I) wherein:
Y is Y-1;
B$^1$, B$^2$ and B$^3$ are each independently C—H, C—Cl, C—F or C—CF$_3$;
R$^1$ is CF$_3$;
P$^1$ and P$^2$ are each independently hydrogen, halogen, cyano, C$_1$-C$_2$alkyl, C$_1$-C$_2$haloalkyl or C$_3$C$_8$cycloalkyl; and
Q is the group —C(O)NHCH$_2$C(O)NHCH$_2$CF$_3$ or —C(O)NHCH$_2$CH$_2$SCH$_3$.

In another embodiment, the invention provides compounds of formula (I) wherein:
Y is Y-1;
B$^1$ is C—Cl, B$^2$ is C—H or C—F, and B$^3$ is C—Cl or C—CF$_3$;
R$^1$ is CF$_3$;
P$^1$ and P$^2$ are each independently hydrogen, methyl, ethyl, chloro, bromo or trifluoromethyl; and
Q is the group —C(O)NHCH$_2$C(O)NHCH$_2$CF$_3$, —C(O)NHCH$_2$CF$_3$, —C(O)NHCF$_3$ or —C(O)NHCH$_2$CH$_2$SCH$_3$.

In one embodiment, the invention provides compounds of formula (I) wherein:
Y is Y-2;
B$^1$, B$^2$ and B$^3$ are each independently N, C—H, C-halogen or C—C$_1$-C$_3$haloalkyl;
R$^1$ is CF$_3$;
P$^1$ and P$^2$ are each independently hydrogen, halogen, cyano, C$_1$-C$_8$alkyl, C$_1$-C$_8$haloalkyl or C$_3$C$_8$cycloalkyl; and
Q is X—NR$^2$R$^3$ where R$^2$ is hydrogen and R$^3$ is alkyl optionally substituted by R$^4$.

In another embodiment, the invention provides compounds of formula (I) wherein:
Y is Y-2;
B$^1$, B$^2$ and B$^3$ are each independently N, C—H, C-halogen or C—C$_1$-C$_3$haloalkyl;
R$^1$ is CF$_3$;
P$^1$ and P$^2$ are each independently hydrogen, halogen, cyano, C$_1$-C$_4$alkyl, C$_1$-C$_4$haloalkyl or C$_3$C$_8$cycloalkyl; and
Q is X—NR$^2$R$^3$ where R$^2$ is hydrogen and R$^3$ is C$_1$-C$_3$alkyl optionally substituted by halogen, alkylthio, haloalkylthio, alkylsulfinyl, haloalkylsulfinyl, alkylsulfonyl, haloalkylsulfonyl, alkylcarbonyl, alkoxycarbonyl, alkylaminocarbonyl, dialkylaminocarbonyl, haloalkylcarbonyl, haloalkoxycarbonyl, haloalkylaminocarbonyl or dihaloalkylaminocarbonyl.

In another embodiment, the invention provides compounds of formula (I) wherein:
Y is Y-2;
B$^1$, B$^2$ and B$^3$ are each independently C—H, C—Cl, C—F or C—CF$_3$;
R$^1$ is CF$_3$;
P$^1$ and P$^2$ are each independently hydrogen, halogen, cyano, C$_1$-C$_4$alkyl, C$_1$-C$_4$haloalkyl or C$_3$C$_8$cycloalkyl; and
Q is X—NR$^2$R$^3$ where R$^2$ is hydrogen and R$^3$ is C$_1$-C$_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylcarbonyl, haloalkoxycarbonyl, haloalkylaminocarbonyl or dihaloalkylaminocarbonyl.

In another embodiment, the invention provides compounds of formula (I) wherein:
Y is Y-2;
B$^1$, B$^2$ and B$^3$ are each independently C—H, C—Cl, C—F or C—CF$_3$;
R$^1$ is CF$_3$;
P$^1$ and P$^2$ are each independently hydrogen, halogen, cyano, C$_1$-C$_2$alkyl, C$_1$-C$_2$haloalkyl or C$_3$C$_8$cycloalkyl; and
Q is the group —C(O)NHCH$_2$C(O)NHCH$_2$CF$_3$ or —C(O)NHCH$_2$CH$_2$SCH$_3$.

In another embodiment, the invention provides compounds of formula (I) wherein:
Y is Y-2;
B$^1$ is C—Cl, B$^2$ is C—H or C—F, and B$^3$ is C—Cl or C—CF$_3$;
R$^1$ is CF$_3$;
P$^1$ and P$^2$ are each independently hydrogen, methyl, ethyl, chloro, bromo or trifluoromethyl; and
Q is the group —C(O)NHCH$_2$C(O)NHCH$_2$CF$_3$, —C(O)NHCH$_2$CF$_3$, —C(O)NHCF$_3$ or —C(O)NHCH$_2$CH$_2$SCH$_3$.

In one embodiment, the invention provides compounds of formula (I) wherein:
Y is Y-2 wherein Z$^1$ to Z$^6$ are C—H;
B$^1$, B$^2$ and B$^3$ are each independently N, C—H, C-halogen or C—C$_1$-C$_3$haloalkyl;
R$^1$ is CF$_3$;
P$^1$ and P$^2$ are each independently hydrogen, halogen, cyano, C$_1$-C$_8$alkyl, C$_1$-C$_8$haloalkyl or C$_3$C$_8$cycloalkyl; and
Q is X—NR$^2$R$^3$ where R$^2$ is hydrogen and R$^3$ is alkyl optionally substituted by R$^4$.

In another embodiment, the invention provides compounds of formula (I) wherein:
Y is Y-2 wherein Z$^1$ to Z$^6$ are C—H;
B$^1$, B$^2$ and B$^3$ are each independently N, C—H, C-halogen or C—C$_1$-C$_3$haloalkyl;
R$^1$ is CF$_3$;
P$^1$ and P$^2$ are each independently hydrogen, halogen, cyano, C$_1$-C$_4$alkyl, C$_1$-C$_4$haloalkyl or C$_3$C$_8$cycloalkyl; and
Q is X—NR$^2$R$^3$ where R$^2$ is hydrogen and R$^3$ is C$_1$-C$_3$alkyl optionally substituted by halogen, alkylthio, haloalkylthio, alkylsulfinyl, haloalkylsulfinyl, alkylsulfonyl, haloalkylsulfonyl, alkylcarbonyl, alkoxycarbonyl, alkylaminocarbonyl, dialkylaminocarbonyl, haloalkylcarbonyl, haloalkoxycarbonyl, haloalkylaminocarbonyl or dihaloalkylaminocarbonyl.

In another embodiment, the invention provides compounds of formula (I) wherein:
Y is Y-2 wherein Z$^1$ to Z$^6$ are C—H;
B$^1$, B$^2$ and B$^3$ are each independently C—H, C—Cl, C—F or C—CF$_3$;
R$^1$ is CF$_3$;
P$^1$ and P$^2$ are each independently hydrogen, halogen, cyano, C$_1$-C$_4$alkyl, C$_1$-C$_4$haloalkyl or C$_3$C$_8$cycloalkyl; and
Q is X—NR$^2$R$^3$ where R$^2$ is hydrogen and R$^3$ is C$_1$-C$_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylcarbonyl, haloalkoxycarbonyl, haloalkylaminocarbonyl or dihaloalkylaminocarbonyl.

In another embodiment, the invention provides compounds of formula (I) wherein:

Y is Y-2 wherein $Z^1$ to $Z^6$ are C—H;
$B^1$, $B^2$ and $B^3$ are each independently C—H, C—Cl, C—F or C—$CF_3$;
$R^1$ is $CF_3$;
$P^1$ and $P^2$ are each independently hydrogen, halogen, cyano, $C_1$-$C_2$alkyl, $C_1$-$C_2$haloalkyl or $C_3C_8$cycloalkyl; and
Q is the group —C(O)NHCH$_2$C(O)NHCH$_2$CF$_3$ or —C(O)NHCH$_2$CH$_2$SCH$_3$.

In another embodiment, the invention provides compounds of formula (I) wherein:
Y is Y-2 wherein $Z^1$ to $Z^6$ are C—H;
$B^1$ is C—Cl, $B^2$ is C—H or C—F, and $B^3$ is C—Cl or C—$CF_3$;
$R^1$ is $CF_3$;
$P^1$ and $P^2$ are each independently hydrogen, methyl, ethyl, chloro, bromo or trifluoromethyl; and
Q is the group —C(O)NHCH$_2$C(O)NHCH$_2$CF$_3$, —C(O)NHCH$_2$CF$_3$, —C(O)NHCF$_3$ or —C(O)NHCH$_2$CH$_2$SCH$_3$.

In one embodiment, the invention provides compounds of formula (I) wherein:
Y is Y-2 wherein $Z^1$ is N and $Z^2$ to $Z^6$ are C—H;
$B^1$, $B^2$ and $B^3$ are each independently N, C—H, C-halogen or C—$C_1$-$C_3$haloalkyl;
$R^1$ is $CF_3$;
$P^1$ and $P^2$ are each independently hydrogen, halogen, cyano, $C_1$-$C_8$alkyl, $C_1$-$C_8$haloalkyl or $C_3C_8$cycloalkyl; and
Q is X—NR$^2$R$^3$ where $R^2$ is hydrogen and $R^3$ is alkyl optionally substituted by $R^4$.

In another embodiment, the invention provides compounds of formula (I) wherein:
Y is Y-2 wherein $Z^1$ is N and $Z^2$ to $Z^6$ are C—H;
$B^1$, $B^2$ and $B^3$ are each independently N, C—H, C-halogen or C—$C_1$-$C_3$haloalkyl;
$R^1$ is $CF_3$;
$P^1$ and $P^2$ are each independently hydrogen, halogen, cyano, $C_1$-$C_4$alkyl, $C_1$-$C_4$haloalkyl or $C_3C_8$cycloalkyl; and
Q is X—NR$^2$R$^3$ where $R^2$ is hydrogen and $R^3$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylcarbonyl, alkoxycarbonyl, alkylaminocarbonyl, dialkylaminocarbonyl, haloalkylcarbonyl, haloalkoxycarbonyl, haloalkylaminocarbonyl or dihaloalkylaminocarbonyl.

In another embodiment, the invention provides compounds of formula (I) wherein:
Y is Y-2 wherein $Z^1$ is N and $Z^2$ to $Z^6$ are C—H;
$B^1$, $B^2$ and $B^3$ are each independently C—H, C—Cl, C—F or C—$CF_3$;
$R^1$ is $CF_3$;
$P^1$ and $P^2$ are each independently hydrogen, halogen, cyano, $C_1$-$C_4$alkyl, $C_1$-$C_4$haloalkyl or $C_3C_8$cycloalkyl; and
Q is X—NR$^2$R$^3$ where $R^2$ is hydrogen and $R^3$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylcarbonyl, haloalkoxycarbonyl, haloalkylaminocarbonyl or dihaloalkylaminocarbonyl.

In another embodiment, the invention provides compounds of formula (I) wherein:
Y is Y-2 wherein $Z^1$ is N and $Z^2$ to $Z^6$ are C—H;
$B^1$, $B^2$ and $B^3$ are each independently C—H, C—Cl, C—F or C—$CF_3$;
$R^1$ is $CF_3$;
$P^1$ and $P^2$ are each independently hydrogen, halogen, cyano, $C_1$-$C_2$alkyl, $C_1$-$C_2$haloalkyl or $C_3C_8$cycloalkyl; and
Q is the group —C(O)NHCH$_2$C(O)NHCH$_2$CF$_3$ or —C(O)NHCH$_2$CH$_2$SCH$_3$.

In another embodiment, the invention provides compounds of formula (I) wherein:
Y is Y-2 wherein $Z^1$ is N and $Z^2$ to $Z^6$ are C—H;
$B^1$ is C—Cl, $B^2$ is C—H or C—F, and $B^3$ is C—Cl or C—$CF_3$;
$R^1$ is $CF_3$;
$P^1$ and $P^2$ are each independently hydrogen, methyl, ethyl, chloro, bromo or trifluoromethyl; and
Q is the group —C(O)NHCH$_2$C(O)NHCH$_2$CF$_3$, —C(O)NHCH$_2$CF$_3$, —C(O)NHCF$_3$ or —C(O)NHCH$_2$CH$_2$SCH$_3$.

In one embodiment, the invention provides compounds of formula (I) wherein:
Y is Y-2 wherein $Z^2$ is N and $Z^1$ and $Z^3$ to $Z^6$ are C—H;
$B^1$, $B^2$ and $B^3$ are each independently N, C—H, C-halogen or C—$C_1$-$C_3$haloalkyl;
$R^1$ is $CF_3$;
$P^1$ and $P^2$ are each independently hydrogen, halogen, cyano, $C_1$-$C_8$alkyl, $C_1$-$C_8$haloalkyl or $C_3C_8$cycloalkyl; and
Q is X—NR$^2$R$^3$ where $R^2$ is hydrogen and $R^3$ is alkyl optionally substituted by $R^4$.

In another embodiment, the invention provides compounds of formula (I) wherein:
Y is Y-2 wherein $Z^2$ is N and $Z^1$ and $Z^3$ to $Z^6$ are C—H;
$B^1$, $B^2$ and $B^3$ are each independently N, C—H, C-halogen or C—$C_1$-$C_3$haloalkyl;
$R^1$ is $CF_3$;
$P^1$ and $P^2$ are each independently hydrogen, halogen, cyano, $C_1$-$C_4$alkyl, $C_1$-$C_4$haloalkyl or $C_3C_8$cycloalkyl; and
Q is X—NR$^2$R$^3$ where $R^2$ is hydrogen and $R^3$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylcarbonyl, alkoxycarbonyl, alkylaminocarbonyl, dialkylaminocarbonyl, haloalkylcarbonyl, haloalkoxycarbonyl, haloalkylaminocarbonyl or dihaloalkylaminocarbonyl.

In another embodiment, the invention provides compounds of formula (I) wherein:
Y is Y-2 wherein $Z^2$ is N and $Z^1$ and $Z^3$ to $Z^6$ are C—H;
$B^1$, $B^2$ and $B^3$ are each independently C—H, C—Cl, C—F or C—$CF_3$;
$R^1$ is $CF_3$;
$P^1$ and $P^2$ are each independently hydrogen, halogen, cyano, $C_1$-$C_4$alkyl, $C_1$-$C_4$haloalkyl or $C_3C_8$cycloalkyl; and
Q is X—NR$^2$R$^3$ where $R^2$ is hydrogen and $R^3$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylcarbonyl, haloalkoxycarbonyl, haloalkylaminocarbonyl or dihaloalkylaminocarbonyl.

In another embodiment, the invention provides compounds of formula (I) wherein:
Y is Y-2 wherein $Z^2$ is N and $Z^1$ and $Z^3$ to $Z^6$ are C—H;
$B^1$, $B^2$ and $B^3$ are each independently C—H, C—Cl, C—F or C—$CF_3$;
$R^1$ is $CF_3$;
$P^1$ and $P^2$ are each independently hydrogen, halogen, cyano, $C_1$-$C_2$alkyl, $C_1$-$C_2$haloalkyl or $C_3C_8$cycloalkyl; and
Q is the group —C(O)NHCH$_2$C(O)NHCH$_2$CF$_3$ or —C(O)NHCH$_2$CH$_2$SCH$_3$.

In another embodiment, the invention provides compounds of formula (I) wherein:
Y is Y-2 wherein $Z^2$ is N and $Z^1$ and $Z^3$ to $Z^6$ are C—H;
$B^1$ is C—Cl, $B^2$ is C—H or C—F, and $B^3$ is C—Cl or C—$CF_3$;
$R^1$ is $CF_3$;
$P^1$ and $P^2$ are each independently hydrogen, methyl, ethyl, chloro, bromo or trifluoromethyl; and Q is the group —C(O)NHCH$_2$C(O)NHCH$_2$CF$_3$, —C(O)NHCH$_2$CF$_3$, —C(O)NHCF$_3$ or —C(O)NHCH$_2$CH$_2$SCH$_3$.

In one embodiment, the invention provides compounds of formula (I) wherein:
Y is Y-2 wherein Z$^3$ is N and Z$^1$, Z$^2$ and Z$^4$ to Z$^6$ are C—H;
B$^1$, B$^2$ and B$^3$ are each independently N, C—H, C-halogen or C—C$_1$-C$_3$haloalkyl;
R$^1$ is CF$_3$;
P$^1$ and P$^2$ are each independently hydrogen, halogen, cyano, C$_1$-C$_8$alkyl, C$_1$-C$_8$haloalkyl or C$_3$C$_8$cycloalkyl; and
Q is X—NR$^2$R$^3$ where R$^2$ is hydrogen and R$^3$ is alkyl optionally substituted by R$^4$.

In another embodiment, the invention provides compounds of formula (I) wherein:
Y is Y-2 wherein Z$^3$ is N and Z$^1$, Z$^2$ and Z$^4$ to Z$^6$ are C—H;
B$^1$, B$^2$ and B$^3$ are each independently N, C—H, C-halogen or C—C$_1$-C$_3$haloalkyl;
R$^1$ is CF$_3$;
P$^1$ and P$^2$ are each independently hydrogen, halogen, cyano, C$_1$-C$_4$alkyl, C$_1$-C$_4$haloalkyl or C$_3$C$_8$cycloalkyl; and
Q is X—NR$^2$R$^3$ where R$^2$ is hydrogen and R$^3$ is C$_1$-C$_3$alkyl optionally substituted by halogen, alkylthio, haloalkylthio, alkylsulfinyl, haloalkylsulfinyl, alkylsulfonyl, haloalkylsulfonyl, alkylcarbonyl, alkoxycarbonyl, alkylaminocarbonyl, dialkylaminocarbonyl, haloalkylcarbonyl, haloalkoxycarbonyl, haloalkylaminocarbonyl or dihaloalkylaminocarbonyl.

In another embodiment, the invention provides compounds of formula (I) wherein:
Y is Y-2 wherein Z$^3$ is N and Z$^1$, Z$^2$ and Z$^4$ to Z$^6$ are C—H;
B$^1$, B$^2$ and B$^3$ are each independently C—H, C—Cl, C—F or C—CF$_3$;
R$^1$ is CF$_3$;
P$^1$ and P$^2$ are each independently hydrogen, halogen, cyano, C$_1$-C$_4$alkyl, C$_1$-C$_4$haloalkyl or C$_3$C$_8$cycloalkyl; and
Q is X—NR$^2$R$^3$ where R$^2$ is hydrogen and R$^3$ is C$_1$-C$_3$alkyl optionally substituted by halogen, alkylthio, haloalkylthio, alkylsulfinyl, haloalkylsulfinyl, alkylsulfonyl, haloalkylsulfonyl, alkylcarbonyl, alkoxycarbonyl, alkylaminocarbonyl, dialkylaminocarbonyl, haloalkylcarbonyl, haloalkoxycarbonyl, haloalkylaminocarbonyl or dihaloalkylaminocarbonyl.

In another embodiment, the invention provides compounds of formula (I) wherein:
Y is Y-2 wherein Z$^3$ is N and Z$^1$, Z$^2$ and Z$^4$ to Z$^6$ are C—H;
B$^1$, B$^2$ and B$^3$ are each independently C—H, C—Cl, C—F or C—CF$_3$;
R$^1$ is CF$_3$;
P$^1$ and P$^2$ are each independently hydrogen, halogen, cyano, C$_1$-C$_2$alkyl, C$_1$-C$_2$haloalkyl or C$_3$C$_8$cycloalkyl; and
Q is the group —C(O)NHCH$_2$C(O)NHCH$_2$CF$_3$ or —C(O)NHCH$_2$CH$_2$SCH$_3$.

In another embodiment, the invention provides compounds of formula (I) wherein:
Y is Y-2 wherein Z$^3$ is N and Z$^1$, Z$^2$ and Z$^4$ to Z$^6$ are C—H;
B$^1$ is C—Cl, B$^2$ is C—H or C—F, and B$^3$ is C—Cl or C—CF$_3$;
R$^1$ is CF$_3$;
P$^1$ and P$^2$ are each independently hydrogen, methyl, ethyl, chloro, bromo or trifluoromethyl; and
Q is the group —C(O)NHCH$_2$C(O)NHCH$_2$CF$_3$, —C(O)NHCH$_2$CF$_3$, —C(O)NHCF$_3$ or —C(O)NHCH$_2$CH$_2$SCH$_3$.

In one embodiment, the invention provides compounds of formula (I) wherein:
Y is Y-2 wherein Z$^4$ is N and Z$^1$, Z$^2$, Z$^3$, Z$^5$ and Z$^6$ are C—H;
B$^1$, B$^2$ and B$^3$ are each independently N, C—H, C-halogen or C—C$_1$-C$_3$haloalkyl;
R$^1$ is CF$_3$;
P$^1$ and P$^2$ are each independently hydrogen, halogen, cyano, C$_1$-C$_8$alkyl, C$_1$-C$_8$haloalkyl or C$_3$C$_8$cycloalkyl; and
Q is X—NR$^2$R$^3$ where R$^2$ is hydrogen and R$^3$ is alkyl optionally substituted by R$^4$.

In another embodiment, the invention provides compounds of formula (I) wherein:
Y is Y-2 wherein Z$^4$ is N and Z$^1$, Z$^2$, Z$^3$, Z$^5$ and Z$^6$ are C—H;
B$^1$, B$^2$ and B$^3$ are each independently N, C—H, C-halogen or C—C$_1$-C$_3$haloalkyl;
R$^1$ is CF$_3$;
P$^1$ and P$^2$ are each independently hydrogen, halogen, cyano, C$_1$-C$_4$alkyl, C$_1$-C$_4$haloalkyl or C$_3$C$_8$cycloalkyl; and
Q is X—NR$^2$R$^3$ where R$^2$ is hydrogen and R$^3$ is C$_1$-C$_3$alkyl optionally substituted by halogen, alkylthio, haloalkylthio, alkylsulfinyl, haloalkylsulfinyl, alkylsulfonyl, haloalkylsulfonyl, alkylcarbonyl, alkoxycarbonyl, alkylaminocarbonyl, dialkylaminocarbonyl, haloalkylcarbonyl, haloalkoxycarbonyl, haloalkylaminocarbonyl or dihaloalkylaminocarbonyl.

In another embodiment, the invention provides compounds of formula (I) wherein:
Y is Y-2 wherein Z$^4$ is N and Z$^1$, Z$^2$, Z$^3$, Z$^5$ and Z$^6$ are C—H;
B$^1$, B$^2$ and B$^3$ are each independently C—H, C—Cl, C—F or C—CF$_3$;
R$^1$ is CF$_3$;
P$^1$ and P$^2$ are each independently hydrogen, halogen, cyano, C$_1$-C$_4$alkyl, C$_1$-C$_4$haloalkyl or C$_3$C$_8$cycloalkyl; and
Q is X—NR$^2$R$^3$ where R$^2$ is hydrogen and R$^3$ is C$_1$-C$_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylcarbonyl, haloalkoxycarbonyl, haloalkylaminocarbonyl or dihaloalkylaminocarbonyl.

In another embodiment, the invention provides compounds of formula (I) wherein:
Y is Y-2 wherein Z$^4$ is N and Z$^1$, Z$^2$, Z$^3$, Z$^5$ and Z$^6$ are C—H;
B$^1$, B$^2$ and B$^3$ are each independently C—H, C—Cl, C—F or C—CF$_3$;
R$^1$ is CF$_3$;
P$^1$ and P$^2$ are each independently hydrogen, halogen, cyano, C$_1$-C$_2$alkyl, C$_1$-C$_2$haloalkyl or C$_3$C$_8$cycloalkyl; and
Q is the group —C(O)NHCH$_2$C(O)NHCH$_2$CF$_3$ or —C(O)NHCH$_2$CH$_2$SCH$_3$.

In another embodiment, the invention provides compounds of formula (I) wherein:
Y is Y-2 wherein Z$^4$ is N and Z$^1$, Z$^2$, Z$^3$, Z$^5$ and Z$^6$ are C—H;
B$^1$ is C—Cl, B$^2$ is C—H or C—F, and B$^3$ is C—Cl or C—CF$_3$;
R$^1$ is CF$_3$;
P$^1$ and P$^2$ are each independently hydrogen, methyl, ethyl, chloro, bromo or trifluoromethyl; and
Q is the group —C(O)NHCH$_2$C(O)NHCH$_2$CF$_3$, —C(O)NHCH$_2$CF$_3$, —C(O)NHCF$_3$ or —C(O)NHCH$_2$CH$_2$SCH$_3$.

In one embodiment, the invention provides compounds of formula (I) wherein:
Y is Y-2 wherein Z$^5$ is N and Z$^1$, Z$^2$, Z$^3$, Z$^4$ and Z$^6$ are C—H;
B$^1$, B$^2$ and B$^3$ are each independently N, C—H, C-halogen or C—C$_1$-C$_3$haloalkyl;
R$^1$ is CF$_3$;
P$^1$ and P$^2$ are each independently hydrogen, halogen, cyano, C$_1$-C$_8$alkyl, C$_1$-C$_8$haloalkyl or C$_3$C$_8$cycloalkyl; and Q is X—NR²R³ where R² is hydrogen and R³ is alkyl optionally substituted by R⁴.

In another embodiment, the invention provides compounds of formula (I) wherein:
Y is Y-2 wherein $Z^5$ is N and $Z^1$, $Z^2$, $Z^3$, $Z^4$ and $Z^6$ are C—H;
$B^1$, $B^2$ and $B^3$ are each independently N, C—H, C-halogen or C—$C_1$-$C_3$haloalkyl;
$R^1$ is $CF_3$;
$P^1$ and $P^2$ are each independently hydrogen, halogen, cyano, $C_1$-$C_4$alkyl, $C_1$-$C_4$haloalkyl or $C_3C_8$cycloalkyl; and
Q is X—NR²R³ where R² is hydrogen and R³ is $C_1$-$C_3$alkyl optionally substituted by halogen, alkylthio, haloalkylthio, alkylsulfinyl, haloalkylsulfinyl, alkylsulfonyl, haloalkylsulfonyl, alkylcarbonyl, alkoxycarbonyl, alkylaminocarbonyl, dialkylaminocarbonyl, haloalkylcarbonyl, haloalkoxycarbonyl, haloalkylaminocarbonyl or dihaloalkylaminocarbonyl.

In another embodiment, the invention provides compounds of formula (I) wherein:
Y is Y-2 wherein $Z^5$ is N and $Z^1$, $Z^2$, $Z^3$, $Z^4$ and $Z^6$ are C—H;
$B^1$, $B^2$ and $B^3$ are each independently C—H, C—Cl, C—F or C—$CF_3$;
$R^1$ is $CF_3$;
$P^1$ and $P^2$ are each independently hydrogen, halogen, cyano, $C_1$-$C_4$alkyl, $C_1$-$C_4$haloalkyl or $C_3C_8$cycloalkyl; and
Q is X—NR²R³ where R² is hydrogen and R³ is $C_1$-$C_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylcarbonyl, haloalkoxycarbonyl, haloalkylaminocarbonyl or dihaloalkylaminocarbonyl.

In another embodiment, the invention provides compounds of formula (I) wherein:
Y is Y-2 wherein $Z^5$ is N and $Z^1$, $Z^2$, $Z^3$, $Z^4$ and $Z^6$ are C—H;
$B^1$, $B^2$ and $B^3$ are each independently C—H, C—Cl, C—F or C—$CF_3$;
$R^1$ is $CF_3$;
$P^1$ and $P^2$ are each independently hydrogen, halogen, cyano, $C_1$-$C_2$alkyl, $C_1$-$C_2$haloalkyl or $C_3C_8$cycloalkyl; and
Q is the group —C(O)NHCH₂C(O)NHCH₂CF₃ or —C(O)NHCH₂CH₂SCH₃.

In another embodiment, the invention provides compounds of formula (I) wherein:
Y is Y-2 wherein $Z^5$ is N and $Z^1$, $Z^2$, $Z^3$, $Z^4$ and $Z^6$ are C—H;
$B^1$ is C—Cl, $B^2$ is C—H or C—F, and $B^3$ is C—Cl or C—$CF_3$;
$R^1$ is $CF_3$;
$P^1$ and $P^2$ are each independently hydrogen, methyl, ethyl, chloro, bromo or trifluoromethyl; and
Q is the group —C(O)NHCH₂C(O)NHCH₂CF₃, —C(O)NHCH₂CF₃, —C(O)NHCF₃ or —C(O)NHCH₂CH₂SCH₃.

In one embodiment, the invention provides compounds of formula (I) wherein:
Y is Y-2 wherein $Z^6$ is N and $Z^1$ to $Z^5$ are C—H;
$B^1$, $B^2$ and $B^3$ are each independently N, C—H, C-halogen or C—$C_1$-$C_3$haloalkyl;
$R^1$ is $CF_3$;
$P^1$ and $P^2$ are each independently hydrogen, halogen, cyano, $C_1$-$C_8$alkyl, $C_1$-$C_8$haloalkyl or $C_3C_8$cycloalkyl; and
Q is X—NR²R³ where R² is hydrogen and R³ is alkyl optionally substituted by R⁴.

In another embodiment, the invention provides compounds of formula (I) wherein:
Y is Y-2 wherein $Z^6$ is N and $Z^1$ to $Z^5$ are C—H;
$B^1$, $B^2$ and $B^3$ are each independently N, C—H, C-halogen or C—$C_1$-$C_3$haloalkyl;
$R^1$ is $CF_3$;
$P^1$ and $P^2$ are each independently hydrogen, halogen, cyano, $C_1$-$C_4$alkyl, $C_1$-$C_4$haloalkyl or $C_3C_8$cycloalkyl; and
Q is X—NR²R³ where R² is hydrogen and R³ is $C_1$-$C_3$alkyl optionally substituted by halogen, alkylthio, haloalkylthio, alkylsulfinyl, haloalkylsulfinyl, alkylsulfonyl, haloalkylsulfonyl, alkylcarbonyl, alkoxycarbonyl, alkylaminocarbonyl, dialkylaminocarbonyl, haloalkylcarbonyl, haloalkoxycarbonyl, haloalkylaminocarbonyl or dihaloalkylaminocarbonyl.

In another embodiment, the invention provides compounds of formula (I) wherein:
Y is Y-2 wherein $Z^6$ is N and $Z^1$ to $Z^5$ are C—H;
$B^1$, $B^2$ and $B^3$ are each independently C—H, C—Cl, C—F or C—$CF_3$;
$R^1$ is $CF_3$;
$P^1$ and $P^2$ are each independently hydrogen, halogen, cyano, $C_1$-$C_4$alkyl, $C_1$-$C_4$haloalkyl or $C_3C_8$cycloalkyl; and
Q is X—NR²R³ where R² is hydrogen and R³ is $C_1$-$C_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylcarbonyl, haloalkoxycarbonyl, haloalkylaminocarbonyl or dihaloalkylaminocarbonyl.

In another embodiment, the invention provides compounds of formula (I) wherein:
Y is Y-2 wherein $Z^6$ is N and $Z^1$ to $Z^5$ are C—H;
$B^1$, $B^2$ and $B^3$ are each independently C—H, C—Cl, C—F or C—$CF_3$;
$R^1$ is $CF_3$;
$P^1$ and $P^2$ are each independently hydrogen, halogen, cyano, $C_1$-$C_2$alkyl, $C_1$-$C_2$haloalkyl or $C_3C_8$cycloalkyl; and
Q is the group —C(O)NHCH₂C(O)NHCH₂CF₃ or —C(O)NHCH₂CH₂SCH₃.

In another embodiment, the invention provides compounds of formula (I) wherein:
Y is Y-2 wherein $Z^6$ is N and $Z^1$ to $Z^5$ are C—H;
$B^1$ is C—Cl, $B^2$ is C—H or C—F, and $B^3$ is C—Cl or C—$CF_3$;
$R^1$ is $CF_3$;
$P^1$ and $P^2$ are each independently hydrogen, methyl, ethyl, chloro, bromo or trifluoromethyl; and
Q is the group —C(O)NHCH₂C(O)NHCH₂CF₃, —C(O)NHCH₂CF₃, —C(O)NHCF₃ or —C(O)NHCH₂CH₂SCH₃.

In one embodiment, the invention provides compounds of formula (I) wherein:
Y is Y-2 wherein $Z^1$ and $Z^2$ are N and $Z^3$ to $Z^6$ are C—H;
$B^1$, $B^2$ and $B^3$ are each independently N, C—H, C-halogen or C—$C_1$-$C_3$haloalkyl;
$R^1$ is $CF_3$;
$P^1$ and $P^2$ are each independently hydrogen, halogen, cyano, $C_1$-$C_8$alkyl, $C_1$-$C_8$haloalkyl or $C_3C_8$cycloalkyl; and
Q is X—NR²R³ where R² is hydrogen and R³ is alkyl optionally substituted by R⁴.

In another embodiment, the invention provides compounds of formula (I) wherein:
Y is Y-2 wherein $Z^1$ and $Z^2$ are N and $Z^3$ to $Z^6$ are C—H;
$B^1$, $B^2$ and $B^3$ are each independently N, C—H, C-halogen or C—$C_1$-$C_3$haloalkyl;
$R^1$ is $CF_3$;
$P^1$ and $P^2$ are each independently hydrogen, halogen, cyano, $C_1$-$C_4$alkyl, $C_1$-$C_4$haloalkyl or $C_3C_8$cycloalkyl; and
Q is X—NR²R³ where R² is hydrogen and R³ is $C_1$-$C_3$alkyl optionally substituted by halogen, alkylthio, haloalkylthio, alkylsulfinyl, haloalkylsulfinyl, alkylsulfonyl, haloalkylsulfonyl, alkylcarbonyl, alkoxycarbonyl, alkylaminocarbonyl, dialkylaminocarbonyl, haloalkylcarbonyl, haloalkoxycarbonyl, haloalkylaminocarbonyl or dihaloalkylaminocarbonyl.

In another embodiment, the invention provides compounds of formula (I) wherein:

Y is Y-2 wherein $Z^1$ and $Z^2$ are N and $Z^3$ to $Z^6$ are C—H;

$B^1$, $B^2$ and $B^3$ are each independently C—H, C—Cl, C—F or C—$CF_3$;

$R^1$ is $CF_3$;

$P^1$ and $P^2$ are each independently hydrogen, halogen, cyano, $C_1$-$C_4$alkyl, $C_1$-$C_4$haloalkyl or $C_3C_8$cycloalkyl; and Q is X—$NR^2R^3$ where $R^2$ is hydrogen and $R^3$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylcarbonyl, haloalkoxycarbonyl, haloalkylaminocarbonyl or dihaloalkylaminocarbonyl.

In another embodiment, the invention provides compounds of formula (I) wherein:

Y is Y-2 wherein $Z^1$ and $Z^2$ are N and $Z^3$ to $Z^6$ are C—H;

$B^1$, $B^2$ and $B^3$ are each independently C—H, C—Cl, C—F or C—$CF_3$;

$R^1$ is $CF_3$;

$P^1$ and $P^2$ are each independently hydrogen, halogen, cyano, $C_1$-$C_2$alkyl, $C_1$-$C_2$haloalkyl or $C_3C_8$cycloalkyl; and Q is the group —C(O)NHCH$_2$C(O)NHCH$_2$CF$_3$ or —C(O)NHCH$_2$CH$_2$SCH$_3$.

In another embodiment, the invention provides compounds of formula (I) wherein:

Y is Y-2 wherein $Z^1$ and $Z^2$ are N and $Z^3$ to $Z^6$ are C—H;

$B^1$ is C—Cl, $B^2$ is C—H or C—F, and $B^3$ is C—Cl or C—$CF_3$;

$R^1$ is $CF_3$;

$P^1$ and $P^2$ are each independently hydrogen, methyl, ethyl, chloro, bromo or trifluoromethyl; and Q is the group —C(O)NHCH$_2$C(O)NHCH$_2$CF$_3$, —C(O)NHCH$_2$CF$_3$, —C(O)NHCF$_3$ or —C(O)NHCH$_2$CH$_2$SCH$_3$.

In one embodiment, the invention provides compounds of formula (I) wherein:

Y is Y-2 wherein $Z^3$ and $Z^4$ are N and $Z^1$, $Z^2$, $Z^5$ and $Z^6$ are C—H;

$B^1$, $B^2$ and $B^3$ are each independently N, C—H, C-halogen or C—$C_1$-$C_3$haloalkyl;

$R^1$ is $CF_3$;

$P^1$ and $P^2$ are each independently hydrogen, halogen, cyano, $C_1$-$C_8$alkyl, $C_1$-$C_8$haloalkyl or $C_3C_8$cycloalkyl; and Q is X—$NR^2R^3$ where $R^2$ is hydrogen and $R^3$ is alkyl optionally substituted by $R^4$.

In another embodiment, the invention provides compounds of formula (I) wherein:

Y is Y-2 wherein $Z^3$ and $Z^4$ are N and $Z^1$, $Z^2$, $Z^5$ and $Z^6$ are C—H;

$B^1$, $B^2$ and $B^3$ are each independently N, C—H, C-halogen or C—$C_1$-$C_3$haloalkyl;

$R^1$ is $CF_3$;

$P^1$ and $P^2$ are each independently hydrogen, halogen, cyano, $C_1$-$C_4$alkyl, $C_1$-$C_4$haloalkyl or $C_3C_8$cycloalkyl; and Q is X—$NR^2R^3$ where $R^2$ is hydrogen and $R^3$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylcarbonyl, alkoxycarbonyl, alkylaminocarbonyl, dialkylaminocarbonyl, haloalkylcarbonyl, haloalkoxycarbonyl, haloalkylaminocarbonyl or dihaloalkylaminocarbonyl.

In another embodiment, the invention provides compounds of formula (I) wherein:

Y is Y-2 wherein $Z^3$ and $Z^4$ are N and $Z^1$, $Z^2$, $Z^5$ and $Z^6$ are C—H;

$B^1$, $B^2$ and $B^3$ are each independently C—H, C—Cl, C—F or C—$CF_3$;

$R^1$ is $CF_3$;

$P^1$ and $P^2$ are each independently hydrogen, halogen, cyano, $C_1$-$C_4$alkyl, $C_1$-$C_4$haloalkyl or $C_3C_8$cycloalkyl; and Q is X—$NR^2R^3$ where $R^2$ is hydrogen and $R^3$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylcarbonyl, haloalkoxycarbonyl, haloalkylaminocarbonyl or dihaloalkylaminocarbonyl.

In another embodiment, the invention provides compounds of formula (I) wherein:

Y is Y-2 wherein $Z^3$ and $Z^4$ are N and $Z^1$, $Z^2$, $Z^5$ and $Z^6$ are C—H;

$B^1$, $B^2$ and $B^3$ are each independently C—H, C—Cl, C—F or C—$CF_3$;

$R^1$ is $CF_3$;

$P^1$ and $P^2$ are each independently hydrogen, halogen, cyano, $C_1$-$C_2$alkyl, $C_1$-$C_2$haloalkyl or $C_3C_8$cycloalkyl; and Q is the group —C(O)NHCH$_2$C(O)NHCH$_2$CF$_3$ or —C(O)NHCH$_2$CH$_2$SCH$_3$.

In another embodiment, the invention provides compounds of formula (I) wherein:

Y is Y-2 wherein $Z^3$ and $Z^4$ are N and $Z^1$, $Z^2$, $Z^5$ and $Z^6$ are C—H;

$B^1$ is C—Cl, $B^2$ is C—H or C—F, and $B^3$ is C—Cl or C—$CF_3$;

$R^1$ is $CF_3$;

$P^1$ and $P^2$ are each independently hydrogen, methyl, ethyl, chloro, bromo or trifluoromethyl; and Q is the group —C(O)NHCH$_2$C(O)NHCH$_2$CF$_3$, —C(O)NHCH$_2$CF$_3$, —C(O)NHCF$_3$ or —C(O)NHCH$_2$CH$_2$SCH$_3$.

In one embodiment, the invention provides compounds of formula (I) wherein:

Y is Y-2 wherein $Z^4$ and $Z^5$ are N and $Z^1$, $Z^2$, $Z^3$ and $Z^6$ are C—H;

$B^1$, $B^2$ and $B^3$ are each independently N, C—H, C-halogen or C—$C_1$-$C_3$haloalkyl;

$R^1$ is $CF_3$;

$P^1$ and $P^2$ are each independently hydrogen, halogen, cyano, $C_1$-$C_8$alkyl, $C_1$-$C_8$haloalkyl or $C_3C_8$cycloalkyl; and Q is X—$NR^2R^3$ where $R^2$ is hydrogen and $R^3$ is alkyl optionally substituted by $R^4$.

In another embodiment, the invention provides compounds of formula (I) wherein:

Y is Y-2 wherein $Z^4$ and $Z^5$ are N and $Z^1$, $Z^2$, $Z^3$ and $Z^6$ are C—H;

$B^1$, $B^2$ and $B^3$ are each independently N, C—H, C-halogen or C—$C_1$-$C_3$haloalkyl;

$R^1$ is $CF_3$;

$P^1$ and $P^2$ are each independently hydrogen, halogen, cyano, $C_1$-$C_4$alkyl, $C_1$-$C_4$haloalkyl or $C_3C_8$cycloalkyl; and Q is X—$NR^2R^3$ where $R^2$ is hydrogen and $R^3$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylcarbonyl, alkoxycarbonyl, alkylaminocarbonyl, dialkylaminocarbonyl, haloalkylcarbonyl, haloalkoxycarbonyl, haloalkylaminocarbonyl or dihaloalkylaminocarbonyl.

In another embodiment, the invention provides compounds of formula (I) wherein:

Y is Y-2 wherein $Z^4$ and $Z^5$ are N and $Z^1$, $Z^2$, $Z^3$ and $Z^6$ are C—H;

$B^1$, $B^2$ and $B^3$ are each independently C—H, C—Cl, C—F or C—$CF_3$;

$R^1$ is $CF_3$;

$P^1$ and $P^2$ are each independently hydrogen, halogen, cyano, $C_1$-$C_4$alkyl, $C_1$-$C_4$haloalkyl or $C_3C_8$cycloalkyl; and Q is X—$NR^2R^3$ where $R^2$ is hydrogen and $R^3$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylcarbonyl, haloalkoxycarbonyl, haloalkylaminocarbonyl or dihaloalkylaminocarbonyl.

In another embodiment, the invention provides compounds of formula (I) wherein:

Y is Y-2 wherein $Z^4$ and $Z^5$ are N and $Z^1$, $Z^2$, $Z^3$ and $Z^6$ are C—H;

$B^1$, $B^2$ and $B^3$ are each independently C—H, C—Cl, C—F or C—$CF_3$;

$R^1$ is $CF_3$;

$P^1$ and $P^2$ are each independently hydrogen, halogen, cyano, $C_1$-$C_2$alkyl, $C_1$-$C_2$haloalkyl or $C_3C_8$cycloalkyl; and Q is the group —C(O)$NHCH_2$C(O)$NHCH_2CF_3$ or —C(O)$NHCH_2CH_2SCH_3$.

In another embodiment, the invention provides compounds of formula (I) wherein:

Y is Y-2 wherein $Z^4$ and $Z^5$ are N and $Z^1$, $Z^2$, $Z^3$ and $Z^6$ are C—H;

$B^1$ is C—Cl, $B^2$ is C—H or C—F, and $B^3$ is C—Cl or C—$CF_3$;

$R^1$ is $CF_3$;

$P^1$ and $P^2$ are each independently hydrogen, methyl, ethyl, chloro, bromo or trifluoromethyl; and Q is the group —C(O)$NHCH_2$C(O)$NHCH_2CF_3$, —C(O)$NHCH_2CF_3$, —C(O)$NHCF_3$ or —C(O)$NHCH_2CH_2SCH_3$.

In one embodiment, the invention provides compounds of formula (I) wherein:

Y is Y-2 wherein $Z^5$ and $Z^6$ are N and $Z^1$ to $Z^4$ are C—H;

$B^1$, $B^2$ and $B^3$ are each independently N, C—H, C-halogen or C—$C_1$-$C_3$haloalkyl;

$R^1$ is $CF_3$;

$P^1$ and $P^2$ are each independently hydrogen, halogen, cyano, $C_1$-$C_8$alkyl, $C_1$-$C_8$haloalkyl or $C_3C_8$cycloalkyl; and Q is X—$NR^2R^3$ where $R^2$ is hydrogen and $R^3$ is alkyl optionally substituted by $R^4$.

In another embodiment, the invention provides compounds of formula (I) wherein:

Y is Y-2 wherein $Z^5$ and $Z^6$ are N and $Z^1$ to $Z^4$ are C—H;

$B^1$, $B^2$ and $B^3$ are each independently N, C—H, C-halogen or C—$C_1$-$C_3$haloalkyl;

$R^1$ is $CF_3$;

$P^1$ and $P^2$ are each independently hydrogen, halogen, cyano, $C_1$-$C_4$alkyl, $C_1$-$C_4$haloalkyl or $C_3C_8$cycloalkyl; and Q is X—$NR^2R^3$ where $R^2$ is hydrogen and $R^3$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylcarbonyl, alkoxycarbonyl, alkylaminocarbonyl, dialkylaminocarbonyl, haloalkylcarbonyl, haloalkoxycarbonyl, haloalkylaminocarbonyl or dihaloalkylaminocarbonyl.

In another embodiment, the invention provides compounds of formula (I) wherein:

Y is Y-2 wherein $Z^5$ and $Z^6$ are N and $Z^1$ to $Z^4$ are C—H;

$B^1$, $B^2$ and $B^3$ are each independently C—H, C—Cl, C—F or C—$CF_3$;

$R^1$ is $CF_3$;

$P^1$ and $P^2$ are each independently hydrogen, halogen, cyano, $C_1$-$C_4$alkyl, $C_1$-$C_4$haloalkyl or $C_3C_8$cycloalkyl; and Q is X—$NR^2R^3$ where $R^2$ is hydrogen and $R^3$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylcarbonyl, haloalkoxycarbonyl, haloalkylaminocarbonyl or dihaloalkylaminocarbonyl.

In another embodiment, the invention provides compounds of formula (I) wherein:

Y is Y-2 wherein $Z^5$ and $Z^6$ are N and $Z^1$ to $Z^4$ are C—H;

$B^1$, $B^2$ and $B^3$ are each independently C—H, C—Cl, C—F or C—$CF_3$;

$R^1$ is $CF_3$;

$P^1$ and $P^2$ are each independently hydrogen, halogen, cyano, $C_1$-$C_2$alkyl, $C_1$-$C_2$haloalkyl or $C_3C_8$cycloalkyl; and Q is the group —C(O)$NHCH_2$C(O)$NHCH_2CF_3$ or —C(O)$NHCH_2CH_2SCH_3$.

In another embodiment, the invention provides compounds of formula (I) wherein:

Y is Y-2 wherein $Z^5$ and $Z^6$ are N and $Z^1$ to $Z^4$ are C—H;

$B^1$ is C—Cl, $B^2$ is C—H or C—F, and $B^3$ is C—Cl or C—$CF_3$;

$R^1$ is $CF_3$;

$P^1$ and $P^2$ are each independently hydrogen, methyl, ethyl, chloro, bromo or trifluoromethyl; and Q is the group —C(O)$NHCH_2$C(O)$NHCH_2CF_3$, —C(O)$NHCH_2CF_3$, —C(O)$NHCF_3$ or —C(O)$NHCH_2CH_2SCH_3$.

In one embodiment, the invention provides compounds of formula (I) wherein:

Y is Y-3;

$B^1$, $B^2$ and $B^3$ are each independently N, C—H, C-halogen or C—$C_1$-$C_3$haloalkyl;

$R^1$ is $CF_3$;

$P^1$ and $P^2$ are each independently hydrogen, halogen, cyano, $C_1$-$C_8$alkyl, $C_1$-$C_8$haloalkyl or $C_3C_8$cycloalkyl; and Q is the group (—$CH_2$—)($CH_2$—)N—C(=O)$CH_2$S(O)$_2$$CH_3$.

For avoidance of doubt, the group (—$CH_2$—)($CH_2$—)N—C(=O)$CH_2$S(O)$_2$$CH_3$ corresponds to the group:

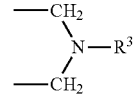

as described above for formula (I) where $R^3$ is C(=O)$CH_2$S(O)$_2CH_3$.

wherein each methylene group is bonded to a tetravalent atom of Y to form a spirocyclic group, In another embodiment, the invention provides compounds of formula (I) wherein:

Y is Y-3;

$B^1$ is C—Cl, $B^2$ is C—F and $B^3$ is C—Cl;

$R^1$ is $CF_3$;

$P^1$ and $P^2$ are each independently hydrogen, halogen, cyano, $C_1$-$C_2$alkyl, $C_1$-$C_2$haloalkyl or $C_3C_8$cycloalkyl; and Q is the group (—$CH_2$—)($CH_2$—)N—C(=O)$CH_2$S(O)$_2$$CH_3$.

In one embodiment, the invention provides compounds of formula (I) wherein:

Y is Y-4 where Z is C—H;

$B^1$, $B^2$ and $B^3$ are each independently N, C—H, C-halogen or C—$C_1$-$C_3$haloalkyl;

$R^1$ is $CF_3$;

$P^1$ and $P^2$ are each independently hydrogen, halogen, cyano, $C_1$-$C_8$alkyl, $C_1$-$C_8$haloalkyl or $C_3C_8$cycloalkyl; and Q is X—$NR^2R^3$ where $R^2$ is hydrogen and $R^3$ is alkyl optionally substituted by $R^4$.

In another embodiment, the invention provides compounds of formula (I) wherein:

Y is Y-4 where Z is C—H;

$B^1$, $B^2$ and $B^3$ are each independently N, C—H, C-halogen or C—$C_1$-$C_3$haloalkyl;

$R^1$ is $CF_3$;

$P^1$ and $P^2$ are each independently hydrogen, halogen, cyano, $C_1$-$C_4$alkyl, $C_1$-$C_4$haloalkyl or $C_3C_8$cycloalkyl; and Q is X—$NR^2R^3$ where $R^2$ is hydrogen and $R^3$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylcarbonyl, alkoxycarbonyl, alkylaminocarbonyl, dialkylaminocarbonyl, haloalkylcarbonyl, haloalkoxycarbonyl, haloalkylaminocarbonyl or dihaloalkylaminocarbonyl.

In another embodiment, the invention provides compounds of formula (I) wherein:

Y is Y-4 where Z is C—H;

$B^1$, $B^2$ and $B^3$ are each independently C—H, C—Cl, C—F or C—$CF_3$;

$R^1$ is $CF_3$;

$P^1$ and $P^2$ are each independently hydrogen, halogen, cyano, $C_1$-$C_4$alkyl, $C_1$-$C_4$haloalkyl or $C_3C_8$cycloalkyl; and Q is X—$NR^2R^3$ where $R^2$ is hydrogen and $R^3$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylcarbonyl, haloalkoxycarbonyl, haloalkylaminocarbonyl or dihaloalkylaminocarbonyl.

In another embodiment, the invention provides compounds of formula (I) wherein:

Y is Y-4 where Z is C—H;

$B^1$, $B^2$ and $B^3$ are each independently C—H, C—Cl, C—F or C—$CF_3$;

$R^1$ is $CF_3$;

$P^1$ and $P^2$ are each independently hydrogen, halogen, cyano, $C_1$-$C_2$alkyl, $C_1$-$C_2$haloalkyl or $C_3C_8$cycloalkyl; and Q is the group —C(O)NHCH$_2$C(O)NHCH$_2$CF$_3$ or —C(O)NHCH$_2$CH$_2$SCH$_3$.

In another embodiment, the invention provides compounds of formula (I) wherein:

Y is Y-4 where Z is C—H;

$B^1$ is C—Cl, $B^2$ is C—H or C—F, and $B^3$ is C—Cl or C—$CF_3$;

$R^1$ is $CF_3$;

$P^1$ and $P^2$ are each independently hydrogen, methyl, ethyl, chloro, bromo or trifluoromethyl; and Q is the group —C(O)NHCH$_2$C(O)NHCH$_2$CF$_3$, —C(O)NHCH$_2$CF$_3$, —C(O)NHCF$_3$ or —C(O)NHCH$_2$CH$_2$SCH$_3$.

In one embodiment, the invention provides compounds of formula (I) wherein:

Y is Y-4 where Z is N;

$B^1$, $B^2$ and $B^3$ are each independently N, C—H, C-halogen or C—$C_1$-$C_3$haloalkyl;

$R^1$ is $CF_3$;

$P^1$ and $P^2$ are each independently hydrogen, halogen, cyano, $C_1$-$C_8$alkyl, $C_1$-$C_8$haloalkyl or $C_3C_8$cycloalkyl; and Q is X—$NR^2R^3$ where $R^2$ is hydrogen and $R^3$ is alkyl optionally substituted by $R^4$.

In another embodiment, the invention provides compounds of formula (I) wherein:

Y is Y-4 where Z is N;

$B^1$, $B^2$ and $B^3$ are each independently N, C—H, C-halogen or C—$C_1$-$C_3$haloalkyl;

$R^1$ is $CF_3$;

$P^1$ and $P^2$ are each independently hydrogen, halogen, cyano, $C_1$-$C_4$alkyl, $C_1$-$C_4$haloalkyl or $C_3C_8$cycloalkyl; and Q is X—$NR^2R^3$ where $R^2$ is hydrogen and $R^3$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylcarbonyl, alkoxycarbonyl, alkylaminocarbonyl, dialkylaminocarbonyl, haloalkylcarbonyl, haloalkoxycarbonyl, haloalkylaminocarbonyl or dihaloalkylaminocarbonyl.

In another embodiment, the invention provides compounds of formula (I) wherein:

Y is Y-4 where Z is N;

$B^1$, $B^2$ and $B^3$ are each independently C—H, C—Cl, C—F or C—$CF_3$;

$R^1$ is $CF_3$;

$P^1$ and $P^2$ are each independently hydrogen, halogen, cyano, $C_1$-$C_4$alkyl, $C_1$-$C_4$haloalkyl or $C_3C_8$cycloalkyl; and Q is X—$NR^2R^3$ where $R^2$ is hydrogen and $R^3$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylcarbonyl, haloalkoxycarbonyl, haloalkylaminocarbonyl or dihaloalkylaminocarbonyl.

In another embodiment, the invention provides compounds of formula (I) wherein:

Y is Y-4 where Z is N;

$B^1$, $B^2$ and $B^3$ are each independently C—H, C—Cl, C—F or C—$CF_3$;

$R^1$ is $CF_3$;

$P^1$ and $P^2$ are each independently hydrogen, halogen, cyano, $C_1$-$C_2$alkyl, $C_1$-$C_2$haloalkyl or $C_3C_8$cycloalkyl; and Q is the group —C(O)NHCH$_2$C(O)NHCH$_2$CF$_3$ or —C(O)NHCH$_2$CH$_2$SCH$_3$.

In another embodiment, the invention provides compounds of formula (I) wherein:

Y is Y-4 where Z is N;

$B^1$ is C—Cl, $B^2$ is C—H or C—F, and $B^3$ is C—Cl or C—$CF_3$;

$R^1$ is $CF_3$;

$P^1$ and $P^2$ are each independently hydrogen, methyl, ethyl, chloro, bromo or trifluoromethyl; and Q is the group —C(O)NHCH$_2$C(O)NHCH$_2$CF$_3$, —C(O)NHCH$_2$CF$_3$, —C(O)NHCF$_3$ or —C(O)NHCH$_2$CH$_2$SCH$_3$.

In one embodiment, the invention provides compounds of formula (I) wherein:

Y is Y-5;

$B^1$, $B^2$ and $B^3$ are each independently N, C—H, C-halogen or C—$C_1$-$C_3$haloalkyl;

$R^1$ is $CF_3$;

$P^1$ and $P^2$ are each independently hydrogen, halogen, cyano, $C_1$-$C_8$alkyl, $C_1$-$C_8$haloalkyl or $C_3C_8$cycloalkyl; and Q is X—$NR^2R^3$ where $R^2$ is hydrogen and $R^3$ is alkyl optionally substituted by $R^4$.

In another embodiment, the invention provides compounds of formula (I) wherein:

Y is Y-5;

$B^1$, $B^2$ and $B^3$ are each independently N, C—H, C-halogen or C—$C_1$-$C_3$haloalkyl;

$R^1$ is $CF_3$;

$P^1$ and $P^2$ are each independently hydrogen, halogen, cyano, $C_1$-$C_4$alkyl, $C_1$-$C_4$haloalkyl or $C_3C_8$cycloalkyl; and Q is X—$NR^2R^3$ where $R^2$ is hydrogen and $R^3$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylcarbonyl, alkoxycarbonyl, alkylaminocarbonyl, dialkylaminocarbonyl, haloalkylcarbonyl, haloalkoxycarbonyl, haloalkylaminocarbonyl or dihaloalkylaminocarbonyl.

In another embodiment, the invention provides compounds of formula (I) wherein:
Y is Y-5;
$B^1$, $B^2$ and $B^3$ are each independently C—H, C—Cl, C—F or C—$CF_3$;
$R^1$ is $CF_3$;
$P^1$ and $P^2$ are each independently hydrogen, halogen, cyano, $C_1$-$C_4$alkyl, $C_1$-$C_4$haloalkyl or $C_3C_8$cycloalkyl; and
Q is X—$NR^2R^3$ where $R^2$ is hydrogen and $R^3$ is $C_1$-$C_3$alkyl optionally substituted by halogen, alkylthio, haloalkylthio, alkylsulfinyl, haloalkylsulfinyl, alkylsulfonyl, haloalkylsulfonyl, alkylaminocarbonyl, dialkylaminocarbonyl, haloalkylcarbonyl, haloalkoxycarbonyl, haloalkylaminocarbonyl or dihaloalkylaminocarbonyl.

In another embodiment, the invention provides compounds of formula (I) wherein:
Y is Y-5;
$B^1$, $B^2$ and $B^3$ are each independently C—H, C—Cl, C—F or C—$CF_3$;
$R^1$ is $CF_3$;
$P^1$ and $P^2$ are each independently hydrogen, halogen, cyano, $C_1$-$C_2$alkyl, $C_1$-$C_2$haloalkyl or $C_3C_8$cycloalkyl; and
Q is the group —C(O)NHCH$_2$C(O)NHCH$_2$CF$_3$ or —C(O)NHCH$_2$CH$_2$SCH$_3$.

In another embodiment, the invention provides compounds of formula (I) wherein:
Y is Y-5;
$B^1$, $B^2$ and $B^3$ are each C—Cl;
$R^1$ is $CF_3$;
$P^1$ and $P^2$ are each independently hydrogen, methyl, ethyl, chloro, bromo or trifluoromethyl; and
Q is the group —C(O)NHCH$_2$C(O)NHCH$_2$CF$_3$, —C(O)NHCH$_2$CF$_3$, —C(O)NHCF$_3$ or —C(O)NHCH$_2$CH$_2$SCH$_3$.

In one embodiment, the invention provides compounds of formula (I) wherein:
Y is Y-6;
$B^1$, $B^2$ and $B^3$ are each independently N, C—H, C-halogen or C—$C_1$-$C_3$haloalkyl;
$R^1$ is $CF_3$;
$P^1$ and $P^2$ are each independently hydrogen, halogen, cyano, $C_1$-$C_8$alkyl, $C_1$-$C_8$haloalkyl or $C_3C_8$cycloalkyl; and
Q is OH, alkoxy, haloalkoxy, alkylamino, haloalkylamino, dialkylamino or dihaloalkylamino.

In another embodiment, the invention provides compounds of formula (I) wherein:
Y is Y-6;
$B^1$, $B^2$ and $B^3$ are each independently N, C—H, C-halogen or C—$C_1$-$C_3$haloalkyl;
$R^1$ is $CF_3$;
$P^1$ and $P^2$ are each independently hydrogen, halogen, cyano, $C_1$-$C_4$alkyl, $C_1$-$C_4$haloalkyl or $C_3C_8$cycloalkyl; and
Q is OH, alkoxy or haloalkoxy.

In another embodiment, the invention provides compounds of formula (I) wherein:
Y is Y-6;
$B^1$, $B^2$ and $B^3$ are each independently C—H, C—Cl, C—F or C—$CF_3$;
$R^1$ is $CF_3$;
$P^1$ and $P^2$ are each independently hydrogen, halogen, cyano, $C_1$-$C_2$alkyl, $C_1$-$C_2$haloalkyl or $C_3C_8$cycloalkyl; and
Q is OH, $C_1$-$C_3$alkoxy or $C_1$-$C_3$haloalkoxy.

In another embodiment, the invention provides compounds of formula (I) wherein:
Y is Y-6;
$B^1$, $B^2$ and $B^3$ are each independently C—H, C—Cl, C—F or C—$CF_3$;
$R^1$ is $CF_3$;
$P^1$ and $P^2$ are each independently hydrogen, methyl, ethyl, chloro, bromo or trifluoromethyl; and
Q is OH.

In another embodiment, the invention provides compounds of formula (I) wherein:
Y is Y-6;
$B^1$, $B^2$ and $B^3$ are each C—Cl;
$R^1$ is $CF_3$;
$P^1$ and $P^2$ are each independently hydrogen, methyl, ethyl, chloro, bromo or trifluoromethyl; and
Q is OH.

In several embodiments, the invention provides compounds of formula (I) wherein Y is Y-1; $B^1$, $B^2$, $B^3$, $R^1$, $P^1$ and $P^2$ are as defined above for formula (I), and Q is as defined in Table 1 below:

TABLE 1

| # | Q |
|---|---|
| 1 | Ethyl |
| 2 | 2,2,2-trifluoro-ethyl |
| 3 | prop-2-yl |
| 4 | Methyl |
| 5 | 2-fluoro-cycloprop-1-yl |
| 6 | prop-1-yl |
| 7 | 2-fluoro-ethyl |
| 8 | 2-cyano-ethyl |
| 9 | 1-fluoroethyl |
| 10 | 2-methylprop-1-yl |
| 11 | Cyclopropylmethyl |
| 12 | 2-methoxy-ethyl |
| 13 | 3-methyloxetan-3-yl |
| 14 | 1-methylcyclopropyl |
| 15 | dihydrofuran-4-yl |
| 16 | Cyclopropyl |
| 17 | Cyclobutyl |
| 18 | Methylsulfonylmethyl |
| 19 | propen-1-yl |
| 20 | Methylsulfanylmethyl |
| 21 | 1-methoxyeth-1-yl |
| 22 | 5-pyrimidyl |
| 23 | but-2-yl |
| 24 | 1-fluoroprop-2-yl |
| 25 | 2-methylpropen-1-yl |
| 26 | 1-cyanocyclopropyl |
| 27 | N-formylaminomethyl |
| 28 | 2-methylsulfinyl-ethyl |
| 29 | 2-(methylsulfonyl)-ethyl |
| 30 | 1-oxo-tetrahydrofuran-3-yl |
| 31 | 1-oxo-thietan-3-yl |
| 32 | 1,1-dioxo-tetrahydrofuran-3-yl |
| 33 | 1,1-dioxo-thietan-3-yl |
| 34 | 3-chloroprop-1-yl |
| 35 | 3,3,3-trifluoro-propyl |
| 36 | thietan-3-yl |
| 37 | tetrahydrofuran-2-yl |
| 38 | 1,1,1-trifluoroprop-2-yl |
| 39 | but-1-yl |
| 40 | 2,2-difluoro-ethyl |
| 41 | OH |
| 42 | Methoxy |
| 43 | Ethoxy |
| 44 | (—CH$_2$—)(—CH$_2$—)N—C(=O)CH$_2$S(O)$_2$CH$_3$ |

The invention also provides compounds of formula (I) which are described in Tables 2 to 7 below:

Table 2: The invention provides compounds of formula (I) wherein Y is Y-2; $B^1$, $B^2$, $B^3$, $R^1$, $P^1$ and $P^2$ are as defined above for formula (I), and Q is as defined in Table 1 above.

Table 3: The invention provides compounds of formula (I) wherein Y is Y-3 and $B^1$, $B^2$, $B^3$, $R^1$, $P^1$ and $P^2$ are as defined above; Q is as defined in Table 1 above, and wherein the other group bonded to the carbon atom to which Q is bonded is hydrogen, $C_1$-$C_3$alkyl or $C_1$-$C_3$haloalkyl.

Table 4: The invention provides compounds of formula (I) wherein Y is Y-4 and Z is C—H; $B^1$, $B^2$, $B^3$, $R^1$, $P^1$ and $P^2$ are as defined above for formula (I), and Q is as defined in Table 1 above.

Table 5: The invention provides compounds of formula (I) wherein Y is Y-4 and Z is N; $B^1$, $B^2$, $B^3$, $R^1$, $P^1$ and $P^2$ are as defined above for formula (I), and Q is as defined in Table 1 above.

Table 6: The invention provides compounds of formula (I) wherein Y is Y-5; $B^1$, $B^2$, $B^3$, $R^1$, $P^1$ and $P^2$ are as defined above for formula (I), and Q is as defined in Table 1 above.

Table 7: The invention provides compounds of formula (I) wherein Y is Y-6; $B^1$, $B^2$, $B^3$, $R^1$, $P^1$ and $P^2$ are as defined above for formula (I), and Q is as defined in Table 1 above.

The invention further provides compounds of formula (I) described in Tables 8 to 15 below:

Table 8: The present invention provides compounds of formula (I), wherein Y is Y-1, $B^1$, $B^2$, $B^3$, $R^1$, $P^1$ and $P^2$ are as defined above for formula (I), and Q is X—$NR^2R^3$ where X is C(=O) or C(=S), $R^2$ is H or $C_1$-$C_3$alkyl, and $R^3$ is as defined in Table 1 above.

Table 9: The present invention provides compounds of formula (I), wherein Y is Y-2, $B^1$, $B^2$, $B^3$, $R^1$, $P^1$ and $P^2$ are as defined above for formula (I), and Q is X—$NR^2R^3$ where X is C(=O) or C(=S), $R^2$ is H or $C_1$-$C_3$alkyl, and $R^3$ is as defined in Table 1 above.

Table 10: The present invention provides compounds of formula (I), wherein Y is Y-2, $B^1$, $B^2$, $B^3$, $R^1$, $P^1$ and $P^2$ are as defined above for formula (I), and Q is X—$NR^2R^3$ where X is C(=O) or C(=S), $R^2$ is H or $C_1$-$C_3$alkyl, and $R^3$ is as defined in Table 1 above.

Table 11: The present invention provides compounds of formula (I), wherein Y is Y-3, $B^1$, $B^2$, $B^3$, $R^1$, $P^1$ and $P^2$ are as defined above for formula (I), and Q is X—$NR^2R^3$ where X is C(=O) or C(=S), $R^2$ is H or $C_1$-$C_3$alkyl, $R^3$ is as defined in Table 1 above, and wherein the other group bonded to the carbon atom to which Q is bonded is hydrogen, $C_1$-$C_3$alkyl or $C_1$-$C_3$haloalkyl.

Table 12: The present invention provides compounds of formula (I), wherein Y is Y-4 where Z is C—H, $B^1$, $B^2$, $B^3$, $R^1$, $P^1$ and $P^2$ are as defined above for formula (I), and Q is X—$NR^2R^3$ where X is C(=O) or C(=S), $R^2$ is H or $C_1$-$C_3$alkyl, and $R^3$ is as defined in Table 1 above.

Table 13: The present invention provides compounds of formula (I), wherein Y is Y-4 where Z is N, $B^1$, $B^2$, $B^3$, $R^1$, $P^1$ and $P^2$ are as defined above for formula (I), and Q is X—$NR^2R^3$ where X is C(=O) or C(=S), $R^2$ is H or $C_1$-$C_3$alkyl, and $R^3$ is as defined in Table 1 above.

Table 14: The present invention provides compounds of formula (I), wherein Y is Y-5, $B^1$, $B^2$, $B^3$, $R^1$, $P^1$ and $P^2$ are as defined above for formula (I), and Q is X—$NR^2R^3$ where X is C(=O) or C(=S), $R^2$ is H or $C_1$-$C_3$alkyl, and $R^3$ is as defined in Table 1 above.

Table 15: The present invention provides compounds of formula (I), wherein Y is Y-6, $B^1$, $B^2$, $B^3$, $R^1$, $P^1$ and $P^2$ are as defined above for formula (I), and Q is X—$NR^2R^3$ where X is C(=O) or C(=S), $R^2$ is H or $C_1$-$C_3$alkyl, and $R^3$ is as defined in Table 1 above.

The invention further provides compounds of formula (I) as described in Tables 16 to 22 below:

Table 16: The present invention provides compounds of formula (I), wherein Y is Y-1, $B^1$, $B^2$, $B^3$, $R^1$, $P^1$ and $P^2$ are as defined above for formula (I), and Q is T1 where $R^2$ is H or $C_1$-$C_3$alkyl, and $R^3$ is as defined in Table 1 above.

Table 17: The present invention provides compounds of formula (I), wherein Y is Y-2, $B^1$, $B^2$, $B^3$, $R^1$, $P^1$ and $P^2$ are as defined above for formula (I), and Q is T1 where $R^2$ is H or $C_1$-$C_3$alkyl, and $R^3$ is as defined in Table 1 above.

Table 18: The present invention provides compounds of formula (I), wherein Y is Y-3, $B^1$, $B^2$, $B^3$, $R^1$, $P^1$ and $P^2$ are as defined above for formula (I), and Q is T1 where $R^2$ is H or $C_1$-$C_3$alkyl, and $R^3$ is as defined in Table 1 above, and wherein the other group bonded to the carbon atom to which Q is bonded is hydrogen, $C_1$-$C_3$alkyl or $C_1$-$C_3$haloalkyl.

Table 19: The present invention provides compounds of formula (I), wherein Y is Y-4 and Z is C—H; $B^1$, $B^2$, $B^3$, $R^1$, $P^1$ and $P^2$ are as defined above for formula (I), and Q is T1 where $R^2$ is H or $C_1$-$C_3$alkyl, and $R^3$ is as defined in Table 1 above.

Table 20: the present invention provides compounds of formula (I), wherein Y is Y-4 where Z is N; $B^1$, $B^2$, $B^3$, $R^1$, $P^1$ and $P^2$ are as defined above for formula (I), and Q is T1 where $R^2$ is H or $C_1$-$C_3$alkyl, and $R^3$ is as defined in Table 1 above.

Table 21: the present invention provides compounds of formula (I), wherein Y is Y-5, $B^1$, $B^2$, $B^3$, $R^1$, $P^1$ and $P^2$ are as defined above for formula (I), and Q is T1 where $R^2$ is H or $C_1$-$C_3$alkyl, and $R^3$ is as defined in Table 1 above.

Table 22: the present invention provides compounds of formula (I), wherein Y is Y-6, $B^1$, $B^2$, $B^3$, $R^1$, $P^1$ and $P^2$ are as defined above for formula (I), and Q is T1 where $R^2$ is H or $C_1$-$C_3$alkyl, and $R^3$ is as defined in Table 1 above.

The invention further provides compounds of formula (I) as described in Tables 23-36 below:

Table 23: The present invention provides compounds of formula (I), wherein Y is Y-1, $B^1$, $B^2$, $B^3$, $R^1$, $P^1$ and $P^2$ are as defined above for formula (I), and Q is T2 where $R^2$ is H or $C_1$-$C_3$alkyl, and $R^3$ is as defined in Table 1 above.

Table 24: The present invention provides compounds of formula (I), wherein Y is Y-2, $B^1$, $B^2$, $B^3$, $R^1$, $P^1$ and $P^2$ are as defined above for formula (I), and Q is T2 where $R^2$ is H or $C_1$-$C_3$alkyl, and $R^3$ is as defined in Table 1 above.

Table 25: The present invention provides compounds of formula (I), wherein Y is Y-3, $B^1$, $B^2$, $B^3$, $R^1$, $P^1$ and $P^2$ are as defined above for formula (I), and Q is T2 where $R^2$ is H or $C_1$-$C_3$alkyl, and $R^3$ is as defined in Table 1 above, and wherein the other group bonded to the carbon atom to which Q is bonded is hydrogen, $C_1$-$C_3$alkyl or $C_1$-$C_3$haloalkyl.

Table 26: The present invention provides compounds of formula (I), wherein Y is Y-4 where Z is C—H, $B^1$, $B^2$, $B^3$, $R^1$, $P^1$ and $P^2$ are as defined above for formula (I), and Q is T2 where $R^2$ is H or $C_1$-$C_3$alkyl, and $R^3$ is as defined in Table 1 above.

Table 27: The present invention provides compounds of formula (I), wherein Y is Y-4 where Z is N, $B^1$, $B^2$, $B^3$, $R^1$, $P^1$ and $P^2$ are as defined above for formula (I), and Q is T2 where $R^2$ is H or $C_1$-$C_3$alkyl, and $R^3$ is as defined in Table 1 above.

Table 28: The present invention provides compounds of formula (I), wherein Y is Y-5, $B^1$, $B^2$, $B^3$, $R^1$, $P^1$ and $P^2$ are as defined above for formula (I), and Q is T2 where $R^2$ is H or $C_1$-$C_3$alkyl, and $R^3$ is as defined in Table 1 above.

Table 29: The present invention provides compounds of formula (I), wherein Y is Y-6, $B^1$, $B^2$, $B^3$, $R^1$, $P^1$ and $P^2$ are as defined above for formula (I), and Q is T2 where $R^2$ is H or $C_1$-$C_3$alkyl, and $R^3$ is as defined in Table 1 above.

Table 30: The invention provides compounds of formula (I) wherein Y is Y-1 and $B^1$, $B^2$, $B^3$ are each independently C—H, C—Cl, C—F or C—$CF_3$; $R^1$ is $CF_3$; $P^1$ and $P^2$ are each independently hydrogen, halogen, cyano, $C_1$-$C_2$alkyl, $C_1$-$C_2$haloalkyl or $C_3C_8$cycloalkyl, and Q is as defined in Table 1 above:

Table 31: The invention provides compounds of formula (I) wherein Y is Y-2 and $B^1$, $B^2$, $B^3$ are each independently C—H, C—Cl, C—F or C—$CF_3$; $R^1$ is $CF_3$, $P^1$ and $P^2$ are each independently hydrogen, halogen, cyano, $C_1$-$C_2$alkyl, $C_1$-$C_2$haloalkyl or $C_3C_8$cycloalkyl, and Q is as defined in Table 1 above.

Table 32: The invention provides compounds of formula (I) wherein Y is Y-3 and $B^1$, $B^2$, $B^3$ are each independently C—H, C—Cl, C—F or C—$CF_3$; $R^1$ is $CF_3$, $P^1$ and $P^2$ are each independently hydrogen, halogen, cyano, $C_1$-$C_2$alkyl, $C_1$-$C_2$haloalkyl or $C_3C_8$cycloalkyl; Q is as defined in Table 1 above, and wherein the other group bonded to the carbon atom to which Q is bonded is hydrogen, $C_1$-$C_3$alkyl or $C_1$-$C_3$haloalkyl.

Table 33: The invention provides compounds of formula (I) wherein Y is Y-4 and Z is C—H; $B^1$, $B^2$, $B^3$ are each independently C—H, C—Cl, C—F or C—$CF_3$; $R^1$ is $CF_3$, $P^1$ and $P^2$ are each independently hydrogen, halogen, cyano, $C_1$-$C_2$alkyl, $C_1$-$C_2$haloalkyl or $C_3C_8$cycloalkyl, and Q is as defined in Table 1 above.

Table 34: The invention provides compounds of formula (I) wherein Y is Y-4 and Z is N; $B^1$, $B^2$, $B^3$ are each independently C—H, C—Cl, C—F or C—$CF_3$; $R^1$ is $CF_3$, $P^1$ and $P^2$ are each independently hydrogen, halogen, cyano, $C_1$-$C_2$alkyl, $C_1$-$C_2$haloalkyl or $C_3C_8$cycloalkyl, and Q is as defined in Table 1 above.

Table 35: The invention provides compounds of formula (I) wherein Y is Y-5; $B^1$, $B^2$, $B^3$ are each independently C—H, C—Cl, C—F or C—$CF_3$; $R^1$ is $CF_3$, $P^1$ and $P^2$ are each independently hydrogen, halogen, cyano, $C_1$-$C_2$alkyl, $C_1$-$C_2$haloalkyl or $C_3C_8$cycloalkyl, and Q is as defined in Table 1 above.

Table 36: The invention provides compounds of formula (I) wherein Y is Y-6; $B^1$, $B^2$, $B^3$ are each independently C—H, C—Cl, C—F or C—$CF_3$; $R^1$ is $CF_3$, $P^1$ and $P^2$ are each independently hydrogen, halogen, cyano, $C_1$-$C_2$alkyl, $C_1$-$C_2$haloalkyl or $C_3C_8$cycloalkyl, and Q is as defined in Table 1 above.

The invention further provides compounds of formula (I) as described in Tables 37 to 43 below:

Table 37: The present invention provides compounds of formula (I), wherein Y is Y-1, $B^1$, $B^2$, $B^3$ are each independently C—H, C—Cl, C—F or C—$CF_3$; $R^1$ is $CF_3$, $P^1$ and $P^2$ are each independently hydrogen, halogen, cyano, $C_1$-$C_2$alkyl, $C_1$-$C_2$haloalkyl or $C_3C_8$cycloalkyl, and Q is X—$NR^2R^3$ where X is C(=O) or C(=S), $R^2$ is H or $C_1$-$C_3$alkyl, and $R^3$ is as defined in Table 1 above.

Table 38: The present invention provides compounds of formula (I), wherein Y is Y-2, $B^1$, $B^2$, $B^3$ are each independently C—H, C—Cl, C—F or C—$CF_3$; $R^1$ is $CF_3$, $P^1$ and $P^2$ are each independently hydrogen, halogen, cyano, $C_1$-$C_2$alkyl, $C_1$-$C_2$haloalkyl or $C_3C_8$cycloalkyl, and Q is X—$NR^2R^3$ where X is C(=O) or C(=S), $R^2$ is H or $C_1$-$C_3$alkyl, and $R^3$ is as defined in Table 1 above.

Table 39: The present invention provides compounds of formula (I), wherein Y is Y-3, $B^1$, $B^2$, $B^3$ are each independently C—H, C—Cl, C—F or C—$CF_3$; $R^1$ is $CF_3$, $P^1$ and $P^2$ are each independently hydrogen, halogen, cyano, $C_1$-$C_2$alkyl, $C_1$-$C_2$haloalkyl or $C_3C_8$cycloalkyl, and Q is X—$NR^2R^3$ where X is C(=O) or C(=S), $R^2$ is H or $C_1$-$C_3$alkyl, $R^3$ is as defined in Table 1 above, and wherein the other group bonded to the carbon atom to which Q is bonded is hydrogen, $C_1$-$C_3$alkyl or $C_1$-$C_3$haloalkyl.

Table 40: The present invention provides compounds of formula (I), wherein Y is Y-4 where Z is C—H, $B^1$, $B^2$, $B^3$ are each independently C—H, C—Cl, C—F or C—$CF_3$; $R^1$ is $CF_3$, $P^1$ and $P^2$ are each independently hydrogen, halogen, cyano, $C_1$-$C_2$alkyl, $C_1$-$C_2$haloalkyl or $C_3C_8$cycloalkyl, and Q is X—$NR^2R^3$ where X is C(=O) or C(=S), $R^2$ is H or $C_1$-$C_3$alkyl, and $R^3$ is as defined in Table 1 above.

Table 41: The present invention provides compounds of formula (I), wherein Y is Y-4 where Z is N, $B^1$, $B^2$, $B^3$ are each independently C—H, C—Cl, C—F or C—$CF_3$; $R^1$ is $CF_3$, $P^1$ and $P^2$ are each independently hydrogen, halogen, cyano, $C_1$-$C_2$alkyl, $C_1$-$C_2$haloalkyl or $C_3C_8$cycloalkyl, and Q is X—$NR^2R^3$ where X is C(=O) or C(=S), $R^2$ is H or $C_1$-$C_3$alkyl, and $R^3$ is as defined in Table 1 above.

Table 42: The present invention provides compounds of formula (I), wherein Y is Y-5, $B^1$, $B^2$, $B^3$ are each independently C—H, C—Cl, C—F or C—$CF_3$; $R^1$ is $CF_3$, $P^1$ and $P^2$ are each independently hydrogen, halogen, cyano, $C_1$-$C_2$alkyl, $C_1$-$C_2$haloalkyl or $C_3C_8$cycloalkyl, and Q is X—$NR^2R^3$ where X is C(=O) or C(=S), $R^2$ is H or $C_1$-$C_3$alkyl, and $R^3$ is as defined in Table 1 above.

Table 43: The present invention provides compounds of formula (I), wherein Y is Y-6, $B^1$, $B^2$, $B^3$ are each independently C—H, C—Cl, C—F or C—$CF_3$; $R^1$ is $CF_3$, $P^1$ and $P^2$ are each independently hydrogen, halogen, cyano, $C_1$-$C_2$alkyl, $C_1$-$C_2$haloalkyl or $C_3C_8$cycloalkyl, and Q is X—$NR^2R^3$ where X is C(=O) or C(=S), $R^2$ is H or $C_1$-$C_3$alkyl, and $R^3$ is as defined in Table 1 above.

The invention further provides compounds of formula (I) as described in Tables 44-50 below:

Table 44: The present invention provides compounds of formula (I), wherein Y is Y-1, $B^1$, $B^2$, $B^3$ are each independently C—H, C—Cl, C—F or C—$CF_3$; $R^1$ is $CF_3$, $P^1$ and $P^2$ are each independently hydrogen, halogen, cyano, $C_1$-$C_2$alkyl, $C_1$-$C_2$haloalkyl or $C_3C_8$cycloalkyl, and Q is T1 where $R^2$ is H or $C_1$-$C_3$alkyl, and $R^3$ is as defined in Table 1 above.

Table 45: The present invention provides compounds of formula (I), wherein Y is Y-2, $B^1$, $B^2$, $B^3$ are each independently C—H, C—Cl, C—F or C—$CF_3$; $R^1$ is $CF_3$, $P^1$ and $P^2$ are each independently hydrogen, halogen, cyano, $C_1$-$C_2$alkyl, $C_1$-$C_2$haloalkyl or $C_3C_8$cycloalkyl, and Q is T1 where $R^2$ is H or $C_1$-$C_3$alkyl, and $R^3$ is as defined in Table 1 above.

Table 46: The present invention provides compounds of formula (I), wherein Y is Y-3, $B^1$, $B^2$, $B^3$ are each independently C—H, C—Cl, C—F or C—$CF_3$; $R^1$ is $CF_3$, $P^1$ and $P^2$ are each independently hydrogen, halogen, cyano, $C_1$-$C_2$alkyl, $C_1$-$C_2$haloalkyl or $C_3C_8$cycloalkyl, and Q is T1 where $R^2$ is H or $C_1$-$C_3$alkyl, and $R^3$ is as defined in Table 1 above, and wherein the other group bonded to the carbon atom to which Q is bonded is hydrogen, $C_1$-$C_3$alkyl or $C_1$-$C_3$haloalkyl.

Table 47: The present invention provides compounds of formula (I), wherein Y is Y-4 where Z is C—H, $B^1$, $B^2$, $B^3$ are each independently C—H, C—Cl, C—F or C—$CF_3$; $R^1$ is $CF_3$, $P^1$ and $P^2$ are each independently hydrogen, halogen, cyano, $C_1$-$C_2$alkyl, $C_1$-$C_2$haloalkyl or $C_3C_8$cycloalkyl, and Q is T1 where $R^2$ is H or $C_1$-$C_3$alkyl, and $R^3$ is as defined in Table 1 above.

Table 48: The present invention provides compounds of formula (I), wherein Y is Y-4 where Z is N, $B^1$, $B^2$, $B^3$ are each independently C—H, C—Cl, C—F or C—$CF_3$; $R^1$ is $CF_3$, $P^1$ and $P^2$ are each independently hydrogen, halogen, cyano, $C_1$-$C_2$alkyl, $C_1$-$C_2$haloalkyl or $C_3C_8$cycloalkyl, and Q is T1 where $R^2$ is H or $C_1$-$C_3$alkyl, and $R^3$ is as defined in Table 1 above.

In Table 49, the present invention provides compounds of formula (I), wherein Y is Y-5, $B^1$, $B^2$, $B^3$ are each independently C—H, C—Cl, C—F or C—$CF_3$; $R^1$ is $CF_3$, $P^1$ and $P^2$ are each independently hydrogen, halogen, cyano, $C_1$-$C_2$alkyl, $C_1$-$C_2$haloalkyl or $C_3C_8$cycloalkyl, and Q is T1 where $R^2$ is H or $C_1$-$C_3$alkyl, and $R^3$ is as defined in Table 1 above.

Table 50: The present invention provides compounds of formula (I), wherein Y is Y-6, $B^1$, $B^2$, $B^3$ are each independently C—H, C—Cl, C—F or C—$CF_3$; $R^1$ is $CF_3$, $P^1$ and $P^2$ are each independently hydrogen, halogen, cyano, $C_1$-$C_2$alkyl, $C_1$-$C_2$haloalkyl or $C_3C_8$cycloalkyl, and Q is T1 where $R^2$ is H or $C_1$-$C_3$alkyl, and $R^3$ is as defined in Table 1 above.

The invention further provides the compounds of formula (I) as described in Tables 51-57 below:

Table 51: The present invention provides compounds of formula (I), wherein Y is Y-1, $B^1$, $B^2$, $B^3$ are each independently C—H, C—Cl, C—F or C—$CF_3$; $R^1$ is $CF_3$, $P^1$ and $P^2$ are each independently hydrogen, halogen, cyano, $C_1$-$C_2$alkyl, $C_1$-$C_2$haloalkyl or $C_3C_8$cycloalkyl, and Q is T2 where $R^2$ is H or $C_1$-$C_3$alkyl, and $R^3$ is as defined in Table 1 above.

Table 52: The present invention provides compounds of formula (I), wherein Y is Y-2, $B^1$, $B^2$, $B^3$ are each independently C—H, C—Cl, C—F or C—$CF_3$; $R^1$ is $CF_3$, $P^1$ and $P^2$ are each independently hydrogen, halogen, cyano, $C_1$-$C_2$alkyl, $C_1$-$C_2$haloalkyl or $C_3C_8$cycloalkyl, and Q is T2 where $R^2$ is H or $C_1$-$C_3$alkyl, and $R^3$ is as defined in Table 1 above.

Table 53: The present invention provides compounds of formula (I), wherein Y is Y-3, $B^1$, $B^2$, $B^3$ are each independently C—H, C—Cl, C—F or C—$CF_3$; $R^1$ is $CF_3$, $P^1$ and $P^2$ are each independently hydrogen, halogen, cyano, $C_1$-$C_2$alkyl, $C_1$-$C_2$haloalkyl or $C_3C_8$cycloalkyl, and Q is T2 where $R^2$ is H or $C_1$-$C_3$alkyl, and $R^3$ is as defined in Table 1 above, and wherein the other group bonded to the carbon atom to which Q is bonded is hydrogen, $C_1$-$C_3$alkyl or $C_1$-$C_3$haloalkyl.

Table 54: The present invention provides compounds of formula (I), wherein Y is Y-4 where Z is C—H, $B^1$, $B^2$, $B^3$ are each independently C—H, C—Cl, C—F or C—$CF_3$; $R^1$ is $CF_3$, $P^1$ and $P^2$ are each independently hydrogen, halogen, cyano, $C_1$-$C_2$alkyl, $C_1$-$C_2$haloalkyl or $C_3C_8$cycloalkyl, and Q is T2 where $R^2$ is H or $C_1$-$C_3$alkyl, and $R^3$ is as defined in Table 1 above.

Table 55: The present invention provides compounds of formula (I), wherein Y is Y-4 where Z is N, $B^1$, $B^2$, $B^3$ are each independently C—H, C—Cl, C—F or C—$CF_3$; $R^1$ is $CF_3$, $P^1$ and $P^2$ are each independently hydrogen, halogen, cyano, $C_1$-$C_2$alkyl, $C_1$-$C_2$haloalkyl or $C_3C_8$cycloalkyl, and Q is T2 where $R^2$ is H or $C_1$-$C_3$alkyl, and $R^3$ is as defined in Table 1 above.

Table 56: The present invention provides compounds of formula (I), wherein Y is Y-5, $B^1$, $B^2$, $B^3$ are each independently C—H, C—Cl, C—F or C—$CF_3$; $R^1$ is $CF_3$, $P^1$ and $P^2$ are each independently hydrogen, halogen, cyano, $C_1$-$C_2$alkyl, $C_1$-$C_2$haloalkyl or $C_3C_8$cycloalkyl, and Q is T2 where $R^2$ is H or $C_1$-$C_3$alkyl, and $R^3$ is as defined in Table 1 above.

Table 58: The present invention provides compounds of formula (I), wherein Y is Y-6, $B^1$, $B^2$, $B^3$ are each independently C—H, C—Cl, C—F or C—$CF_3$; $R^1$ is $CF_3$, $P^1$ and $P^2$ are each independently hydrogen, halogen, cyano, $C_1$-$C_2$alkyl, $C_1$-$C_2$haloalkyl or $C_3C_8$cycloalkyl, and Q is T2 where $R^2$ is H or $C_1$-$C_3$alkyl, and $R^3$ is as defined in Table 1 above.

Stereoisomers and Polymorphic Forms

It will be appreciated by those of skill in the art that the compounds of the invention may exist and be isolated as optically active and racemic forms. Compounds having one or more chiral centers, including that at a sulfur atom, may be present as single enantiomers or diastereomers or as mixtures of enantiomers and/or diastereomers. For example, it is well known in the art that sulfoxide compounds may be optically active and may exist as single enantiomers or racemic mixtures. In addition, compounds of the invention may include one or more chiral centers, which results in a theoretical number of optically active isomers. Where compounds of the invention include n chiral centers, the compounds may comprise up to $2^n$ optical isomers. The present invention encompasses the specific enantiomers or diastereomers of each compound as well as mixtures of different enantiomers and/or diastereomers of the compounds of the invention that possess the useful properties described herein. The optically active forms can be prepared by, for example, resolution of the racemic forms by selective crystallization techniques, by synthesis from optically active precursors, by chiral synthesis, by chromatographic separation using a chiral stationary phase or by enzymatic resolution.

The compounds of present invention may also be present in different solid forms such as different crystalline forms or in the form of an amorphous solid. The present invention encompasses different crystalline forms as well as amorphous forms of the inventive compounds.

In addition, the compounds of the invention may exist as hydrates or solvates, in which a certain stoichiometric amount of water or a solvent is associated with the molecule in the crystalline form. The hydrates and solvates of the compounds of formula (I) are also the subject of the invention.

The compounds of formula (I) can exist as stereoisomers since there is a chiral center in the molecule. The individual stereoisomers are encompassed by the structural formulas depicted herein. The various stereoisomers include enantiomers, diastereomers and atropisomers. One of skill in the art will understand that one stereoisomer may be more active and/or may exhibit beneficial properties relative to the other enantiomer. In addition, the skilled person in the art knows how to separate, enrich, and/or selectively prepare a stereoisomer of the isoxazoline compounds described herein. The isoxazoline compounds of formula (I) described herein contain a chiral quaternary carbon atom in the five-membered isoxazoline ring (shown by the asterisk (*)); therefore, the compounds will contain at least two possible stereoisomers. As an example for the compounds of formula (I), the two possible stereoisomers resulting from the chiral quaternary carbon are shown as formula (R)-I and (S)-I:

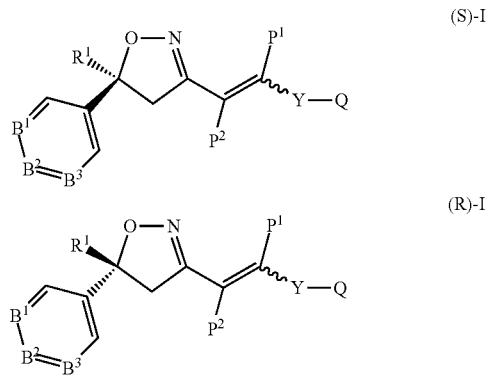

The compound of formula (S)-I above has the (S) configuration at the chiral carbon atom and the compound of formula (R)-I has the (R) configuration. In one embodiment, the compound of the invention is of formula (S)-I, where $B^1$, $B^2$, $B^3$, $R^1$, $P^1$, $P^2$, Y and Q are as defined above. In another embodiment, the compound of the invention is of formula (R)-I, where $B^1$, $B^2$, $B^3$, $R^1$, $P^1$, $P^2$, Y and Q are as defined above. In another embodiment, the compound is a racemic mixture of formula (S)-I and formula (R)-I, where $B^1$, $B^2$, $B^3$, $R^1$, $P^1$, $P^2$, Y and Q are as defined above.

Molecular depictions drawn herein follow standard conventions for depicting stereochemistry. To indicate stereo configuration, bonds rising from the plane of the drawing and towards the viewer are denoted by solid wedges wherein the broad end of the wedge is attached to the atom rising from the plane of the drawing towards the viewer. Bonds going below the plane of the drawing and away from the viewer are denoted by dashed wedges wherein the wide end of the wedge is attached to the atom further away from the viewer. Constant width lines indicate bonds with a direction opposite or neutral relative to bonds shown with solid or dashed wedges; constant width lines also depict bonds in molecules or parts of molecules in which no particular stereo configuration is intended to be specified.

Hence, in another embodiment, the invention provides a pesticidal and antiparasitic compound of formula (I) which is enriched in one enantiomer, or a pharmaceutically acceptable salt thereof.

In one embodiment, the invention provides a pesticidal and antiparasitic compound of formula (I), or a pharmaceutically acceptable salt thereof, or a composition comprising the compound which is enriched an enantiomer that displays significant in vitro and in vivo activity with a favorable toxicity profile (the eutomer). In one embodiment of the invention, the more biologically active enantiomer of the compound of Formula (I) is believed to be compound of Formula (S)-I shown above, which has the (S)-configuration at the chiral carbon atom.

In another embodiment, the invention provides compounds of formula (I), or pharmaceutically acceptable salts thereof, and compositions comprising the compounds, which are enriched in one enantiomer over the other enantiomer in a weight:weight ratio of at least 1.5:1. In another embodiment, the compound of Formula (I), or a pharmaceutically acceptable salt thereof, are enriched in one enantiomer in a weight:weight ratio of at least 2:1, at least 5:1 or at least 10:1.

In another embodiment, the compounds of Formula (I), or pharmaceutically acceptable salts thereof, of the invention are essentially pure enantiomers.

In one embodiment, the invention provides a compound of formula (I), or a pharmaceutically acceptable salt thereof, that is substantially enriched in an enantiomer. The term "substantially enriched" is meant wherein the weight:weight ratio is at least about 1.5:1 or higher in favor of the desired enantiomer. In another embodiment, the invention provides a compound of formula (I), that is substantially enriched in the (S)-enantiomer. In another embodiment, the invention provides a compound of formula (I) that is substantially enriched in the (R)-enantiomer.

In another embodiment of the invention, a compound of formula (I) is provided that is enriched in the (S)-enantiomer in a weight:weight ratio of at least about 2:1, (S) to (R), or greater. In yet another embodiment, the invention provides a compound of formula (I) that is enriched in the (S)-enantiomer in a weight:weight ratio of at least about 5:1, (S) to (R), or greater. In still another embodiment, the invention provides a compound of formula (I), that is enriched in the (S)-enantiomer in a weight:weight ratio of at least about 10:1, (S) to (R), or greater. In still another embodiment, the invention provides a compound of formula (I), that is essentially the pure (S)-enantiomer.

In one embodiment, the invention provides compounds of formula (I), wherein Y is Y-1, that that is enriched in the (S)-enantiomer in a weight:weight ratio of at least about 2:1, (S) to (R), or greater. In yet another embodiment, the invention provides a compound of formula (I) where Y is Y-1, that is enriched in the (S)-enantiomer in a weight:weight ratio of at least about 5:1, (S) to (R), or greater. In still another embodiment, the invention provides a compound of formula (I) where Y is Y-1, that is enriched in the (S)-enantiomer in a weight:weight ratio of at least about 10:1, (S) to (R), or greater. In still another embodiment, the invention provides a compound of formula (I) where Y is Y-1, that is essentially the pure (S)-enantiomer.

In another embodiment, the invention provides compounds of formula (I) wherein Y is Y-2, that that is enriched in the (S)-enantiomer in a weight:weight ratio of at least about 2:1, (S) to (R), or greater. In yet another embodiment, the invention provides a compound of formula (I) where Y is Y-2, that is enriched in the (S)-enantiomer in a weight:weight ratio of at least about 5:1, (S) to (R), or greater. In still another embodiment, the invention provides a compound of formula (I) where Y is Y-2, that is enriched in the (S)-enantiomer in a weight:weight ratio of at least about 10:1, (S) to (R), or greater. In still another embodiment, the invention provides a compound of formula (I) where Y is Y-2, that is essentially the pure (S)-enantiomer.

In one embodiment, the invention provides compounds of formula (I) wherein Y is Y-3, that that is enriched in the (S)-enantiomer in a weight:weight ratio of at least about 2:1, (S) to (R), or greater. In yet another embodiment, the invention provides a compound of formula (I) where Y is Y-3, that is enriched in the (S)-enantiomer in a weight:weight ratio of at least about 5:1, (S) to (R), or greater. In still another embodiment, the invention provides a compound of formula (I) where Y is Y-3, that is enriched in the (S)-enantiomer in a weight:weight ratio of at least about 10:1, (S) to (R), or greater. In still another embodiment, the invention provides a compound of formula (I) where Y is Y-3, that is essentially the pure (S)-enantiomer.

In one embodiment, the invention provides compounds of formula (I) wherein Y is Y-4, that that is enriched in the (S)-enantiomer in a weight:weight ratio of at least about 2:1, (S) to (R), or greater. In yet another embodiment, the invention provides a compound of formula (I) where Y is Y-4, that is enriched in the (S)-enantiomer in a weight:weight ratio of at least about 5:1, (S) to (R), or greater. In still another embodiment, the invention provides a compound of formula (I) where Y is Y-4, that is enriched in the (S)-enantiomer in a weight:weight ratio of at least about 10:1, (S) to (R), or greater. In still another embodiment, the invention provides a compound of formula (I) where Y is Y-4, that is essentially the pure (S)-enantiomer.

In one embodiment, the invention provides compounds of formula (I) wherein Y is Y-5, that that is enriched in the (S)-enantiomer in a weight:weight ratio of at least about 2:1, (S) to (R), or greater. In yet another embodiment, the invention provides a compound of formula (I) where Y is Y-5, that is enriched in the (S)-enantiomer in a weight:weight ratio of at least about 5:1, (S) to (R), or greater. In still another embodiment, the invention provides a compound of formula (I) where Y is Y-5, that is enriched in the (S)-enantiomer in a weight:weight ratio of at least about 10:1, (S) to (R), or greater. In still another embodiment, the invention provides a compound of formula (I) where Y is Y-5, that is essentially the pure (S)-enantiomer.

In one embodiment, the invention provides compounds of formula (I), wherein Y is Y-6, that that is enriched in the (S)-enantiomer in a weight:weight ratio of at least about 2:1, (S) to (R), or greater. In yet another embodiment, the invention provides a compound of formula (I) where Y is Y-6, that is enriched in the (S)-enantiomer in a weight:weight ratio of at least about 5:1, (S) to (R), or greater. In still another embodiment, the invention provides a compound of formula (I) where Y is Y-6, that is enriched in the (S)-enantiomer in a weight:weight ratio of at least about 10:1, (S) to (R), or greater. In still another embodiment, the invention provides a compound of formula (I) where Y is Y-6, that is essentially the pure (S)-enantiomer.

In one embodiment, the invention provides compounds of formula (I), wherein Y is Y-1; $B^1$, $B^2$ and $B^3$ are independently C—H, C—Cl, C—F or C—$CF_3$; $R^1$ is $CF_3$; and Q is X—$NR^2R^3$, that that is enriched in the (S)-enantiomer in a weight:weight ratio of at least about 2:1, (S) to (R), or greater. In yet another embodiment, the invention provides a compound of formula (I) where Y is Y-1; $B^1$, $B^2$ and $B^3$ are independently C—H, C—Cl, C—F or C—$CF_3$; $R^1$ is $CF_3$; and Q is X—$NR^2R^3$, that is enriched in the (S)-enantiomer in a weight:weight ratio of at least about 5:1, (S) to (R), or greater. In still another embodiment, the invention provides a compound of formula (I) where Y is Y-1; $B^1$, $B^2$ and $B^3$ are independently C—H, C—Cl, C—F or C—$CF_3$; $R^1$ is $CF_3$; and Q is X—$NR^2R^3$, that is enriched in the (S)-enantiomer in a weight:weight ratio of at least about 10:1, (S) to (R), or greater. In still another embodiment, the invention provides a compound of formula (I) where Y is Y-1; $B^1$, $B^2$ and $B^3$ are independently C—H, C—Cl, C—F or C—$CF_3$; $R^1$ is $CF_3$; and Q is X—$NR^2R^3$, that is essentially the pure (S)-enantiomer.

In another embodiment, the invention provides compounds of formula (I), wherein Y is Y-2; $B^1$, $B^2$ and $B^3$ are independently C—H, C—Cl, C—F or C—$CF_3$; $R^1$ is $CF_3$; and Q is X—$NR^2R^3$, that that is enriched in the (S)-enantiomer in a weight:weight ratio of at least about 2:1, (S) to (R), or greater. In yet another embodiment, the invention provides a compound of formula (I) where Y is Y-2; $B^1$, $B^2$ and $B^3$ are independently C—H, C—Cl, C—F or C—$CF_3$; $R^1$ is $CF_3$; and Q is X—$NR^2R^3$, that is enriched in the (S)-enantiomer in a weight:weight ratio of at least about 5:1, (S) to (R), or greater. In still another embodiment, the invention provides a compound of formula (I) where Y is Y-2; $B^1$, $B^2$ and $B^3$ are independently C—H, C—Cl, C—F or C—$CF_3$; $R^1$ is $CF_3$; and Q is X—$NR^2R^3$, that is enriched in the (S)-enantiomer in a weight:weight ratio of at least about 10:1, (S) to (R), or greater. In still another embodiment, the invention provides a compound of formula (I) where Y is Y-2; $B^1$, $B^2$ and $B^3$ are independently C—H, C—Cl, C—F or C—$CF_3$; $R^1$ is $CF_3$; and Q is X—$NR^2R^3$, that is essentially the pure (S)-enantiomer.

In one embodiment, the invention provides compounds of formula (I), wherein Y is Y-3; $B^1$, $B^2$ and $B^3$ are independently C—H, C—Cl, C—F or C—$CF_3$; $R^1$ is $CF_3$; and Q is (—$CH_2$—)(—$CH_2$—)N—$R^3$, that that is enriched in the (S)-enantiomer in a weight:weight ratio of at least about 2:1, (S) to (R), or greater. In yet another embodiment, the invention provides a compound of formula (I) where Y is Y-3; $B^1$, $B^2$ and $B^3$ are independently C—H, C—Cl, C—F or C—$CF_3$; $R^1$ is $CF_3$; and Q is (—$CH_2$—)(—$CH_2$—)N—$R^3$, that is enriched in the (S)-enantiomer in a weight:weight ratio of at least about 5:1, (S) to (R), or greater. In still another embodiment, the invention provides a compound of formula (I) where Y is Y-3; $B^1$, $B^2$ and $B^3$ are independently C—H, C—Cl, C—F or C—$CF_3$; $R^1$ is $CF_3$; and Q is (—$CH_2$—)(—$CH_2$—)N—$R^3$, that is enriched in the (S)-enantiomer in a weight:weight ratio of at least about 10:1, (S) to (R), or greater. In still another embodiment, the invention provides a compound of formula (I) where Y is Y-3; $B^1$, $B^2$ and $B^3$ are independently C—H, C—Cl, C—F or C—$CF_3$; $R^1$ is $CF_3$; and Q is (—$CH_2$—)(—$CH_2$—)N—$R^3$, that is essentially the pure (S)-enantiomer.

In one embodiment, the invention provides compounds of formula (I), wherein Y is Y-4; $B^1$, $B^2$ and $B^3$ are independently C—H, C—Cl, C—F or C—$CF_3$; $R^1$ is $CF_3$; and Q is X—$NR^2R^3$, that that is enriched in the (S)-enantiomer in a weight:weight ratio of at least about 2:1, (S) to (R), or greater. In yet another embodiment, the invention provides a compound of formula (I) where Y is Y-4; $B^1$, $B^2$ and $B^3$ are independently C—H, C—Cl, C—F or C—$CF_3$; $R^1$ is $CF_3$; and Q is X—$NR^2R^3$, that is enriched in the (S)-enantiomer in a weight:weight ratio of at least about 5:1, (S) to (R), or greater. In still another embodiment, the invention provides a compound of formula (I) where Y is Y-4; $B^1$, $B^2$ and $B^3$ are independently C—H, C—Cl, C—F or C—$CF_3$; $R^1$ is $CF_3$; and Q is X—$NR^2R^3$, that is enriched in the (S)-enantiomer in a weight:weight ratio of at least about 10:1, (S) to (R), or greater. In still another embodiment, the invention provides a compound of formula (I) where Y is Y-4; $B^1$, $B^2$ and $B^3$ are independently C—H, C—Cl, C—F or C—$CF_3$; $R^1$ is $CF_3$; and Q is X—$NR^2R^3$, that is essentially the pure (S)-enantiomer.

In one embodiment, the invention provides compounds of formula (I), wherein Y is Y-5; $B^1$, $B^2$ and $B^3$ are independently C—H, C—Cl, C—F or C—$CF_3$; $R^1$ is $CF_3$; and Q is X—$NR^2R^3$, that that is enriched in the (S)-enantiomer in a weight:weight ratio of at least about 2:1, (S) to (R), or greater. In yet another embodiment, the invention provides a compound of formula (I) where Y is Y-5; $B^1$, $B^2$ and $B^3$ are independently C—H, C—Cl, C—F or C—$CF_3$; $R^1$ is $CF_3$; and Q is X—$NR^2R^3$, that is enriched in the (S)-enantiomer in a weight:weight ratio of at least about 5:1, (S) to (R), or greater. In still another embodiment, the invention provides a compound of formula (I) where Y is Y-5; $B^1$, $B^2$ and $B^3$ are independently C—H, C—Cl, C—F or C—$CF_3$; $R^1$ is $CF_3$; and Q is X—$NR^2R^3$, that is enriched in the (S)-enantiomer in a weight:weight ratio of at least about 10:1, (S) to (R), or greater. In still another embodiment, the invention provides a compound of formula (I) where Y is Y-5; $B^1$, $B^2$ and $B^3$ are independently C—H, C—Cl, C—F or C—$CF_3$; $R^1$ is $CF_3$; and Q is X—$NR^2R^3$, that is essentially the pure (S)-enantiomer.

In one embodiment, the invention provides compounds of formula (I), wherein Y is Y-6; $B^1$, $B^2$ and $B^3$ are independently C—H, C—Cl, C—F or C—$CF_3$; $R^1$ is $CF_3$; and Q is OH or $C_1$-$C_3$alkoxy, that that is enriched in the (S)-enantiomer in a weight:weight ratio of at least about 2:1, (S) to (R), or greater. In yet another embodiment, the invention provides a compound of formula (I) where Y is Y-6; $B^1$, $B^2$ and $B^3$ are independently C—H, C—Cl, C—F or C—$CF_3$; $R^1$ is $CF_3$; and Q is OH or $C_1$-$C_3$alkoxy, that is enriched in the (S)-enantiomer in a weight:weight ratio of at least about 5:1, (S) to (R), or greater. In still another embodiment, the invention provides a compound of formula (I) where Y is Y-6; $B^1$, $B^2$ and $B^3$ are independently C—H, C—Cl, C—F or C—$CF_3$; $R^1$ is $CF_3$; and Q is OH or $C_1$-$C_3$alkoxy, that is enriched in the (S)-enantiomer in a weight:weight ratio of at least about 10:1, (S) to (R), or greater. In still another embodiment, the invention provides a compound of formula (I) where Y is Y-6; $B^1$, $B^2$ and $B^3$ are independently C—H, C—Cl, C—F or C—CF$_3$; $R^1$ is CF$_3$; and Q is OH or C$_1$-C$_3$alkoxy, that is essentially the pure (S)-enantiomer.

In one embodiment, the invention provides compounds of formula (I), wherein Y is Y-1; $B^1$, $B^2$ and $B^3$ are independently C—H, C—Cl, C—F or C—CF$_3$; $R^1$ is CF$_3$; and Q is X—NR$^2$R$^3$ wherein $R^2$ is H and $R^3$ is haloalkylaminocarbonylalkyl, haloalkylcarbonyl or C$_1$-C$_3$haloalkyl, that that is enriched in the (S)-enantiomer in a weight:weight ratio of at least about 2:1, (S) to (R), or greater. In yet another embodiment, the invention provides a compound of formula (I) where Y is Y-1; $B^1$, $B^2$ and $B^3$ are independently C—H, C—Cl, C—F or C—CF$_3$; $R^1$ is CF$_3$; and Q is X—NR$^2$R$^3$ wherein $R^2$ is H and $R^3$ is haloalkylaminocarbonylalkyl, haloalkylcarbonyl or C$_1$-C$_3$haloalkyl, that is enriched in the (S)-enantiomer in a weight:weight ratio of at least about 5:1, (S) to (R), or greater. In still another embodiment, the invention provides a compound of formula (I) where Y is Y-1; $B^1$, $B^2$ and $B^3$ are independently C—H, C—Cl, C—F or C—CF$_3$; $R^1$ is CF$_3$; and Q is X—NR$^2$R$^3$ wherein $R^2$ is H and $R^3$ is haloalkylaminocarbonylalkyl, haloalkylcarbonyl or C$_1$-C$_3$haloalkyl, that is enriched in the (S)-enantiomer in a weight:weight ratio of at least about 10:1, (S) to (R), or greater. In still another embodiment, the invention provides a compound of formula (I) where Y is Y-1; $B^1$, $B^2$ and $B^3$ are independently C—H, C—Cl, C—F or C—CF$_3$; $R^1$ is CF$_3$; and Q is X—NR$^2$R$^3$ wherein $R^2$ is H and $R^3$ is haloalkylaminocarbonylalkyl, haloalkylcarbonyl or C$_1$-C$_3$haloalkyl, that is essentially the pure (S)-enantiomer.

In another embodiment, the invention provides compounds of formula (I), wherein Y is Y-2; $B^1$, $B^2$ and $B^3$ are independently C—H, C—Cl, C—F or C—CF$_3$; $R^1$ is CF$_3$; and Q is X—NR$^2$R$^3$ wherein $R^2$ is H and $R^3$ is haloalkylaminocarbonylalkyl, haloalkylcarbonyl or C$_1$-C$_3$haloalkyl, that that is enriched in the (S)-enantiomer in a weight:weight ratio of at least about 2:1, (S) to (R), or greater. In yet another embodiment, the invention provides a compound of formula (I) where Y is Y-2; $B^1$, $B^2$ and $B^3$ are independently C—H, C—Cl, C—F or C—CF$_3$; $R^1$ is CF$_3$; and Q is X—NR$^2$R$^3$ wherein $R^2$ is H and $R^3$ is haloalkylaminocarbonylalkyl, haloalkylcarbonyl or C$_1$-C$_3$haloalkyl, that is enriched in the (S)-enantiomer in a weight:weight ratio of at least about 5:1, (S) to (R), or greater. In still another embodiment, the invention provides a compound of formula (I) where Y is Y-2; $B^1$, $B^2$ and $B^3$ are independently C—H, C—Cl, C—F or C—CF$_3$; $R^1$ is CF$_3$; and Q is X—NR$^2$R$^3$ wherein $R^2$ is H and $R^3$ is haloalkylaminocarbonylalkyl, haloalkylcarbonyl or C$_1$-C$_3$haloalkyl, that is enriched in the (S)-enantiomer in a weight:weight ratio of at least about 10:1, (S) to (R), or greater. In still another embodiment, the invention provides a compound of formula (I) where Y is Y-2; $B^1$, $B^2$ and $B^3$ are independently C—H, C—Cl, C—F or C—CF$_3$; $R^1$ is CF$_3$; and Q is X—NR$^2$R$^3$ wherein $R^2$ is H and $R^3$ is haloalkylaminocarbonylalkyl, haloalkylcarbonyl or C$_1$-C$_3$haloalkyl, that is essentially the pure (S)-enantiomer.

In one embodiment, the invention provides compounds of formula (I), wherein Y is Y-3; $B^1$, $B^2$ and $B^3$ are independently C—H, C—Cl, C—F or C—CF$_3$; $R^1$ is CF$_3$; and Q is (—CH$_2$—)(—CH$_2$—)N—C(=O)CH$_2$S(O)$_2$CH$_3$, that that is enriched in the (S)-enantiomer in a weight:weight ratio of at least about 2:1, (S) to (R), or greater. In yet another embodiment, the invention provides a compound of formula (I) where Y is Y-3; $B^1$, $B^2$ and $B^3$ are independently C—H, C—Cl, C—F or C—CF$_3$; $R^1$ is CF$_3$; and Q is (—CH$_2$—)(—CH$_2$—)N—C(=O)CH$_2$S(O)$_2$CH$_3$, that is enriched in the (S)-enantiomer in a weight:weight ratio of at least about 5:1, (S) to (R), or greater. In still another embodiment, the invention provides a compound of formula (I) where Y is Y-3; $B^1$, $B^2$ and $B^3$ are independently C—H, C—Cl, C—F or C—CF$_3$; $R^1$ is CF$_3$; and Q is (—CH$_2$—)(—CH$_2$—)N—C(=O)CH$_2$S(O)$_2$CH$_3$, that is essentially the pure (S)-enantiomer.

In one embodiment, the invention provides compounds of formula (I), wherein Y is Y-4; $B^1$, $B^2$ and $B^3$ are independently C—H, C—Cl, C—F or C—CF$_3$; $R^1$ is CF$_3$; and Q is X—NR$^2$R$^3$ wherein $R^2$ is H and $R^3$ is haloalkylaminocarbonylalkyl, haloalkylcarbonyl or C$_1$-C$_3$haloalkyl, that that is enriched in the (S)-enantiomer in a weight:weight ratio of at least about 2:1, (S) to (R), or greater. In yet another embodiment, the invention provides a compound of formula (I) where Y is Y-4; $B^1$, $B^2$ and $B^3$ are independently C—H, C—Cl, C—F or C—CF$_3$; $R^1$ is CF$_3$; and Q is X—NR$^2$R$^3$ wherein $R^2$ is H and $R^3$ is haloalkylaminocarbonylalkyl, haloalkylcarbonyl or C$_1$-C$_3$haloalkyl, that is enriched in the (S)-enantiomer in a weight:weight ratio of at least about 5:1, (S) to (R), or greater. In still another embodiment, the invention provides a compound of formula (I) where Y is Y-4; $B^1$, $B^2$ and $B^3$ are independently C—H, C—Cl, C—F or C—CF$_3$; $R^1$ is CF$_3$; and Q is X—NR$^2$R$^3$ wherein $R^2$ is H and $R^3$ is haloalkylaminocarbonylalkyl, haloalkylcarbonyl or C$_1$-C$_3$haloalkyl, that is enriched in the (S)-enantiomer in a weight:weight ratio of at least about 10:1, (S) to (R), or greater. In still another embodiment, the invention provides a compound of formula (I) where Y is Y-4; $B^1$, $B^2$ and $B^3$ are independently C—H, C—Cl, C—F or C—CF$_3$; $R^1$ is CF$_3$; and Q is X—NR$^2$R$^3$ wherein $R^2$ is H and $R^3$ is haloalkylaminocarbonylalkyl, haloalkylcarbonyl or C$_1$-C$_3$haloalkyl, that is essentially the pure (S)-enantiomer.

In one embodiment, the invention provides compounds of formula (I), wherein Y is Y-5; $B^1$, $B^2$ and $B^3$ are independently C—H, C—Cl, C—F or C—CF$_3$; $R^1$ is CF$_3$; and Q is X—NR$^2$R$^3$ wherein $R^2$ is H and $R^3$ is haloalkylaminocarbonylalkyl, haloalkylcarbonyl or C$_1$-C$_3$haloalkyl, that that is enriched in the (S)-enantiomer in a weight:weight ratio of at least about 2:1, (S) to (R), or greater. In yet another embodiment, the invention provides a compound of formula (I) where Y is Y-5; $B^1$, $B^2$ and $B^3$ are independently C—H, C—Cl, C—F or C—CF$_3$; $R^1$ is CF$_3$; and Q is X—NR$^2$R$^3$ wherein $R^2$ is H and $R^3$ is haloalkylaminocarbonylalkyl, haloalkylcarbonyl or C$_1$-C$_3$haloalkyl, that is enriched in the (S)-enantiomer in a weight:weight ratio of at least about 5:1, (S) to (R), or greater. In still another embodiment, the invention provides a compound of formula (I) where Y is Y-5; $B^1$, $B^2$ and $B^3$ are independently C—H, C—Cl, C—F or C—CF$_3$; $R^1$ is CF$_3$; and Q is X—NR$^2$R$^3$ wherein $R^2$ is H and $R^3$ is haloalkylaminocarbonylalkyl, haloalkylcarbonyl or C$_1$-C$_3$haloalkyl, that is enriched in the (S)-enantiomer in a weight:weight ratio of at least about 10:1, (S) to (R), or greater. In still another embodiment, the invention provides a compound of formula (I) where Y is Y-5; $B^1$, $B^2$ and $B^3$ are independently C—H, C—Cl, C—F or C—CF$_3$; $R^1$ is CF$_3$; and Q is X—NR$^2$R$^3$ wherein $R^2$ is H and $R^3$ is haloalkylaminocarbonylalkyl, haloalkylcarbonyl or C$_1$-C$_3$haloalkyl, that is essentially the pure (S)-enantiomer.

In one embodiment, the invention provides compounds of formula (I), wherein Y is Y-6; $B^1$, $B^2$ and $B^3$ are independently C—H, C—Cl, C—F or C—CF$_3$; $R^1$ is CF$_3$; and Q is OH, that that is enriched in the (S)-enantiomer in a weight:

weight ratio of at least about 2:1, (S) to (R), or greater. In yet another embodiment, the invention provides a compound of formula (I) where Y is Y-6; $B^1$, $B^2$ and $B^3$ are independently C—H, C—Cl, C—F or C—$CF_3$; $R^1$ is $CF_3$; and Q is OH, that is enriched in the (S)-enantiomer in a weight:weight ratio of at least about 5:1, (S) to (R), or greater. In still another embodiment, the invention provides a compound of formula (I) where Y is Y-6; $B^1$, $B^2$ and $B^3$ are independently C—H, C—Cl, C—F or C—$CF_3$; $R^1$ is $CF_3$; and Q is OH, that is enriched in the (S)-enantiomer in a weight:weight ratio of at least about 10:1, (S) to (R), or greater. In still another embodiment, the invention provides a compound of formula (I) where Y is Y-6; $B^1$, $B^2$ and $B^3$ are independently C—H, C—Cl, C—F or C—$CF_3$; $R^1$ is $CF_3$; and Q is OH, that is essentially the pure (S)-enantiomer.

In one embodiment, the invention provides compounds of formula (I), wherein Y is Y-1; $B^1$ is C—Cl; $B^2$ is C—H or C—F; $B^3$ is C—Cl or C—$CF_3$; $R^1$ is $CF_3$; and Q is X—$NR^2R^3$ wherein $R^2$ is H and $R^3$ is —$CH_2C(O)NHCH_2CF_3$, —$C(O)CH_2CF_3$, —$CH_2CF_3$, —$CF_2CF_3$ or —$CF_3$, that that is enriched in the (S)-enantiomer in a weight:weight ratio of at least about 2:1, (S) to (R), or greater. In yet another embodiment, the invention provides a compound of formula (I) where Y is Y-1; $B^1$ is C—Cl; $B^2$ is C—H or C—F; $B^3$ is C—Cl or C—$CF_3$; $R^1$ is $CF_3$; and Q is X—$NR^2R^3$ wherein $R^2$ is H and $R^3$ is —$CH_2C(O)NHCH_2CF_3$, —$C(O)CH_2CF_3$, —$CH_2CF_3$, —$CF_2CF_3$ or —$CF_3$, that is enriched in the (S)-enantiomer in a weight:weight ratio of at least about 5:1, (S) to (R), or greater. In still another embodiment, the invention provides a compound of formula (I) where Y is Y-1; $B^1$ is C—Cl; $B^2$ is C—H or C—F; $B^3$ is C—Cl or C—$CF_3$; $R^1$ is $CF_3$; and Q is X—$NR^2R^3$ wherein $R^2$ is H and $R^3$ is —$CH_2C(O)NHCH_2CF_3$, —$C(O)CH_2CF_3$, —$CH_2CF_3$, —$CF_2CF_3$ or —$CF_3$, that is enriched in the (S)-enantiomer in a weight:weight ratio of at least about 10:1, (S) to (R), or greater. In still another embodiment, the invention provides a compound of formula (I) where Y is Y-1; $B^1$ is C—Cl; $B^2$ is C—H or C—F; $B^3$ is C—Cl or C—$CF_3$; $R^1$ is $CF_3$; and Q is X—$NR^2R^3$ wherein $R^2$ is H and $R^3$ is —$CH_2C(O)NHCH_2CF_3$, —$C(O)CH_2CF_3$, —$CH_2CF_3$, —$CF_2CF_3$ or —$CF_3$, that is essentially the pure (S)-enantiomer.

In another embodiment, the invention provides compounds of formula (I), wherein Y is Y-2; $B^1$ is C—Cl; $B^2$ is C—H or C—F; $B^3$ is C—Cl or C—$CF_3$; $R^1$ is $CF_3$; and Q is X—$NR^2R^3$ wherein $R^2$ is H and $R^3$ is —$CH_2C(O)NHCH_2CF_3$, —$C(O)CH_2CF_3$, —$CH_2CF_3$, —$CF_2CF_3$ or —$CF_3$, that is enriched in the (S)-enantiomer in a weight:weight ratio of at least about 2:1, (S) to (R), or greater. In yet another embodiment, the invention provides a compound of formula (I) where Y is Y-2; $B^1$ is C—Cl; $B^2$ is C—H or C—F; $B^3$ is C—Cl or C—$CF_3$; $R^1$ is $CF_3$; and Q is X—$NR^2R^3$ wherein $R^2$ is H and $R^3$ is —$CH_2C(O)NHCH_2CF_3$, —$C(O)CH_2CF_3$, —$CH_2CF_3$, —$CF_2CF_3$ or —$CF_3$, that is enriched in the (S)-enantiomer in a weight:weight ratio of at least about 5:1, (S) to (R), or greater. In still another embodiment, the invention provides a compound of formula (I) where Y is Y-2; $B^1$ is C—Cl; $B^2$ is C—H or C—F; $B^3$ is C—Cl or C—$CF_3$; $R^1$ is $CF_3$; and Q is X—$NR^2R^3$ wherein $R^2$ is H and $R^3$ is —$CH_2C(O)NHCH_2CF_3$, —$C(O)CH_2CF_3$, —$CH_2CF_3$, —$CF_2CF_3$ or —$CF_3$, that is enriched in the (S)-enantiomer in a weight:weight ratio of at least about 10:1, (S) to (R), or greater. In still another embodiment, the invention provides a compound of formula (I) where Y is Y-2; $B^1$ is C—Cl; $B^2$ is C—H or C—F; $B^3$ is C—Cl or C—$CF_3$; $R^1$ is $CF_3$; and Q is X—$NR^2R^3$ wherein $R^2$ is H and $R^3$ is —$CH_2C(O)NHCH_2CF_3$, —$C(O)CH_2CF_3$, —$CH_2CF_3$, —$CF_2CF_3$ or —$CF_3$, that is essentially the pure (S)-enantiomer.

In one embodiment, the invention provides compounds of formula (I), wherein Y is Y-3; $B^1$ is C—Cl; $B^2$ is C—F; $B^3$ is C—Cl or C—$CF_3$; and Q is (—$CH_2$—)(—$CH_2$—)N—C(=O)$CH_2S(O)_2CH_3$, that that is enriched in the (S)-enantiomer in a weight:weight ratio of at least about 2:1, (S) to (R), or greater. In yet another embodiment, the invention provides a compound of formula (I) where Y is Y-3; $B^1$ is C—Cl; $B^2$ is C—F; $B^3$ is C—Cl or C—$CF_3$; $R^1$ is $CF_3$; and Q is (—$CH_2$—)(—$CH_2$—)N—C(=O)$CH_2S(O)_2CH_3$, that is enriched in the (S)-enantiomer in a weight:weight ratio of at least about 5:1, (S) to (R), or greater. In still another embodiment, the invention provides a compound of formula (I) where Y is Y-3; $B^1$ is C—Cl; $B^2$ is C—F; $B^3$ is C—Cl or C—$CF_3$; $R^1$ is $CF_3$; and Q is (—$CH_2$—)(—$CH_2$—)N—C(=O)$CH_2S(O)_2CH_3$, that is enriched in the (S)-enantiomer in a weight:weight ratio of at least about 10:1, (S) to (R), or greater. In still another embodiment, the invention provides a compound of formula (I) where Y is Y-3; $B^1$ is C—Cl; $B^2$ is C—F; $B^3$ is C—Cl or C—$CF_3$; and Q is (—$CH_2$—)(—$CH_2$—)N—C(=O)$CH_2S(O)_2CH_3$, that is essentially the pure (S)-enantiomer.

In one embodiment, the invention provides compounds of formula (I), wherein Y is Y-4; $B^1$ is C—Cl; $B^2$ is C—H, C—Cl or C—F; $B^3$ is C—Cl or C—$CF_3$; $R^1$ is $CF_3$; and Q is X—$NR^2R^3$ wherein $R^2$ is H and $R^3$ is —$CH_2C(O)NHCH_2CF_3$, —$C(O)CH_2CF_3$, —$CH_2CF_3$, —$CF_2CF_3$ or —$CF_3$, that that is enriched in the (S)-enantiomer in a weight:weight ratio of at least about 2:1, (S) to (R), or greater. In yet another embodiment, the invention provides a compound of formula (I) where Y is Y-4; $B^1$ is C—Cl; $B^2$ is C—H, C—Cl or C—F; $B^3$ is C—Cl or C—$CF_3$; $R^1$ is $CF_3$; and Q is X—$NR^2R^3$ wherein $R^2$ is H and $R^3$ is —$CH_2C(O)NHCH_2CF_3$, —$C(O)CH_2CF_3$, —$CH_2CF_3$, —$CF_2CF_3$ or —$CF_3$, that is enriched in the (S)-enantiomer in a weight:weight ratio of at least about 5:1, (S) to (R), or greater. In still another embodiment, the invention provides a compound of formula (I) where Y is Y-4; $B^1$ is C—Cl; $B^2$ is C—H, C—Cl or C—F; $B^3$ is C—Cl or C—$CF_3$; $R^1$ is $CF_3$; and Q is X—$NR^2R^3$ wherein $R^2$ is H and $R^3$ is —$CH_2C(O)NHCH_2CF_3$, —$C(O)CH_2CF_3$, —$CH_2CF_3$, —$CF_2CF_3$ or —$CF_3$, that is enriched in the (S)-enantiomer in a weight:weight ratio of at least about 10:1, (S) to (R), or greater. In still another embodiment, the invention provides a compound of formula (I) where Y is Y-4; $B^1$ is C—Cl; $B^2$ is C—H, C—Cl or C—F; $B^3$ is C—Cl or C—$CF_3$; $R^1$ is $CF_3$; and Q is X—$NR^2R^3$ wherein $R^2$ is H and $R^3$ is —$CH_2C(O)NHCH_2CF_3$, —$C(O)CH_2CF_3$, —$CH_2CF_3$, —$CF_2CF_3$ or —$CF_3$, that is essentially the pure (S)-enantiomer.

In one embodiment, the invention provides compounds of formula (I), wherein Y is Y-5; $B^1$, $B^2$ and $B^3$ are each C—Cl; $R^1$ is $CF_3$; and Q is X—$NR^2R^3$ wherein $R^2$ is H and $R^3$ is —$CH_2C(O)NHCH_2CF_3$, —$C(O)CH_2CF_3$, —$CH_2CF_3$, —$CF_2CF_3$ or —$CF_3$, that that is enriched in the (S)-enantiomer in a weight:weight ratio of at least about 2:1, (S) to (R), or greater. In yet another embodiment, the invention provides a compound of formula (I) where Y is Y-5; $B^1$, $B^2$ and $B^3$ are each C—Cl; $R^1$ is $CF_3$; and Q is X—$NR^2R^3$ wherein $R^2$ is H and $R^3$ is —$CH_2C(O)NHCH_2CF_3$, —$C(O)CH_2CF_3$, —$CH_2CF_3$, —$CF_2CF_3$ or —$CF_3$, that is enriched in the (S)-enantiomer in a weight:weight ratio of at least about 5:1, (S) to (R), or greater. In still another embodiment, the invention provides a compound of formula (I) where Y is Y-5; $B^1$, $B^2$ and $B^3$ are each C—Cl; $R^1$ is $CF_3$; and Q is X—$NR^2R^3$ wherein $R^2$ is H and $R^3$ is —$CH_2C(O)NHCH_2CF_3$, —$C(O)CH_2CF_3$, —$CH_2CF_3$, —$CF_2CF_3$ or —CF$_3$, that is enriched in the (S)-enantiomer in a weight: weight ratio of at least about 10:1, (S) to (R), or greater. In still another embodiment, the invention provides a compound of formula (I) where Y is Y-5; B$^1$, B$^2$ and B$^3$ are each C—Cl; R$^1$ is CF$_3$; and Q is X—NR$^2$R$^3$ wherein R$^2$ is H and R$^3$ is —CH$_2$C(O)NHCH$_2$CF$_3$, —C(O)CH$_2$CF$_3$, —CH$_2$CF$_3$, —CF$_2$CF$_3$ or —CF$_3$, that is essentially the pure (S)-enantiomer.

In one embodiment, the invention provides compounds of formula (I), wherein Y is Y-6; B$^1$, B$^2$ and B$^3$ are each C—Cl; R$^1$ is CF$_3$; and Q is OH or C$_1$-C$_3$alkoxy, that that is enriched in the (S)-enantiomer in a weight:weight ratio of at least about 2:1, (S) to (R), or greater. In yet another embodiment, the invention provides a compound of formula (I) where Y is Y-6; B$^1$, B$^2$ and B$^3$ are each C—Cl; R$^1$ is CF$_3$; and Q is OH or C$_1$-C$_3$alkoxy, that is enriched in the (S)-enantiomer in a weight:weight ratio of at least about 5:1, (S) to (R), or greater. In still another embodiment, the invention provides a compound of formula (I) where Y is Y-6; B$^1$, B$^2$ and B$^3$ are each C—Cl; R$^1$ is CF$_3$; and Q is OH or C$_1$-C$_3$alkoxy, that is enriched in the (S)-enantiomer in a weight:weight ratio of at least about 10:1, (S) to (R), or greater. In still another embodiment, the invention provides a compound of formula (I) where Y is Y-6; B$^1$, B$^2$ and B$^3$ are each C—Cl; R$^1$ is CF$_3$; and Q is OH or C$_1$-C$_3$alkoxy, that is essentially the pure (S)-enantiomer.

When enantiomerically enriched, one enantiomer is present in greater amounts than the other, and the extent of enrichment may be defined by an expression of enantiomeric excess ("ee"), which is defined as (2x−1)·100%, where x is the mole fraction of the dominant enantiomer in the mixture (e.g., an ee of 20% corresponds to a 60:40 ratio of enantiomers). In some embodiments, the compositions of the invention comprise compounds that have at least a 50% enantiomeric excess. In other embodiments, the compositions of the invention comprise compounds that have at least a 75% enantiomeric excess, at least a 90% enantiomeric excess, or at least a 94% enantiomeric excess of the more active isomer. Of particular note are enantiomerically pure embodiments of the more active isomer (the eutomer).

Compounds of this invention can exist as one or more conformational isomers due to restricted rotation about the amide bond bonded to the aryl or heteroaryl ring (e.g. the amide X—NR$^2$R$^3$ where X is C(=O) bonded to the naphthyl group in formula (I). This invention comprises mixtures of conformational isomers. In addition, this invention includes compounds that are enriched in one conformer relative to others.

It will be appreciated that in addition to the chiral carbon atom in the isoxazoline ring of the compounds of formula (I), certain compounds may include other chiral centers in one or more substituents. Thus, these compounds will have a greater number of possible stereoisomers (e.g. diastereomers). All possible stereoisomers are encompassed in the extended release injectable compositions of the invention.

In certain embodiments, the present invention provides the pesticidal and parasiticidal compounds provided in the Table 59 below:

| Compound # | Structure |
|---|---|
| 1 | 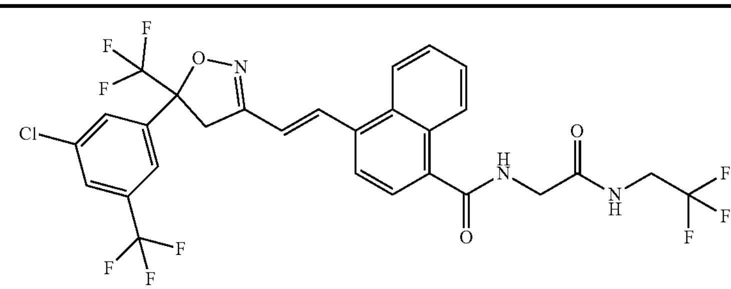 |
| 2 | 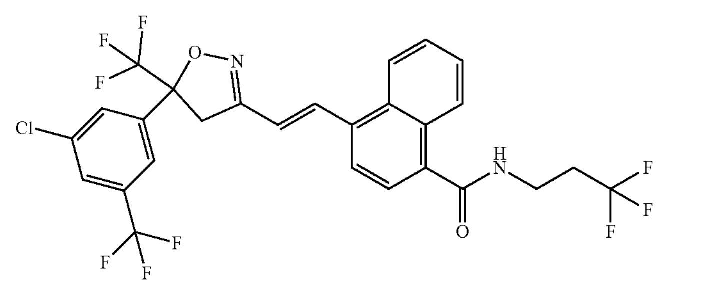 [SMILES: O=C(NCCC(F)(F)F)c1ccc(/C=C/C2=NOC(c3cc(Cl)cc(C(F)(F)F)c3)(C(F)(F)F)C2)c2ccccc12] |
| 3 | 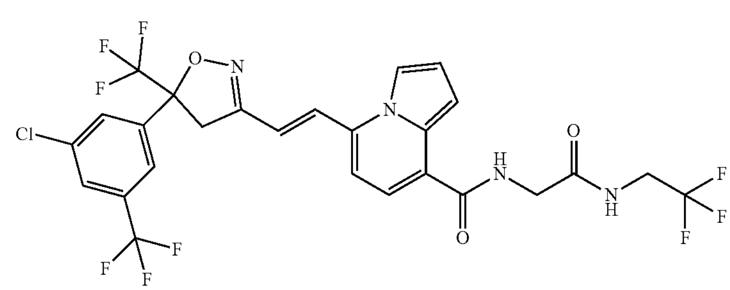 [SMILES: O=C(CNC(=O)c1ccc(/C=C/C2=NOC(c3cc(Cl)cc(C(F)(F)F)c3)(C(F)(F)F)C2)n2cccc12)NCC(F)(F)F] |

| Compound # | Structure |
|---|---|
| 4 | 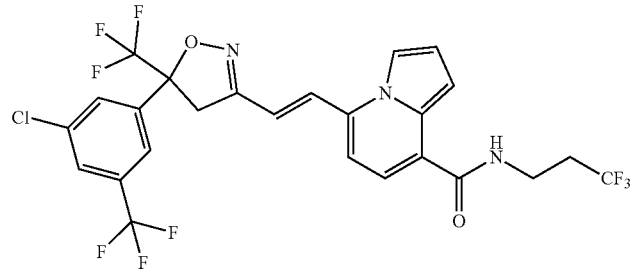 [SMILES: O=C(NCCC(F)(F)F)c1ccc(/C=C/C2=NOC(c3cc(Cl)cc(C(F)(F)F)c3)(C(F)(F)F)C2)n2cccc12] |
| 5 | 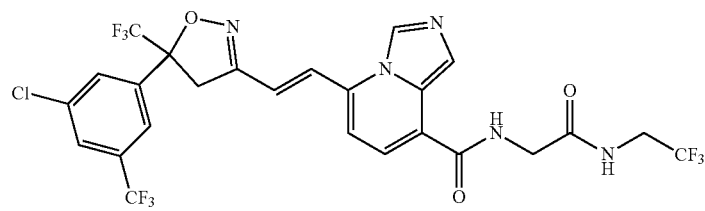 [SMILES: O=C(CNC(=O)c1ccc(/C=C/C2=NOC(c3cc(Cl)cc(C(F)(F)F)c3)(C(F)(F)F)C2)n2cncc12)NCC(F)(F)F] |
| 6 | 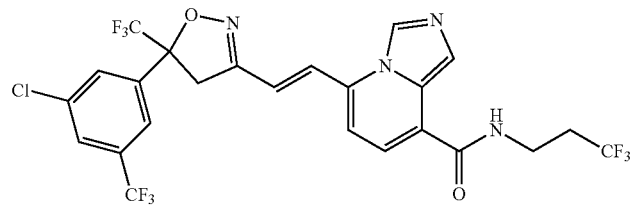 [SMILES: O=C(NCCC(F)(F)F)c1ccc(/C=C/C2=NOC(c3cc(Cl)cc(C(F)(F)F)c3)(C(F)(F)F)C2)n2cncc12] |

Salts

In addition to the neutral compounds of formula (I), salt forms of the compounds are also active against animal pests. The terms "veterinarily acceptable salt" and "agriculturally acceptable salt" are used throughout the specification to describe any salts of the compounds that are acceptable for administration for veterinary and agricultural applications, and which provides the active compound upon administration.

In cases where compounds are sufficiently basic or acidic to form stable non-toxic acid or base salts, the compounds may be in the form of a veterinarily or agriculturally acceptable salt. Veterinarily or agriculturally acceptable salts include those derived from veterinarily or agriculturally acceptable inorganic or organic bases and acids. Suitable salts include those comprising alkali metals such as lithium, sodium or potassium, alkaline earth metals such as calcium, magnesium and barium. Salts comprising transition metals including, but not limited to, manganese, copper, zinc and iron are also suitable. In addition, salts comprising ammonium cations ($NH_4^+$) as well as substituted ammonium cations, in which one or more of the hydrogen atoms are replaced by alkyl or aryl groups are encompassed by the invention.

Salts derived from inorganic acids including, but not limited to, hydrohalide acids (HCl, HBr, HF, HI), sulfuric acid, nitric acid, phosphoric acid, and the like are particularly suitable. Suitable inorganic salts also include, but not limited to, bicarbonate, and carbonate salts. In some embodiments, examples of veterinarily and agriculturally acceptable salts are organic acid addition salts formed with organic acids including, but not limited to, maleate, dimaleate, fumarate, tosylate, methanesulfonate, acetate, citrate, malonate, tartarate, succinate, benzoate, ascorbate, α-ketoglutarate, and α-glycerophosphate. Of course, other acceptable organic acids may be used.

Alkali metal (for example, sodium, potassium or lithium) or alkaline earth metal (for example calcium) salts of the compounds can also be made by reacting a sufficiently acidic residue on the compounds with a hydroxide of the alkali metal or alkaline earth metal. Veterinarily and agriculturally acceptable salts may be obtained using standard procedures well known in the art, for example by reacting a sufficiently basic compound such as an amine with a suitably acid functional group present in the compound, or by reacting a suitable acid with a suitably basic functional group on the compound of the invention.

Definitions

For the purposes of this application, unless otherwise stated in the specification, the following terms have the terminology cited below:

(1) Alkyl refers to both straight and branched carbon chains hydrocarbon groups. In one embodiment of alkyl, the number of carbons atoms is 1-20, in other embodiments of alkyl, the number of carbon atoms is 1-12, 1-10 or 1-8 carbon atoms. In yet another embodiment of alkyl, the number of carbon atoms is 1-6, 1-4 or 1-2 carbon atoms. Other ranges of carbon numbers are also contemplated depending on the location of the alkyl moiety on the molecule;

Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

Cyclic alkyl groups may be referred to as "cycloalkyl" and include those with 3 to 10 carbon atoms having single or multiple fused rings. In other embodiments, the cycloalkyl groups may have 3 to 8 carbon atoms or 3 to 6 carbon atoms in the ring. Non-limiting examples of cycloalkyl groups include adamantyl, cyclopropyl, cyclobutyl, cyclopentyl, cyclohexyl, cycloheptyl, cyclooctyl and the like.

The alkyl and cycloalkyl groups described herein can be unsubstituted or substituted with one or more moieties selected from the group consisting of alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamoyl, ester, phosphonyl, phosphinyl, phosphoryl, phosphine, thioester, thioether, acid halide, anhydride, oxime, hydrazine, carbamate, phosphonic acid, phosphate, phosphonate, or any other viable functional group that does not inhibit the biological activity of the compounds of the invention, either unprotected, or protected as necessary, as known to those skilled in the art, for example, as taught in Greene, et al., *Protective Groups in Organic Synthesis*, John Wiley and Sons, Fourth Edition, 2007, hereby incorporated by reference.

(2) Alkenyl refers to both straight and branched carbon chains which have at least one carbon-carbon double bond. In one embodiment of alkenyl, the number of double bonds is 1-3, in another embodiment of alkenyl, the number of double bonds is one. In one embodiment of alkenyl, the number of carbons atoms is 2-20, in other embodiments of alkenyl, the number of carbon atoms is 2-12, 2-10, 2-8 or 2-6. In yet another embodiment of alkenyl, the number of carbon atoms is 2-4. Other ranges of carbon-carbon double bonds and carbon numbers are also contemplated depending on the location of the alkenyl moiety on the molecule.

"$C_2$-$C_{10}$-alkenyl" groups may include more than one double bond in the chain. Examples include, but are not limited to, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

(3) Alkynyl refers to both straight and branched carbon chains which have at least one carbon-carbon triple bond. In one embodiment of alkynyl, the number of triple bonds is 1-3; in another embodiment of alkynyl, the number of triple bonds is one. In one embodiment of alkynyl, the number of carbons atoms is 2-20, in other embodiments of alkynyl, the number of carbon atoms is 2-12, 2-10, 2-8 or 2-6. In yet another embodiment of alkynyl, the number of carbon atoms is 2-4. Other ranges of carbon-carbon double bonds and carbon numbers are also contemplated depending on the location of the alkenyl moiety on the molecule;

For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

(4) Aryl refers to a $C_6$-$C_{14}$ aromatic carbocyclic ring structure having a single ring or multiple fused rings. In some embodiments, the aryl ring may be fused to a non-aromatic ring, as long as the point of attachment to the core structure is through the aromatic ring. Aryl groups include, but are not limited to, phenyl, biphenyl, and naphthyl. In some embodiments aryl includes tetrahydronapthyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, arylthio, cycloalkylthio, halocycloalkylthio, alkylsulfinyl, alkenylsulfinyl, alkynyl-sulfinyl, haloalkylsulfinyl, haloalkenylsulfinyl, haloalkynylsulfinyl, alkylsulfonyl, alkenylsulfonyl, alkynylsulfonyl, haloalkylsulfonyl, haloalkenylsulfonyl, haloalkynylsulfonyl, alkylcarbonyl, haloalkylcarbonyl, alkylamino, alkenylamino, alkynylamino, di(alkyl)amino, di(alkenyl)-amino, di(alkynyl)amino, or $SF_5$. In one embodiment of aryl, the moiety is phenyl, naphthyl, tetrahydronapthyl, phenylcyclopropyl and indanyl; in another embodiment of aryl, the moiety is phenyl.

(5) Alkoxy refers to —O-alkyl, wherein alkyl is as defined in (1);

(6) Alkoxycarbonyl refers to —C(=O)—O-alkyl, wherein alkoxy is as defined in (5);

(7) Cyclo as a prefix (e.g. cycloalkyl, cycloalkenyl, cycloalkynyl) refers to a saturated or unsaturated cyclic ring structure having from three to eight carbon atoms in the ring the scope of which is intended to be separate and distinct from the definition of aryl above. In one embodiment of cyclo, the range of ring sizes is 4-7 carbon atoms; in another embodiment of cyclo the range of ring sizes is 3-4. Other ranges of carbon numbers are also contemplated depending on the location of the cyclo-moiety on the molecule;

(8) Halogen means the atoms fluorine, chlorine, bromine and iodine. The designation of "halo" (e.g. as illustrated in the term haloalkyl) refers to all degrees of substitutions from a single substitution to a perhalo substitution (e.g. as illustrated with methyl as chloromethyl (—$CH_2Cl$), dichloromethyl (—$CHCl_2$), trichloromethyl (—$CCl_3$));

(9) Heterocycle, heterocyclic or heterocyclo refers to fully saturated or unsaturated cyclic groups, for example, 4 to 7 membered monocyclic, 7 to 11 membered bicyclic, or 10 to 15 membered tricyclic ring systems, which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

(10) Heteroaryl refers to a monovalent aromatic group of from 1 to 15 carbon atoms, preferably from 1 to 10 carbon atoms, having one or more oxygen, nitrogen, and sulfur heteroatoms within the ring, preferably 1 to 4 heteroatoms, or 1 to 3 heteroatoms. The nitrogen and sulfur heteroatoms may optionally be oxidized. Such heteroaryl groups can have a single ring (e.g., pyridyl or furyl) or multiple fused rings provided that the point of attachment is through a heteroaryl ring atom. Preferred heteroaryls include pyridyl, piridazinyl, pyrimidinyl, triazinyl, pyrrolyl, quinolinyl, isoquinolinyl, quinazolinyl, quinoxalinnyl, furanyl, thienyl, furyl, imidazolyl, oxazolyl, isoxazolyl, isothiazolyl, pyrazolyl, benzofuranyl, and benzothienyl. Heteroaryl rings may be unsubstituted or substituted by one or more moieties as described for aryl above.

Exemplary monocyclic heterocyclic or heteroaryl groups also include, but are not limited to, pyrrolidinyl, oxetanyl, pyrazolinyl, imidazolinyl, imidazolidinyl, oxazolidinyl, isoxazolinyl, thiazolyl, thiadiazolyl, thiazolidinyl, isothiazolidinyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, and the like.

Exemplary bicyclic heterocyclic groups include, but are not limited to, indolyl, benzothiazolyl, benzoxazolyl, benzodioxolyl, benzothienyl, quinuclidinyl, tetra-hydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include, but are not limited to, carbazolyl, benzidolyl, phenanthrolinyl, acridinyl, phenanthridinyl, xanthenyl and the like.

Unless otherwise specifically noted or apparent by context, "active agent" or "active ingredient" or "therapeutic agent" as used in this specification, means a isoxazoline compound of the invention.

The term "locus" is intended to mean a habitat, breeding ground, area, material or environment in which a parasite is growing or may grow. The term "locus" does not include the body of an animal.

Synthesis of Compounds

The isoxazoline compounds of formula (I) may be prepared by processes described herein or by adaptation of these processes or process known in the art to prepare compounds with different substitution patterns. For example, the compounds of formula (I) and intermediates used in the processes to make the compounds may be prepared by processes adapted from those described in U.S. Pat. Nos. 7,964,204, 8,410,153, 8,217,180, 8,546,613, 7,662,972, 8,466,115, 8,383,659, 8,853,186, 8,618,126, US 2014/0371464, US 2015/0291612 and WO 2014/090918, all of which are incorporated herein by reference in their entirety.

Formation of carbon-carbon double bonds is a well-known reaction in organic chemistry and the double bond in the compounds of formula (I) may be formed using a variety of reactions. For example, one well-known reaction that may be used to form the alkene linking group in the compounds of formula (I) is the reaction of an aldehyde or ketone with a phosphorus ylide (the Wittig Reaction, see, for example page 845 in Advanced Organic Chemistry, $3^{rd}$ edition, by Jerry March, John Wiley & Sons, New York). Other well-known reactions may be utilized to form the carbon-carbon double bond in the compounds of formula (I), including, but not limited to, the reaction of an α-anion of a trialkylsilane with an aldehyde or ketone group (Peterson olefination) and the reaction of a phosphonate with an aldehyde or ketone (Horner-Emmons, Wadsworth-Emmons or Horner-Wadsworth-Emmons reaction).

Accordingly, Schemes 1 to 4 below describe one embodiment of the synthesis of certain compounds of formula (I) of the invention. Scheme 1 shows the preparation of two isoxazoline intermediates 1-4 and 1-6 that may be used to form a carbon-carbon double bond by reacting with a suitable aldehyde or ketone group HC(O)—Y-Q or RC(O)—Y-Q. Thus, compound 1-1 is reacted with 1-2 to form the alkoxycarbonyl-substituted isoxazoline intermediate 1-3. The ester group may then be reduced to the alcohol followed by oxidation to form aldehyde 1-4, which may be used as a reaction partner with a phosphorus ylide. Alternatively, intermediate 1-3 may be reduced and then brominated to form the ylide precursor 1-6. Compound 1-6 may be converted to an ylide which is reacted with a suitable aldehyde to form the desired carbon-carbon double bond.

In another embodiment, the reaction between compounds 1-1 and 1-2 depicted in Scheme 1 or similar variants may use a chiral phase transfer catalyst to form the isoxazoline ring in an enantioselective manner to provide the isoxazoline intermediate enriched in one enantiomer. Processes to prepare certain isoxazoline compounds enriched in an enantiomer using some cinchona alkaloid-derived phase transfer catalysts have been described. For example, US 2014/0206633 A1, US 2014/0350261 A1, WO 2013/116236 A1 and WO 2014/081800 A1, all incorporated herein by reference, describe the synthesis of certain isoxazoline active agents enriched in an enantiomer using cinchona alkaloid based chiral phase transfer catalysts. Further, Matoba et al., Angew. Chem. 2010, 122, 5898-5902 describes the chiral synthesis of certain pesticidal isoxazoline active agents.

Scheme 1

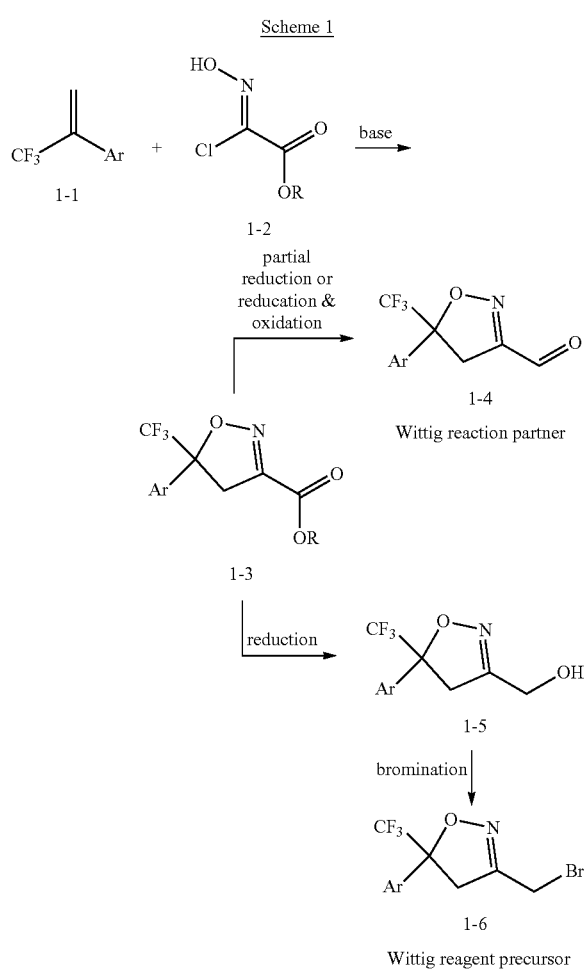

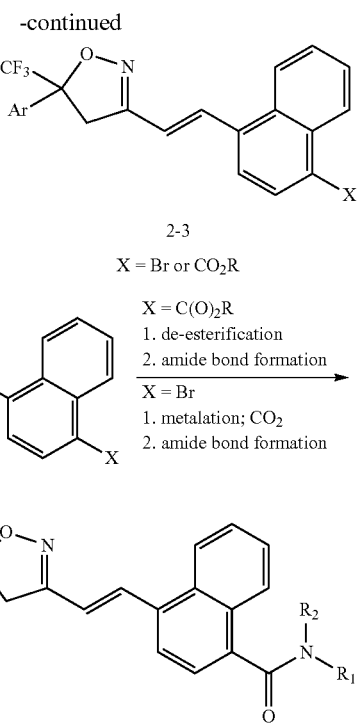

Scheme 2 below describes the synthesis of a compound of formula (I) where Y is Y-2 starting from intermediate 1-6. Reaction of bromo intermediate 1-6 with a suitable phosphine (e.g. triphenylphosphine) would provide a phosphorus ylide 2-1 which may be reacted with a suitably-substituted aldehyde, such as aldehyde 2-2, in the presence of a base to form the intermediate 2-3 with the desired carbon-carbon double bond. Compound 2-3 where X is either an ester group or a halogen such as Br may then be further elaborated as shown to provide the compound of formula (I)

Alternatively, the compounds of formula (I) may be prepared as shown in scheme 3 below for a compound of formula (I) where Y is Y-2 by reacting a suitably-substituted aryl ylide with an isoxazoline ring having an aldehyde or ketone substituent.

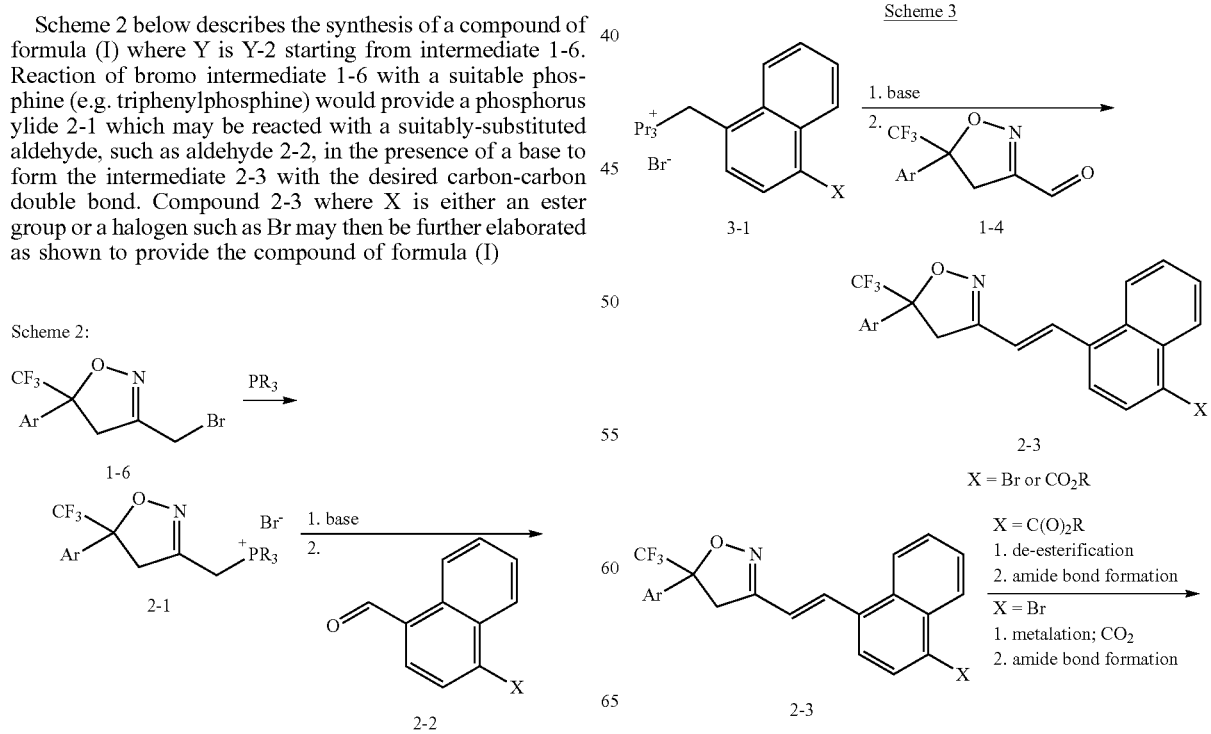

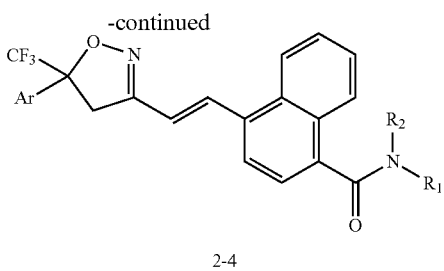

2-4

The aryl ylide compound 3-1 may be formed by reacting an aryl halomethyl compound, such as an aryl methylbromide, with a suitable phosphine (e.g. triphenylphosphine). Reaction of the ylide 3-1 with a suitably substituted aldehyde such as compound 1-4 in the presence of a base would form the desired double bond as in compound 2-3. Further elaboration of compound 2-3 (X is either halogen such as bromine or an ester group or equivalent) as shown would provide the desired compound 2-4.

A similar approach may be taken to prepare compounds of formula (I), wherein Y is Y-4. Synthesis of isoxazoline compounds having an indolizine ring or an imidazo[1,2-a]pyrimidine are described in U.S. Pat. No. 8,618,126 B2, which is incorporated herein by reference.

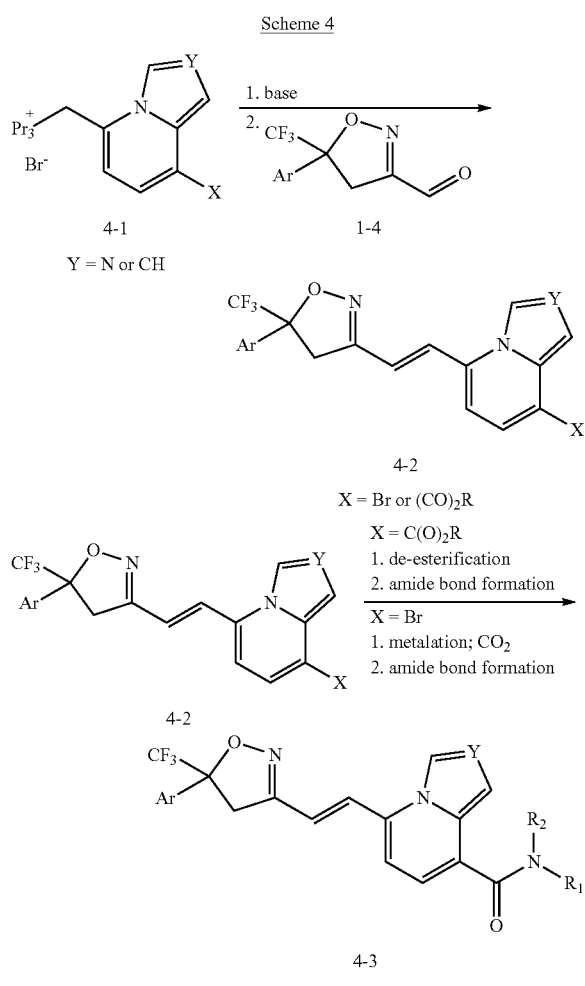

Thus, reaction of a suitably substituted indolizine or an imidazo[1,2-a]pyrimidine ylide 4-1 with aldehyde 1-4 in the presence of a base forms the compound 4-2 containing the desired carbon-carbon double bond. Further elaboration of this intermediate 4-2 provides compound 4-3.

It will be apparent to skilled persons in the art that the synthetic processes outlined in Schemes 1 to 4 above may be varied to incorporate different groups Y (e.g. substituted phenyl or other heteroaryl instead of naphthyl) to prepare alternate compounds of Formula (I) using the same types of transformation since the reactions shown are of broad scope.

Veterinary Compositions

Another aspect of the invention is the formation of parasiticidal compositions which comprise the isoxazoline compounds of the invention. The composition of the invention can also be in a variety of forms which include, but are not limited to, oral formulations, injectable formulations, and topical, dermal or subdermal formulations. The formulations are intended to be administered to an animal which includes but is not limited to mammals, birds and fish. Examples of mammals include but are not limited to humans, cattle, sheep, goats, llamas, alpacas, pigs, horses, donkeys, dogs, cats and other livestock or domestic mammals. Examples of birds include turkeys, chickens, ostriches and other livestock or domestic birds.

The composition of the invention may be in a form suitable for oral use, for example, as baits (see, e.g., U.S. Pat. No. 4,564,631, incorporated herein by reference), dietary supplements, troches, lozenges, chewables, tablets, hard or soft capsules, emulsions, aqueous or oily suspensions, aqueous or oily solutions, oral drench formulations, dispersible powders or granules, premixes, syrups or elixirs, enteric formulations or pastes. Compositions intended for oral use may be prepared according to any method known in the art for the manufacture of pharmaceutical compositions and such compositions may contain one or more agents selected from the group consisting of sweetening agents, bittering agents, flavoring agents, coloring agents and preserving agents in order to provide pharmaceutically elegant and palatable preparations.

Tablets may contain the active ingredient in admixture with non-toxic, pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc, the tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256,108; 4,166,452; and 4,265,874 (incorporated herein by reference) to form osmotic therapeutic tablets for controlled release.

Formulations for oral use may be hard gelatin capsules, wherein the active ingredient is mixed with an inert solid diluent, for example, calcium carbonate, calcium phosphate or kaolin. Capsules may also be soft gelatin capsules, wherein the active ingredient is mixed with water or miscible solvents such as propylene glycol, polyethylene glycols (PEGs) and ethanol, or an oil medium, for example peanut oil, liquid paraffin, or olive oil.

The compositions of the invention may also be in the form of oil-in-water or water-in-oil emulsions. The oily phase may be a vegetable oil, for example, olive oil or *Arachis* oil, or a mineral oil, for example, liquid paraffin or mixtures of these. Suitable emulsifying agents may be naturally-occurring phosphatides, for example, soybean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsions may also contain sweetening agents, bittering agents, flavoring agents, and/or preservatives.

In one embodiment of the formulation, the composition of the invention is in the form of a microemulsion. Microemulsions are well suited as the liquid carrier vehicle. Microemulsions are quaternary systems comprising an aqueous phase, an oily phase, a surfactant and a cosurfactant. They are translucent and isotropic liquids.

Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously.

In one embodiment of the oily phase, the oily phase can be formed from mineral or vegetable oils, from unsaturated polyglycosylated glycerides or from triglycerides, or alternatively from mixtures of such compounds. In one embodiment of the oily phase, the oily phase comprises of triglycerides; in another embodiment of the oily phase, the triglycerides are medium-chain triglycerides, for example $C_8$-$C_{10}$ caprylic/capric triglyceride. In another embodiment of the oily phase will represent a % v/v range selected from the group consisting of about 2 to about 15%; about 7 to about 10%; and about 8 to about 9% v/v of the microemulsion.

The aqueous phase includes, for example water or glycol derivatives, such as propylene glycol, glycol ethers, polyethylene glycols or glycerol. In one embodiment of the glycol derivatives, the glycol is selected from the group consisting of propylene glycol, diethylene glycol monoethyl ether, dipropylene glycol monoethyl ether and mixtures thereof. Generally, the aqueous phase will represent a proportion from about 1 to about 4% v/v in the microemulsion.

Surfactants for the microemulsion include diethylene glycol monoethyl ether, dipropyelene glycol monomethyl ether, polyglycolyzed $C_8$-$C_{10}$ glycerides or polyglyceryl-6 dioleate. In addition to these surfactants, the cosurfactants include short-chain alcohols, such as ethanol and propanol.

Some compounds are common to the three components discussed above, i.e., aqueous phase, surfactant and cosurfactant. However, it is well within the skill level of the practitioner to use different compounds for each component of the same formulation. In one embodiment for the amount of surfactant/cosurfactant, the cosurfactant to surfactant ratio will be from about 1/7 to about 1/2. In another embodiment for the amount of cosurfactant, there will be from about 25 to about 75% v/v of surfactant and from about 10 to about 55% v/v of cosurfactant in the microemulsion.

Oily suspensions may be formulated by suspending the active ingredient in a vegetable oil, for example, Arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as sucrose, saccharin or aspartame, bittering agents, and flavoring agents may be added to provide a palatable oral preparation. These compositions may be preserved by the addition of an antioxidant such as ascorbic acid, or other known preservatives.

Aqueous suspensions may contain the active material in admixture with excipients suitable for the manufacture of aqueous suspensions. Such excipients are suspending agents, for example, sodium carboxymethylcellulose, methylcellulose, hydroxy-propylmethylcellulose, sodium alginate, polvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents and/or bittering agents, such as those set forth above.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, may also be present.

Syrups and elixirs may be formulated with sweetening agents, for example, glycerol, propylene glycol, sorbitol or sucrose. Such formulations may also contain a demulcent, a preservative, flavoring agent(s) and/or coloring agent(s).

In another embodiment of the invention, the composition can be in paste form. Examples of embodiments in a paste form include but are not limited to those described in U.S. Pat. Nos. 6,787,342 and 7,001,889 (each of which are incorporated herein by reference). In addition to the isoxazoline compound of the invention, the paste can also contain fumed silica; a viscosity modifier; a carrier; optionally, an absorbent; and optionally, a colorant, stabilizer, surfactant, or preservative.

The process for preparing a paste formulation comprises the steps of:

(a) dissolving or dispersing the isoxazoline compound into the carrier by mixing;

(b) adding the fumed silica to the carrier containing the dissolved isoxazoline compound and mixing until the silica is dispersed in the carrier;

(c) allowing the intermediate formed in (b) to settle for a time sufficient in order to allow the air entrapped during step (b) to escape; and (d) adding the viscosity modifier to the intermediate with mixing to produce a uniform paste.

The above steps are illustrative, but not limiting. For example, step (a) can be the last step.

In one embodiment of the formulation, the formulation is a paste containing isoxazoline compound, fumed silica, a viscosity modifier, an absorbent, a colorant; and a hydrophilic carrier which is triacetin, a monoglyceride, a diglyceride, or a triglyceride.

The paste may also include, but is not limited to, a viscosity modifier including PEG 200, PEG 300, PEG 400, PEG 600, monoethanolamine, triethanolamine, glycerol, propylene glycol, polyoxyethylene (20) sorbitan monooleate (POLYSORBATE 80 or TWEEN 80), and poloxamers (e.g., PLURONIC L 81); an absorbent including magnesium carbonate, calcium carbonate, starch, and cellulose and its derivatives; and a colorant selected from the group consisting of titanium dioxide iron oxide, and FD&C Blue #1 ALUMINUM LAKE.

The compositions may be in the form of a sterile injectable aqueous or oleagenous suspension or an injectable solution. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol glycerol formal or polyethylene glycols may also be used. Preservatives, such as phenol or benzyl alcohol, may be used.

In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Topical, dermal and subdermal formulations can include emulsions, creams, ointments, gels, pastes, powders, shampoos, pour-on formulations, spot-on solutions and suspensions, dips and sprays. Topical application of an inventive compound or of a composition including at least one inventive compound among active agent(s) therein, in the form of a spot-on or pour-on composition, can allow for the inventive compound to be absorbed through the skin to achieve systemic levels, distributed through the sebaceous glands or on the surface of the skin achieving levels throughout the hair coat. When the compound is distributed through the sebaceous glands, they can act as a reservoir, whereby there can be a long-lasting effect (up to several months) effect. Spot-on formulations are typically applied in a localized region which refers to a relatively small area on the animal rather than to a large portion of the surface of the animal. In one embodiment of a localized region, the location is between the shoulders. In another embodiment of a localized region it is a stripe, e.g. a stripe from head to tail of the animal.

Pour-on formulations are described in U.S. Pat. No. 6,010,710, incorporated herein by reference. In some embodiments, the pour-on formulations may be oily, and generally comprise a diluent or vehicle and also a solvent (e.g. an organic solvent) for the active ingredient if the latter is not soluble in the diluent. In other embodiments, the pour-on formulations may be non-oily, including alcohol-based formulations.

Organic solvents that can be used in the invention include but are not limited to: acetyltributyl citrate, fatty acid esters such as the dimethyl ester, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone including N-methylpyrrolidone, diethylene glycol monoethyl ether, propylene glycol monomethyl ether, propylene glycol monoethyl ether, ethylene glycol, diisobutyl adipate, diisopropyl adipate (also known as CERAPHYL 230), triacetin, butyl acetate, octyl acetate, propylene carbonate, butylene carbonate, dimethylsulfoxide, organic amides including dimethylformamide and dimethylacetamide, and diethyl phthalate, or a mixture of at least two of these solvents.

In one embodiment of the invention, the pharmaceutically or veterinarily acceptable carrier of the formulation comprises $C_1$-$C_{10}$ alcohols or esters thereof (including acetates, such as ethyl acetate, butyl acetate and the like), $C_{10}$-$C_{18}$ saturated fatty acids or esters thereof, $C_{10}$-$C_{18}$ monounsaturated fatty acids or esters thereof, monoesters or diesters of aliphatic diacids, glycerol monoesters (e.g. monoglycerides), glycerol diesters (e.g. diglycerides), glycerol triesters (e.g. triglycerides such as triacetin), glycols, glycol ethers, glycol esters or glycol carbonates, polyethylene glycols of various grades (PEGs) or monoethers, diethers, monoesters or diesters thereof (e.g. diethylene glycol monoethyl ether), or mixtures thereof.

As vehicle or diluent, mention may be made of plant oils such as, but not limited to soybean oil, groundnut oil, castor oil, corn oil, cotton oil, olive oil, grape seed oil, sunflower oil, coconut oils etc.; mineral oils such as, but not limited to, petrolatum, paraffin, silicone, etc.; aliphatic or cyclic hydrocarbons or alternatively, for example, medium-chain (such as C8 to C12) triglycerides.

In another embodiment of the invention, an emollient and/or spreading and/or film-forming agent can be added. In one embodiment, the emollient and/or spreading and/or film-forming agent is those agents selected from the group consisting of:

(a) polyvinylpyrrolidone, polyvinyl alcohols, copolymers of vinyl acetate and vinylpyrrolidone, polyethylene glycols, benzyl alcohol, 2-pyrrolidones including, but not limited to N-methylpyrrolidone, mannitol, glycerol, sorbitol, polyoxyethylenated sorbitan esters; lecithin, sodium carboxymethylcellulose, silicone oils, polydiorganosiloxane oils (such as polydimethylsiloxane (PDMS) oils), for example those containing silanol functionalities, or a 45V2 oil, (b) anionic surfactants such as alkaline stearates, sodium, potassium or ammonium stearates; calcium stearate, triethanolamine stearate; sodium abietate; alkyl sulfates (e.g. sodium lauryl sulfate and sodium cetyl sulfate); sodium dodecylbenzenesulfonate, sodium dioctylsulphosuccinate; fatty acids (e.g. those derived from coconut oil), (c) cationic surfactants such as water-soluble quaternary ammonium salts of formula $N^+R'R''R'''R''''$, $Y^-$ in which the radicals R are optionally hydroxylated hydrocarbon radicals and $Y^-$ is an anion of a strong acid such as the halide, sulfate and sulfonate anions; cetyltrimethylammonium bromide is among the cationic surfactants which can be used, (d) amine salts of formula $N^+HR'R''R'''$ in which the radicals R are optionally hydroxylated hydrocarbon radicals; octadecylamine hydrochloride is among the cationic surfactants which can be used, (e) nonionic surfactants such as sorbitan esters, which are optionally polyoxyethylenated (e.g. POLYSORBATE 80), polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, (f) amphoteric surfactants such as the substituted lauryl compounds of betaine; or (g) a mixture of at least two of these agents.

The solvent will be used in proportion with the concentration of the isoxazoline compound and its solubility in this solvent. It will be sought to have the lowest possible volume. The vehicle makes up the difference to 100%.

In one embodiment of the amount of emollient, the emollient is used in a proportion of from 0.1 to 50% and 0.25 to 5%, by volume.

In another embodiment of the invention, the composition can be in ready-to-use solution for localized topical application, including a spot-on formulation, as is described in U.S. Pat. No. 6,395,765, incorporated herein by reference. In addition to the isoxazoline compound, the solution may contain a crystallization inhibitor, an organic solvent and an organic co-solvent.

In one embodiment of the amount of crystallization inhibitor, the crystallization inhibitor can be present in a proportion of about 1 to about 30% (w/v) in the composition. In other embodiments, the crystallization inhibitor may be present in a proportion of about 1 to about 20% (w/v) and about 5 to about 15%. Acceptable inhibitors are those whose addition to the formulation inhibits the formation of crystals when the formulation is applied. In some embodiments, formulations may include compounds that function as crystallization inhibitors other than those listed herein. In these embodiments, the suitability of a crystallization inhibitor may be determined by a the test in which 0.3 ml of a solution comprising 10% (w/v) of isoxazoline compound in the liquid carrier and 10% of the inhibitor are deposited on a glass slide at 20° C. and allowed to stand for 24 hours. The slide is then observed with the naked eye. Acceptable inhibitors are those whose addition provides for few (e.g. less than ten crystals) or no crystals.

In one embodiment, the organic solvent has a dielectric constant of about 2 to about 35, about 10 to about 35 or about 20 to about 30. In other embodiments, the solvent will have a dielectric constant of between about 2 and about 20, or between about 2 and about 10. The content of this organic solvent in the overall composition will complement to 100% of the composition.

As discussed above, the solvent may comprise a mixture of solvents including a mixture of an organic solvent and an organic co-solvent. In one embodiment, and the organic co-solvent has a boiling point of less than about 300° C. or less than about 250° C. In other embodiments, the co-solvent has a boiling point of below about 200° C., or below about 130° C. In still another embodiment of the invention, the organic co-solvent has a boiling point of below about 100° C., or below about 80° C. In still other embodiments, the organic co-solvent will have a dielectric constant of a range selected from the group consisting of about 2 to about 40, about 10 to about 40, or typically about 20 to about 30. In some embodiments of the invention, the co-solvent may be present in the composition in an organic co-solvent/organic solvent weight/weight (W/W) ratio of about 1/15 to about 1/2. In some embodiments, the co-solvent is volatile so as to act as a drying promoter, and is miscible with water and/or with the organic solvent.

The formulation can also comprise an antioxidizing agent intended to inhibit oxidation in air, this agent being present in a proportion selected from a range consisting of about 0.005 to about 1% (w/v) and about 0.01 to about 0.05%.

Crystallization inhibitors which are useful for the invention include but are not limited to:
(a) polyvinylpyrrolidone, polyvinyl alcohols, copolymers of vinyl acetate and of vinylpyrrolidone, polyethylene glycols of various grades, benzyl alcohol, 2-pyrrolidones including, but not limited to N-methylpyrrolidone, dimethylsulfoxide, mannitol, glycerol, sorbitol or polyoxyethylenated esters of sorbitan; lecithin or sodium carboxymethylcellulose; a solvent as described herein that is capable of inhibiting crystal formation; acrylic derivatives, such as acrylates and methacrylates or other polymers derived from acrylic monomers, and others;
(b) anionic surfactants, such as alkaline stearates (e.g. sodium, potassium or ammonium stearate); calcium stearate or triethanolamine stearate; sodium abietate; alkyl sulfates, which include but are not limited to sodium lauryl sulfate and sodium cetyl sulfate; sodium dodecylbenzenesulfonate or sodium dioctyl sulphosuccinate; or fatty acids (e.g. coconut oil);
(c) cationic surfactants, such as water-soluble quaternary ammonium salts of formula $N^+R'R''R'''R''''Y^-$, in which the R radicals are identical or different optionally hydroxylated hydrocarbon radicals and Y is an anion of a strong acid, such as halide, sulfate and sulfonate anions; cetyltrimethylammonium bromide is one of the cationic surfactants which can be used;
(d) amine salts of formula $N^+HR'R''R'''$, in which the R radicals are identical or different optionally hydroxylated hydrocarbon radicals; octadecylamine hydrochloride is one of the cationic surfactants which can be used;
(e) non-ionic surfactants, such as optionally polyoxyethylenated esters of sorbitan, e.g. POLYSORBATE 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide;
(f) amphoteric surfactants, such as substituted lauryl compounds of betaine; or
(g) a mixture of at least two of the compounds listed in (a)-(f) above.

In one embodiment of the crystallization inhibitor, a crystallization inhibitor pair will be used. Such pairs include, for example, the combination of a film-forming agent of polymeric type and of a surface-active agent. These agents will be selected from the compounds mentioned above as crystallization inhibitor.

In one embodiment of the film-forming agent, the agents are of the polymeric type which include but are not limited to the various grades of polyvinylpyrrolidone, polyvinyl alcohols, and copolymers of vinyl acetate and of vinylpyrrolidone.

In one embodiment of the surface-active agents, the agents include but are not limited to those made of non-ionic surfactants; in another embodiment of the surface active agents, the agent is a polyoxyethylenated esters of sorbitan and in yet another embodiment of the surface-active agent, the agents include the various grades of POLYSORBATE, for example POLYSORBATE 80.

In another embodiment of the invention, the film-forming agent and the surface-active agent can be incorporated in similar or identical amounts within the limit of the total amounts of crystallization inhibitor mentioned elsewhere.

In one embodiment of the antioxidizing agents, the agents are those conventional in the art and include but is not limited to butylated hydroxyanisole, butylated hydroxytoluene, ascorbic acid, sodium metabisulphite, propyl gallate, sodium thiosulfate or a mixture of not more than two of them.

The non-active formulation components discussed above are well known to the practitioner in this art and may be obtained commercially or through known techniques. These concentrated compositions are generally prepared by simple mixing of the constituents as defined above; advantageously, the starting point is to mix the active material in the main solvent and then the other ingredients are added.

The volume of the topical formulations applied is not restricted as long as the amount of substance administered is shown to be safe and efficacious. Typically, the volume applied depends on the size and weight of the animal as well as the concentration of active, the extent of infestation by parasites and the type of administration. In some embodiments, the volume applied can be of the order of about 0.3 to about 5 ml or about 0.3 ml to about 1 ml. In one embodiment for the volume, the volume is on the order of about 0.5 ml, for cats and on the order of about 0.3 to about 3 ml for dogs, depending on the weight of the animal. In other embodiments, the volume applied may be about 5 ml to about 10 ml, about 5 ml to about 15 ml, about 10 ml to about 20 ml, or about 20 ml to about 30 ml, depending on the size of the animal treated and the concentration of the active agent in the formulation, among other factors.

In another embodiment of the invention, application of a spot-on formulation according to the present invention can also provide long-lasting and broad-spectrum efficacy when the solution is applied to the mammal or bird. The spot-on formulations provide for topical administration of a concentrated solution, suspension, microemulsion or emulsion for intermittent application to a spot on the animal, generally between the two shoulders (solution of spot-on type).

For spot-on formulations, the carrier can be a liquid carrier vehicle as described in U.S. Pat. No. 6,426,333 (incorporated herein by reference). In one embodiment, the spot-on formulation comprises a solvent and a cosolvent wherein the solvent may be acetone, acetonitrile, benzyl alcohol, butyl diglycol, dimethylacetamide, dimethylformamide, dipropylene glycol n-butyl ether, propylene glycol monomethyl ether, propylene glycol monoethyl ether, diisobutyl adipate, diisopropyl adipate (also known as CERAPHYL 230), triacetin, butyl acetate, octyl acetate, propylene carbonate, butylene carbonate, dimethylsulfoxide, organic amides including dimethylformamide and dimethylacetamide, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone including N-methylpyrrolidone, diethylene glycol monoethyl ether, ethylene glycol, diethyl phthalate fatty acid esters, such as the diethyl ester or diisobutyl adipate, and a mixture of at least two of these solvents. In another embodiment, the spot-on formulations include a cosolvent that is absolute ethanol, isopropanol or methanol, or a mixture thereof. In another embodiment, the compositions include benzyl alcohol as a co-solvent.

In one embodiment of the invention, the pharmaceutically or veterinarily acceptable carrier of the formulation comprises $C_1$-$C_{10}$ alcohols or esters thereof (including acetates, such as ethyl acetate, butyl acetate and the like), $C_{10}$-$C_{18}$ saturated fatty acids or esters thereof, $C_{10}$-$C_{18}$ monounsaturated fatty acids or esters thereof, monoesters or diesters of aliphatic diacids, glycerol monoesters (e.g. monoglycerides), glycerol diesters (e.g. diglycerides), glycerol triesters (e.g. triglycerides such as triacetin), glycols, glycol ethers, glycol esters or glycol carbonates, polyethylene glycols of various grades (PEGs) or monoethers, diethers, monoesters or diesters thereof (e.g. diethylene glycol monoethyl ether), or mixtures thereof.

The liquid carrier vehicle can optionally contain a crystallization inhibitor including an anionic surfactant, a cationic surfactant, a non-ionic surfactant, an amine salt, an amphoteric surfactant or polyvinylpyrrolidone, polyvinyl alcohols, copolymers of vinyl acetate and vinylpyrrolidone, 2-pyrrolidone including N-methylpyrrolidone (NMP), dimethylsulfoxide, polyethylene glycols, benzyl alcohol, mannitol, glycerol, sorbitol, polyoxyethylenated sorbitan esters; lecithin, sodium carboxymethylcellulose, solvents as defined herein that can inhibit the formation of crystals, and acrylic derivatives such acrylates or methacrylates as well as other polymers derived from acrylic monomers, or a mixture of these crystallization inhibitors.

Spot-on formulations may be prepared by dissolving the active ingredients into the pharmaceutically or veterinary acceptable vehicle. Alternatively, the spot-on formulation can be prepared by encapsulation of the active ingredient to leave a residue of the therapeutic agent on the surface of the animal. These formulations will vary with regard to the weight of the therapeutic agent in the combination depending on the species of host animal to be treated, the severity and type of infection and the body weight of the host.

Dosage forms may contain from about 0.5 mg to about 5 g of an active agent. In one embodiment of the dosage form, the dosage is from about 1 mg to about 500 mg of an active agent. More typically the dosage is about 1 mg to about 25 mg, 1 mg to about 50 mg, 10 mg to about 100 mg, or 20 mg to about 200 mg. In other embodiments, the dosage is about 50 mg to about 300 mg, 50 mg to about 400 mg, 50 mg to about 500 mg, 50 mg to about 600 mg, 50 mg to about 800 mg, or 100 mg to about 1000 mg.

In one embodiment of the invention, the active agent is present in the formulation at a concentration of about 0.05% to about 50% weight/volume. In other embodiments, the active agent may be present in the formulation at a concentration of about 0.1% to about 30%, about 0.5% to about 20% (w/v) or about 1% to about 10% (w/v). In another embodiment of the invention, the active agent is present in the formulation as a concentration from about 0.1 to 2% weight/volume. In yet another embodiment of the invention, the active agent is present in the formulation as a concentration from about 0.25 to about 1.5% weight/volume. In still another embodiment of the invention, the active agent is present in the formulation as a concentration about 1% weight/volume.

In a particular advantageous embodiment of the invention, the dose of the inventive compounds is about 0.01 mg/kg to about 100 mg/kg of weight of animal. In another embodiment, the dose is about 0.1 mg/kg to about 100 mg/kg of weight of animal. In other embodiments, the dose of the inventive compounds is about 0.5 mg/kg to about 70 mg/kg, about 0.5 mg/kg to about 50 mg/kg or about 0.5 mg/kg to about 30 mg/kg. In other preferred embodiments, the dose is 0.5 mg/kg to about 30 mg/kg, 0.5 mg/kg to about 20 mg/kg or 0.5 mg/kg to about 10 mg/kg. More typically, in some embodiments the dose of the active compounds is about 0.01 mg/kg to 5 mg/kg, 0.1 mg/kg to about 5 mg/kg, about 0.1 mg/kg to about 3 mg/kg, or about 0.1 mg/kg to 1.5 mg/kg. In still other embodiments of the invention, the dose may be as low as 0.1 mg/kg (0.02 mg/ml), about 0.2 mg/kg (0.04 mg/ml), about 0.3 mg/kg (0.06 mg/ml), about 0.4 mg/kg (0.08 mg/ml), about 0.5 mg/kg (0.1 mg/ml), about 0.6 mg/kg (0.12 mg/ml), about 0.7 mg/kg (0.14 mg/ml), about 0.8 mg/kg (0.16 mg/ml), about 0.9 mg/kg (0.18 mg/ml), about 1.0 mg/kg (0.2 mg/ml).

Agricultural Compositions

The compounds of formula (I), or agriculturally acceptable salts thereof, can be formulated in various ways, depending on the prevailing biological and/or chemico-physical parameters. Examples of possible formulations which are suitable are: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), dispersions on an oil or water basis, solutions which are miscible with oil, capsule suspensions (CS), dusts (DP), seed-dressing products, granules for broadcasting and soil application, granules (GR) in the form of microgranules, spray granules, coated granules and adsorption granules, water-dispersible granules (WG), water-soluble granules (SG), ULV formulations, microcapsules and waxes.

Solid state forms of the compounds of formula (I) can be prepared by methods known in the art, e.g. Bym et al., "Solid-State Chemistry of Drugs", $2^{nd}$ Edition, SSCI Inc., (1999); Glusker et al., "Crystal Structure Analysis—A Primer", $2^{nd}$ Edition, Oxford University Press, (1985).

The formulations mentioned can be prepared in a manner known per se, for example by mixing the active compounds with at least one solvent or diluent, emulsifier, dispersant and/or binder or fixative, water repellent and optionally one or more of a desiccant, UV stabilizer, a colorant, a pigment and other processing auxiliaries.

These individual formulation types are known in principle and described, for example, in: Winnacker-Küchler, "Chemische Technologie" [Chemical Technology], Volume 7, C. Hauser Verlag, Munich, 4th Edition 1986; Wade van Valkenburg, "Pesticide Formulations", Marcel Dekker, N.Y., 1973; K. Martens, "Spray Drying Handbook", 3rd Ed. 1979, G. Goodwin Ltd. London.

The necessary formulation auxiliaries such as inert materials, surfactants, solvents and other additives are also known and described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzflachenaktive Athylenoxidaddukte" [Surface-active ethylene oxide adducts], Wiss. Verlagsgesell., Stuttgart 1976; Winnacker-Küchler, "Chemische Technologie" [Chemical Technology], Volume 7, C. Hauser Verlag, Munich, 4th Ed. 1986.

Wettable powders are preparations which are uniformly dispersible in water and which, besides the compounds of formula (I), also comprise ionic and/or nonionic surfactants (wetters, dispersants), for example, polyoxyethylated alkylphenols, polyoxyethylated fatty alcohols, polyoxyethylated fatty amines, fatty alcohol polyglycol ether sulfates, alkanesulfonates or alkylbenzenesulfonates, sodium lignosulfonate, sodium 2,2'-dinaphthylmethane-6,6'-disulfonate, sodium dibutylnaphthalenesulfonate or else sodium oleoylmethyltaurinate, in addition to a diluent or inert substance. To prepare the wettable powders, the compounds of formula (I) are, for example, ground finely in conventional apparatuses such as hammer mills, blower mills and air-jet mills and mixed with the formulation auxiliaries, either concomitantly or thereafter.

Emulsifiable concentrates are prepared, for example, by dissolving the compounds of formula (I) in an organic solvent, for example butanol, cyclohexanone, dimethylformamide, xylene or else higher-boiling aromatics or hydrocarbons or mixtures of these, with addition of one or more ionic and/or nonionic surfactants (emulsifiers). Emulsifiers which can be used are, for example: calcium salts of alkylarylsulfonic acids, such as calcium dodecylbenzenesulfonate or nonionic emulsifiers, such as fatty acid polyglycol esters, alkylaryl polyglycol ethers, fatty alcohol polyglycol ethers, propylene oxide/ethylene oxide condensates, alkyl polyethers, sorbitan esters such as sorbitan fatty acid esters or polyoxyethylene sorbitan esters such as polyoxyethylene sorbitan fatty acid esters.

Dusts are obtained by grinding the active substance with finely divided solid substances, for example talc or natural clays, such as kaolin, bentonite or pyrophyllite, or diatomaceous earth.

Suspension concentrates may be water- or oil-based. They can be prepared, for example, by wet grinding by means of commercially available bead mills, if appropriate with addition of surfactants, as they have already been mentioned above for example in the case of the other formulation types.

Emulsions, for example oil-in-water emulsions (EW), can be prepared for example by means of stirrers, colloid mills and/or static mixtures using aqueous organic solvents and, if appropriate, surfactants as they have already been mentioned above for example in the case of the other formulation types.

Granules can be prepared either by spraying the compounds of formula (I) onto adsorptive, granulated inert material or by applying active substance concentrates onto the surface of carriers such as sand, kaolinites or of granulated inert material, by means of binders, for example polyvinyl alcohol, sodium polyacrylate or alternatively mineral oils. Suitable active substances can also be granulated in the manner which is conventional for the production of fertilizer granules, if desired in a mixture with fertilizers.

Water-dispersible granules are prepared, as a rule, by the customary processes such as spray-drying, fluidized-bed granulation, disk granulation, mixing in high-speed mixers and extrusion without solid inert material. To prepare disk, fluidized-bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, p. 8-57. In general, the agrochemical preparations comprise a range selected from the group consisting of about 0.1 to about 99% by weight and about 0.1 to about 95% by weight, of compounds of formula (I).

The concentration of compounds of formula (I) in wettable powders is, for example, about 10 to about 90% by weight, the remainder to 100% by weight being composed of customary formulation components. In the case of emulsifiable concentrates, the concentration of compounds of formula (I) can amount to ranges selected from the group consisting of about 1% to about 90% and about 5% to about 80% by weight. Formulations in the form of dusts usually comprise in the range selected from the group consisting of about 1% to about 30% by weight of compounds of formula (I) and about 5% to about 20% by weight of compounds of formula (I). For sprayable solutions comprise a range selected from the group consisting of about 0.05% to about 80% by weight of compounds of formula (I) and about 2% to about 50% by weight of compounds of formula (I). In the case of water-dispersible granules, the content of compounds of formula (I) depends partly on whether the compounds of formula (I) are in liquid or solid form and on which granulation auxiliaries, fillers and the like are being used. The water-dispersible granules, for example, comprise a range selected from the group consisting of between about 1 and about 95% and between about 10% and about 80% by weight.

In addition, the formulations of compounds of formula (I) mentioned comprise, if appropriate, the adhesives, wetters, dispersants, emulsifiers, penetrants, preservatives, antifoams, evaporation inhibitors, pH regulators and viscosity regulators which are conventional in each case.

The following are examples of agricultural compositions:
1. Products for dilution with water. For seed treatment purposes, such products may be applied to the seed diluted or undiluted.

A) Water-Soluble Concentrates
10 parts by weight of the active compound is dissolved in 90 parts by weight of water or a water-soluble solvent. As an alternative, wetters or other auxiliaries are added. The active compound dissolves upon dilution with water, whereby a formulation with 10% (w/w) of active compound is obtained.

B) Dispersible Concentrates (DC)
20 parts by weight of the active compound is dissolved in 70 parts by weight of cyclohexanone with addition of 10 parts by weight of a dispersant, for example polyvinylpyrrolidone. Dilution with water gives a dispersion, whereby a formulation with 20% (w/w) of active compounds is obtained.

C) Emulsifiable Concentrates (EC)
15 parts by weight of the active compounds is dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compounds is obtained.

D) Emulsions
25 parts by weight of the active compound is dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound is obtained.

E) Suspensions
In an agitated ball mill, 20 parts by weight of the active compound is comminuted with addition of 10 parts by weight of dispersants, wetters and 70 parts by weight of water or of an organic solvent to give a fine active compound suspension. Dilution with water gives a stable suspension of the active compound, whereby a formulation with 20% (w/w) of active compound is obtained.

F) Water-Dispersible Granules and Water-Soluble Granules (WG, SG)
50 parts by weight of the active compound is ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound, whereby a formulation with 50% (w/w) of active compound is obtained.

G) Water-Dispersible Powders and Water-Soluble Powders
75 parts by weight of the active compound are ground in a rotor-stator mill with addition of 25 parts by weight of dispersants, wetters and silica gel. Dilution with water gives a stable dispersion or solution of the active compound, whereby a formulation with 75% (w/w) of active compound is obtained.

H) Gel-Formulation (GF)
In an agitated ball mill, 20 parts by weight of the active compound is comminuted with addition of 10 parts by weight of dispersants, 1 part by weight of a gelling agent wetters and 70 parts by weight of water or of an organic solvent to give a fine active compound suspension. Dilution with water gives a stable suspension of the active compound, whereby a formulation with 20% (w/w) of active compound is obtained.

2. Products to be applied undiluted for foliar applications. For seed treatment purposes, such products may be applied to the seed diluted or undiluted.

I) Dustable Powders
5 parts by weight of the active compound are ground finely and mixed intimately with 95 parts by weight of finely divided kaolin. This gives a dustable product having 5% (w/w) of active compound.

J) Granules
0.5 part by weight of the active compound is ground finely and associated with 95.5 parts by weight of carriers, whereby a formulation with 0.5% (w/w) of active compound is obtained. Current methods are extrusion, spray-drying or the fluidized bed. This gives granules to be applied undiluted for foliar use.

K) ULV Solutions (UL)
10 parts by weight of the active compound is dissolved in 90 parts by weight of an organic solvent, for example xylene. This gives a product having 10% (w/w) of active compound, which is applied undiluted for foliar use.

Methods of Treatment

In another aspect of the invention, a method for preventing or treating a parasite infestation/infection in an animal is provided, comprising administering to the animal at least one compound of formula (I), optionally together with a pharmaceutically acceptable carrier. The compounds of the invention have long-lasting efficacy against ectoparasites (e.g. fleas and ticks) and in certain embodiments, when combined with an appropriate endoparasiticide, may also active against endoparasites that harm animals.

In one embodiment of the invention, methods for the treatment or prevention of a parasitic infestation or infection in a domestic animal are provided, which comprise administering to the animal an effective amount of at least one isoxazoline active agent of the invention to the animal. Ectoparasites against which the methods and compositions of the invention are effective include, but are not limited to, fleas, ticks, mites, mosquitoes, flies and lice. In certain embodiments wherein the compositions include one or more additional active agents that are active against internal parasites, the compositions and methods of the invention may also be effective against endoparasites including, but not limited to, cestodes, nematodes, hookworms and roundworms of the digestive tract of animals and humans. In one embodiment for treatment against ectoparasites, the ectoparasite is one or more insect or arachnid including those of the genera *Ctenocephalides, Rhipicephalus, Dermacentor, Ixodes, Boophilus, Amblyomma, Haemaphysalis, Hyalomma, Sarcoptes, Psoroptes, Otodectes, Chorioptes, Hypoderma, Damalinia, Linognathus, Haematopinus, Solenopotes, Trichodectes,* and *Felicola*.

In another embodiment for the treatment against ectoparasites, the ectoparasite is from the genera *Ctenocephalides, Rhipicephalus, Dermacentor, Ixodes* and/or *Boophilus*. The ectoparasites treated include but are not limited to fleas, ticks, mites, mosquitoes, flies, lice, blowfly and combinations thereof. Specific examples include, but are not limited to, cat and dog fleas (*Ctenocephalides felis, Ctenocephalides* sp. and the like), ticks (*Rhipicephalus* sp., *Ixodes* sp., *Dermacentor* sp., *Amblyomma* sp. and the like), and mites (*Demodex* sp., *Sarcoptes* sp., *Otodectes* sp. and the like), lice (*Trichodectes* sp., *Cheyletiella* sp., *Linognathus* sp., and the like), mosquitoes (*Aedes* sp., *Culex* sp., *Anopheles* sp., and the like) and flies (*Haematobia* sp. including *Haematobia irritans*, *Musca* sp., *Stomoxys* sp. including *Stomoxys calcitrans*, *Dermatobia* sp., *Cochliomyia* sp., and the like).

Additional examples of ectoparasites include but are not limited to the tick genus *Boophilus*, especially those of the species *microplus* (cattle tick), *decoloratus* and *annulatus*; myiasis such as *Dermatobia hominis* (known as Berne in Brazil) and *Cochliomyia hominivorax* (greenbottle); sheep myiasis such as *Lucilia sericata*, *Lucilia cuprina* (known as blowfly strike in Australia, New Zealand and South Africa). Flies proper, namely those whose adult constitutes the parasite, such as *Haematobia irritans* (horn fly) and *Stomoxys calcitrans* (stable fly); lice such as *Linognathus vituli*, etc.; and mites such as *Sarcoptes scabiei* and *Psoroptes ovis*. The above list is not exhaustive and other ectoparasites are well known in the art to be harmful to animals and humans. These include, for example migrating dipterous larvae.

In some embodiments of the invention, the composition can also be used to treat against endoparasites such as those helminths selected from the group consisting of *Anoplocephala*, *Ancylostoma*, *Necator*, *Ascaris*, *Capillaria*, *Cooperia*, *Dipylidium*, *Dirofilaria*, *Echinococcus*, *Enterobius*, *Fasciola*, *Haemonchus*, *Oesophagostomum*, *Ostertagia*, *Toxocara*, *Strongyloides*, *Toxascaris*, *Trichinella*, *Trichuris*, and *Trichostrongylus*, among others.

In one embodiment, the invention provides methods for the treatment and prevention of parasitic infections and infestations of animals (either wild or domesticated), including livestock and companion animals such as cats, dogs, horses, birds including chickens, sheep, goats, pigs, turkeys and cattle, with the aim of ridding these hosts of parasites commonly encountered by such animals.

In a preferred embodiment, the invention provides methods for the treatment or prevention of parasitic infections and infestations in companion animals including, but not limited to, cats and dogs. The methods of the invention are particularly effective for preventing or treating parasitic infestations of cats and dogs with fleas and ticks. In another preferred embodiment, the methods of the invention are used for the treatment or prevention of parasitic infections and infestations in cattle or sheep. When treating livestock animals such as cattle or sheep, the methods and compositions are particularly effective against *Rhipicephalus* (*Boophilus*) *microplus*, *Haematobia irritans* (horn fly), *Stomoxys calcitrans* (stable fly), and sheep myiasis such as *Lucilia sericata*, *Lucilia cuprina* (known as blowfly strike in Australia, New Zealand and South Africa).

The terms "treating" or "treat" or "treatment" are intended to mean the application or administration of an isoxazoline compound of the invention to an animal that has a parasitic infestation for the eradication of the parasite or the reduction of the number of the parasites infesting the animal undergoing treatment. It is noted that the compositions of the invention comprising an isoxazoline compound together with a pharmaceutically acceptable carrier may be used to prevent such a parasitic infestation.

The compounds and compositions of the invention are administered in parasiticidally effective amounts which are which are suitable to control the parasite in question to the desired extent, as described below. In each aspect of the invention, the compounds and compositions of the invention can be applied against a single pest or combinations thereof. The compounds and compositions of the invention may be administered continuously, for treatment or prevention of parasitic infections or infestations. In this manner, an effective amount of the active isoxazoline compounds of the invention are delivered to the animal in need thereof to control the target parasites. By "effective amount" is intended a sufficient amount of a composition of the invention to eradicate or reduce the number of parasites infesting the animal. In one embodiment, an effective amount of the active agent achieves at least 70% efficacy against the target parasite compared to a negative control according to known methods used in the art (animal not treated or treated with a placebo). In other embodiments, an effective amount of the active agent achieves at least 80%, or at least 90% efficacy against the target pests. Preferably, an effective amount of the active agent will achieve at least 95% efficacy against the target pests. In some embodiments, an effective amount of the compounds and compositions of the invention achieve at least 98% or 100% efficacy against the target parasites.

Generally, a dose of from about 0.001 to about 100 mg per kg of body weight given as a single dose or in divided doses for a period of from 1 to 5 days will be satisfactory but, of course, there can be instances where higher or lower dosage ranges are indicated, and such are within the scope of this invention. It is well within the routine skill of the practitioner to determine a particular dosing regimen for a specific host and parasite.

In some embodiments for companion animals, the dose of the isoxazoline active agent administered is between about 0.1 to about 30 mg per kg of body weight. More typically the dose of the isoxazoline active agent administered is about 0.5 to about 20 mg/kg or about 0.5 to about 15 mg/kg body weight. Preferably, the dose of the isoxazoline active agent administered is about 0.5 to about 10 mg/kg, about 0.5 to about 8 mg/kg or about 0.5 to about 5 mg/kg of body weight.

In certain embodiments for the treatment and prevention of parasite infestations and infections in smaller animals (e.g. cats and other smaller mammals), the dose of the isoxazoline active agent administered will be about 0.5 to about 2 mg/kg of body weight, preferably about 1 mg/kg of bodyweight. In other embodiments for the very long lasting treatment and protection of smaller animals against parasitic infestations or infections a dose of about 2 to about 15 mg/kg of bodyweight or preferably about 5 to about 15 mg/kg of bodyweight will be administered.

In some embodiments for the treatment and protection of dogs from parasitic infestations and infections, a dose of about 2 to about 15 mg/kg of bodyweight of the isoxazoline active agent will be administered. In other embodiments, a dose of about 2 to about 8 mg/kg or about 2 to about 5 mg/kg of bodyweight will be administered. In other embodiments for the treatment of livestock animals such as cattle or sheep, doses of the isoxazoline active agent administered may be about 1 to about 30 mg/kg of body weight. More typically the doses administered will be about 1 to about 20 mg/kg or about 1 to about 15 mg/kg. Preferably, a dose of the isoxazoline active agent administered to livestock animals will be about 1 to about 10 mg/kg of body weight.

Higher amounts may be provided for very prolonged release in or on the body of the animal. In another treatment embodiment, the amount of active agents for birds and other animals which are small in size is greater than about 0.01 mg/kg, and in another embodiment for the treatment of small-sized birds and other animals, the amount of is between about 0.01 and about 20 mg/kg of weight of animal. More typically the dose of the isoxazoline for small-sized animals and birds is about 0.5 to about 15 mg/kg, about 0.5 to about 10 mg/kg of body weight, or about 0.5 mg/kg to about 5 mg/kg of body weight.

In one embodiment of the method of use in dogs or cats, a composition comprising an isoxazoline compound of the invention has an efficacy against fleas and/or ticks of at least about 90.0% or higher for about 1 month, or longer. In another embodiment, the compositions of the invention provide an efficacy against fleas and/or ticks of at least 95.0% or higher for about 30 days, or longer.

In another embodiment, the compounds and compositions of the invention provide an efficacy against fleas and/or ticks in cats and dogs of at least about 80% for two months, or longer. In another embodiment, the compounds and compositions provide efficacy against fleas and/or ticks in cats and dogs of about 90% for about two months, or longer. In still another embodiment, the compounds and compositions provide an efficacy of about 95% for about 2 months or longer. In other embodiments, the compounds and composition provide longer-lasting efficacy against fleas and/or ticks including for about 3 months, or longer. In one embodiment of the invention, the isoxazoline compounds may be administered in the form of topical compositions to the animal. Topical compositions include dips, shampoos, sprays, spot-ons, pour-ons, and the like. Application of topical compositions is to animals to control parasites is well known in the art.

In some embodiments, the isoxazoline compounds may be administered in solutions using any means known in the art, including using an applicator gun or a metering flask, pipette, syringes, roll on, droppers, capsules, foil packages, vials, twist tip containers, metered-dose aerosols or sprays and other single dose and multi-dose containers.

In another aspect of the invention, a kit for the treatment or prevention of a parasitic infestation in an animal is provided, which comprises at least one isoxazoline active agent of the invention together with a pharmaceutically acceptable carrier and a dispensing device for application of the composition. The dispensing device may be a pipette, syringes, roll on, droppers, capsules, foil packages, vials, twist tip containers, metered-dose aerosols or sprays and other single dose and multi-dose containers, which includes an effective dose of each active agent in the pharmaceutically acceptable carrier or diluent.

In another embodiment of the invention, the compounds and compositions of the invention are suitable for controlling pests at a locus. Therefore, an additional embodiment of the invention is a method for controlling pests at a locus, comprising applying a pesticidally effective amount of compound of formula (I) or a composition comprising the compound to the locus. Pests that may be controlled with the compounds of the invention include insects such as *Blatella germanica, Heliothis virescens, Leptinotarsa decemlineata, Tetramorium caespitum* and combinations thereof.

In still another embodiment, the compounds and compositions of the invention are effective for protecting crops, plants and material made from wood against pests. Thus, the invention provides a method for protecting crops, plants, plant propagation material and material made from wood from pests that harm these materials comprising applying the compounds of the invention or compositions comprising the compounds to the crops, plants, plant propagation material and material made from wood.

In other embodiments, the compounds and compositions of the invention may be used against the phytoparasitic nematodes including, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

In addition, the compounds and compositions of the invention can also be used against pests which include, but are not limited to, the following pests:

(1) from the order of Isopoda, for example *Oniscus asellus, Armadillidium vulgare* and *Porcellio scaber;*

(2) from the order of Diplopoda, for example *Blaniulus guttulatus;*

(3) from the order of Chilopoda, for example *Geophilus carpophagus* and *Scutigera* spp.;

(4) from the order of Symphyla, for example *Scutigerella immaculata;*

(5) from the order of Thysanura, for example *Lepisma saccharina;*

(6) from the order of Collembola, for example *Onychiurus armatus;*

(7) from the order of Blattaria, for example *Blatta orientalis, Periplaneta americana, Leucophaea maderae* and *Blattella germanica;*

(8) from the order of Hymenoptera, for example *Diprion* spp., *Hoplocampa* spp., *Lasius* spp., *Monomorium pharaonis* and *Vespa* spp.;

(9) from the order of Siphonaptera, for example *Xenopsylla cheopis* and *Ceratophyllus* spp.;

(10) from the order of Anoplura (Phthiraptera), for example, *Damalinia* spp., *Haematopinus* spp., *Linognathus* spp., *Pediculus* spp., *Trichodectes* spp.;

(11) from the class of Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici;*

(12) from the class of Bivalva, for example, *Dreissena* spp.;

(13) from the order of Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.;

(14) from the order of Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga*, *Culex* spp., *Cuterebra* spp., *Dacus oleae*, *Dermatobia hominis*, *Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit*, *Pegomyia hyoscyami*, *Phorbia* spp., *Stomoxys* spp., *Tabanus* spp., *Tannia* spp., *Tipula paludosa*, *Wohlfahrtia* spp.;

(15) from the class of Gastropoda, for example, *Arion* spp., *Biomphalaria* spp., *Bulinus* spp., *Deroceras* spp., *Galba* spp., *Lymnaea* spp., *Oncomelania* spp., *Succinea* spp.;

(16) from the class of helminths, for example, *Ancylostoma duodenale*, *Ancylostoma ceylanicum*, *Acylostoma braziliensis*, *Ancylostoma* spp., *Ascaris lumbricoides*, *Ascaris* spp., *Brugia malayi*, *Brugia timori*, *Bunostomum* spp., *Chabertia* spp., *Clonorchis* spp., *Cooperia* spp., *Dicrocoelium* spp, *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Strongyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichiura*, *Wuchereria bancrofti*;

(17) from the order of Heteroptera, for example, *Anasa tristis*, *Antestiopsis* spp., *Blissus* spp., *Calocoris* spp., *Campylomma livida*, *Cavelerius* spp., *Cimex* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Nezara* spp., *Oebalus* spp., *Pentomidae*, *Piesma quadrata*, *Piezodorus* spp., *Psallus seriatus*, *Pseudacysta persea*, *Rhodnius* spp., *Sahlbergella singularis*, *Scotinophora* spp., *Stephanitis nashi*, *Tibraca* spp., *Triatoma* spp.;

(18) from the order of Homoptera, for example, *Acyrthosipon* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma piri*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephalafulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus*, *Geococcus coffeae*, *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva fimbriolata*, *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii*;

(19) from the order of Isoptera, for example, *Reticulitermes* spp., *Odontotermes* spp.;

(20) from the order of Lepidoptera, for example, *Acronicta major*, *Aedia leucomelas*, *Agrotis* spp., *Alabama argillacea*, *Anticarsia* spp., *Barathra brassicae*, *Bucculatrix thurberiella*, *Bupalus piniarius*, *Cacoecia podana*, *Capua reticulana*, *Carpocapsa pomonella*, *Cheimatobia brumata*, *Chilo* spp., *Choristoneurafumiferana*, *Clysia ambiguella*, *Cnaphalocerus* spp., *Earias insulana*, *Ephestia kuehniella*, *Euproctis chrysorrhoea*, *Euxoa* spp., *Feltia* spp., *Galleria mellonella*, *Helicoverpa* spp., *Heliothis* spp., *Hofmannophila pseudospretella*, *Homona magnanima*, *Hyponomeuta padella*, *Laphygma* spp., *Lithocolletis blancardella*, *Lithophane antennata*, *Loxagrotis albicosta*, *Lymantria* spp., *Malacosoma neustria*, *Mamestra brassicae*, *Mocis repanda*, *Mythimna separata*, *Oria* spp., *Oulema oryzae*, *Panolis flammea*, *Pectinophora gossypiella*, *Phyllocnistis citrella*, *Pieris* spp., *Plutella xylostella*, *Prodenia* spp., *Pseudaletia* spp., *Pseudoplusia includens*, *Pyrausta nubilalis*, *Spodoptera* spp., *Thermesia gemmatalis*, *Tinea pellionella*, *Tineola bisselliella*, *Tortrix viridana*, *Trichoplusia* spp.;

(21) from the order of Orthoptera, for example, *Acheta domesticus*, *Blatta orientalis*, *Blattella germanica*, *Gryllotalpa* spp., *Leucophaea maderae*, *Locusta* spp., *Melanoplus* spp., *Periplaneta americana*, *Schistocerca gregaria*;

(22) from the order of Thysanoptera, for example, *Baliothrips biformis*, *Enneothrips flavens*, *Frankliniella* spp., *Heliothrips* spp., *Hercinothrips femoralis*, *Kakothrips* spp., *Rhipiphorothrips cruentatus*, *Scirtothrips* spp., *Taeniothrips cardamoni*, *Thrips* spp.;

(23) from the class of Protozoa, for example, *Eimeria* spp.

Active Agent Combinations

The isoxazoline compounds of the invention or their salts can be employed as such or in the form of their preparations (formulations) as combinations with other active substances. For agricultural uses, the isoxazoline compounds of the invention may be used in combination with, for example, insecticides, attractants, sterilants, acaricides, nematicides, herbicides, fungicides, and with safeners, fertilizers and/or growth regulators, for example as a premix/readymix.

Classifications of fungicides are well-known in the art and include classifications by FRAC (Fungicide Resistance Action Committee). Fungicides which may optionally be admixed with the isoxazoline compounds of the invention include, but are not limited to, methyl benzimidazole carbamates, such as benzimidazoles and thiophanates; dicarboximides; demethylation inhibitors, such as imidazoles, piperazines, pyridines, pyrimidines, and triazoles; phenylamides, such as acylalanines, oxazolidinones, and butyrolactones; amines, such as morpholines, piperidines, and spiroketalamines; phosphorothiolates; dithiolanes; carboxamides; hydroxy-(2-amino-)pyrimidines; anilino-pyrimidines; N-phenyl carbamates; quinone outside inhibitors; phenylpyrroles; quinolines; aromatic hydrocarbons; heteroaromatics; melanin biosynthesis inhibitors-reductase; melanin biosynthesis inhibitors-dehydratase; hydroxyanilides (SBI class III), such as fenhexamid; SBI class IV, such as thiocarbamates and allylamines; polyoxins; phenylureas; quinone inside inhibitors; benzamides; enopyranuronic acid antibiotic; hexopyranosyl antibiotic; glucopyranosyl antibiotic; glucopyranosyl antibiotic; cyanoacetamideoximes; carbamates; uncoupler of oxidative phosphorylation; organo tin compounds; carboxylic acids; heteroaromatics; phosphonates; phthalamic acids; benzotriazines; benzenesulfonamides; pyridazinones; carboxylic acid amides; tetracycline antibiotic; thiocarbamate; benzothiadiazole BTH; benzisothiazole; thiadiazolecarboxamide; thiazolecarboxamides; benzamidoxime; quinazolinone; benzophenone; acylpicolide; inorganic compounds, such as copper salts and sulphur; dithiocarbamates and relatives; phthalimides; chloronitriles; sulphamides; guanidines; triazines; quinones.

Other fungicides that may optionally be admixed with the isoxazoline compounds of the invention may also be from the classes of compounds described in U.S. Pat. Nos. 7,001,903 and 7,420,062, each incorporated herein by reference.

Herbicides that are known from the literature and classified by HRAC (Herbicide Resistance Action Committee) and may be combined with the compounds of the invention are, for example: aryloxyphenoxy-propionate; cyclohexanedione; phenylpyrazoline; sulfonylurea; imidazolinone, such as imazapic and imazethapyr; triazolopyrimidine; pyrimidinyl(thio)benzoate; sulfonylaminocarbonyl-triazolinone; triazine, such as atrazine; triazinone; triazolinone; uracil; pyridazinone; phenyl-carbamate; urea; amide; nitrile; benzothiadiazinone; phenyl-pyridazine; bipyridylium, such as paraquat; diphenylether; phenylpyrazole; N-phenylphthalimide; thiadiazole; thiadiazole; triazolinone; oxazolidinedione; pyrimidindione; pyridazinone; pyridinecarboxamide; triketone; isoxazole; pyrazole; triazole; isoxazolidinone; urea, such as linuron; diphenylether; glycine, such as glyphosate; phosphinic acid, such as glufosinate-ammonium; carbamate; dinitroaniline, such as pendimethalin; phosphoroamidate; pyridine; benzamide; benzoic acid; chloroacetamide; metolachlor; acetamide; oxyacetamide; tetrazolinone; nitrile; benzamide; triazolocarboxamide; quinoline carboxylic acid; dinitrophenol; thiocarbamate; phosphorodithioate; benzofuran; chloro-carbonic-acid; phenoxy-carboxylic-acid, such as 2,4-D; benzoic acid, such as dicamba; pyridine carboxylic acid, such as clopyralid, triclopyr, fluroxypyr and picloram; quinoline carboxylic acid; phthalamate semicarbazone; qrylaminopropionic acid; qrylaminopropionic acid; organoarsenical.

Other herbicides that may optionally be admixed are compounds described in U.S. Pat. Nos. 7,432,226, 7,012,041, and 7,365,082, all incorporated herein by reference.

Appropriate herbicide safeners include but are not limited to benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anyhydride and oxabetrinil.

Bactericides include, but are not limited to, bronopol, dichlorophen, nitrapyrin, nickel dimethyldithiocarbamate, kasugamycin, octhilinone, furancarboxylic acid, oxytetracycline, probenazole, streptomycin, tecloftalam, copper sulfate and other copper preparations.

Insecticides/acaricides/nematicides include those compounds mentioned in U.S. Pat. Nos. 7,420,062 and 7,001,903, U.S. Patent publication 2008/0234331, each incorporated herein by reference, and the compounds classified by IRAC (Insecticide Resistance Action Committee). Examples of insecticides/acaricides/nematicides include, but are limited to, carbamates; triazemate; organophosphates; cyclodiene organochlorines; phenylpyrazoles; DDT; methoxychlor; pyrethroids; pyrethrins; neonicotinoids; nicotine; bensultap; cartap hydrochloride; nereistoxin analogues; spinosyns; avermectins and milbemycins; juvenile hormone analogues; fenoxycarb; fenoxycarb; alkyl halides; chloropicrin; sulfuryl fluoride; cryolite; pymetrozine; flonicamid; clofentezine; hexythiazox; etoxazole; *Bacillus sphaericus*; diafenthiuron; organotin miticides; propargite; tetradifon; chlorfenapyr; DNOC; benzoylureas; buprofezin; cyromazine; diacylhydrazines; azadirachtin; amitraz; hydramethylnon; acequinocyl; fluacrypyrim; METI acaricides; rotenone; indoxacarb; metaflumizone; tetronic acid derivatives; aluminium phosphide; cyanide; phosphine; bifenazate; fluoroacetate; P450-dependent monooxygenase inhibitors; esterase inhibitors; diamides; benzoximate; chinomethionat; dicofol; pyridalyl; borax; tartar emetic; fumigants, such as methyl bromide; ditera; clandosan; sincocin.

Veterinary compositions may include one or more isoxazoline compounds of the invention in combination with additional pharmaceutically or veterinarily active agents. In some embodiments, the additional active agent(s) may be one or more acaricide, anthelmintic, endectocide and insecticide active agent. Anti-parasitic agents can include both ectoparasiticisal and endoparasiticidal agents.

Veterinary pharmaceutical agents that may be included in the compositions of the invention are well-known in the art (see e.g. *Plumb' Veterinary Drug Handbook*, 5$^{th}$ Edition, ed. Donald C. Plumb, Blackwell Publishing, (2005) or *The Merck Veterinary Manual*, 9$^{th}$ Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitriptyline, amlodipine besylate, ammonium chloride, ammonium molybdenate, amoxicillin, clavulanate potassium, amphotericin B desoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, aumrnofin, aurothioglucose, azaperone, azathioprine, azithromycin, baclofen, barbituates, benazepril, betamethasone, bethanechol chloride, bisacodyl, bismuth subsalicylate, bleomycin sulfate, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, camitine, carprofen, carvedilol, cefadroxil, cefazolin sodium, cefixime, clorsulon, cefoperazone sodium, cefotaxime sodium, cefotetan disodium, cefoxitin sodium, cefpodoxime proxetil, ceftazidime, ceftiofur sodium, ceftiofur, ceftiaxone sodium, cephalexin, cephalosporins, cephapirin, charcoal (activated), chlorambucil, chloramphenicol, chlordiazepoxide, chlordiazepoxide+/–clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, clonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, diclofenac sodium, dicloxacillin, diethylcarbamazine citrate, diethylstilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium.calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (OXYGLOBIN®®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inamrinone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxibutynin chloride, oxymorphone, oxytretracycline, oxytocin, pamidronate disodium, pancreplipase, pancuronium bromide, paromomycin sulfate, parozetine, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenytoin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, prazosin, prednisolone/prednisone, primidone, procainamide, procarbazine, prochlorperazine, propantheline bromide, *Propionibacterium acnes* injection, propofol, propranolol, protamine sulfate, pseudoephedrine, psyllium hydrophilic mucilloid, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/1-deprenyl, sertraline, sevelamer, sevoflurane, silymarin/milk thistle, sodium bicarbonate, sodium polystyrene sulfonate, sodium stibogluconate, sodium sulfate, sodum thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocainide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In one embodiment of the invention, arylpyrazole compounds, such as phenylpyrazoles, known in the art may be combined with the isoxazoline compounds of the invention. Examples of such arylpyrazole compounds include but are not limited to those described in U.S. Pat. Nos. 6,001,384; 6,010,710; 6,083,519; 6,096,329; 6,174,540; 6,685,954 and 6,998,131 (all of which are incorporated herein by reference, each assigned to Merial, Ltd., Duluth, Ga.). A particularly preferred arylpyrazole compound is fipronil.

In another embodiment of the invention, one or more macrocyclic lactones, which act as an acaricide, anthelmintic agent and/or insecticide, can be combined with the isoxazoline compounds of the invention. The macrocyclic lactones include, but are not limited to, avermectins such as abamectin, dimadectin, doramectin, emamectin, eprinomectin, ivermectin, latidectin, lepimectin, selamectin and ML-1, 694,554, and milbemycins such as milbemectin, milbemycin D, milbemycin oxime, moxidectin and nemadectin. Also included are the 5-oxo and 5-oxime derivatives of said avermectins and milbemycins.

The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schonberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054.

Macrocyclic lactones are either natural products or are semi-synthetic derivatives thereof. The structure of the avermectins and milbemycins are closely related, e.g., by sharing a complex 16-membered macrocyclic lactone ring. The natural product avermectins are disclosed in U.S. Pat. No. 4,310,519 and the 22,23-dihydro avermectin compounds are disclosed in U.S. Pat. No. 4,199,569 (both incorporated herein by reference). Mention is also made of U.S. Pat. Nos. 4,468,390, 5,824,653, EP 0 007 812 A1, U.K. Patent Specification 1 390 336, EP 0 002 916, and New Zealand Patent No. 237 086 (all incorporated by reference), inter alia. Naturally occurring milbemycins are described in U.S. Pat. No. 3,950,360, which is incorporated herein by reference, as well as in the various references cited in "The Merck Index" 12$^{th}$ ed., S. Budavari, Ed., Merck & Co., Inc. Whitehouse Station, N.J. (1996). Latidectin is described in the "International Nonproprietary Names for Pharmaceutical Substances (INN)", WHO Drug Information, vol. 17, no. 4, pp. 263-286, (2003). Semisynthetic derivatives of these classes of compounds are well known in the art and are described, for example, in U.S. Pat. Nos. 5,077,308, 4,859,657, 4,963,582, 4,855,317, 4,871,719, 4,874,749, 4,427,663, 4,310,519, 4,199,569, 5,055,596, 4,973,711, 4,978,677, 4,920,148 and EP 0 667 054 (all incorporated by reference).

In another embodiment, the isoxazoline compounds of the invention may be combined with a class of compounds known as insect growth regulators (IGRs). Compounds belonging to this group are well known to the practitioner and represent a wide range of different chemical classes. These compounds all act by interfering with the development or growth of the insect pests. Insect growth regulators are described, for example, in U.S. Pat. Nos. 3,748,356, 3,818,047, 4,225,598, 4,798,837, 4,751,225, EP 0 179 022 or U.K. 2 140 010 as well as U.S. Pat. Nos. 6,096,329 and 6,685,954 (all incorporated herein by reference).

In one embodiment the IGR is a compound that mimics juvenile hormone. Examples of juvenile hormone mimics include azadirachtin, diofenolan, fenoxycarb, hydroprene, kinoprene, methoprene, pyriproxyfen, tetrahydroazadirachtin and 4-chloro-2(2-chloro-2-methyl-propyl)-5-(6-iodo-3-pyridylmethoxy)pyridazine-3(2H)-one.

In another embodiment, the IGR compound is a chitin synthesis inhibitor. Chitin synthesis inhibitors include chlorfluazuron, cyromazine, diflubenzuron, fluazuron, flucycloxuron, flufenoxuron, hexaflumuron, lufenuron, tebufenozide, teflubenzuron, triflumoron, novaluron, 1-(2,6-difluorobenzoyl)-3-(2-fluoro-4-(trifluoromethyl)phenylurea, 1-(2,6-difluoro-benzoyl)-3-(2-fluoro-4-(1,1,2,2-tetrafluoroethoxy)-phenylurea and 1-(2,6-difluorobenzoyl)-3-(2-fluoro-4-trifluoromethyl)phenylurea.

In yet another embodiment of the invention, adulticide insecticides and acaricides can also be combined with the isoxazoline compounds of the invention. These include pyrethrins (which include cinerin I, cinerin II, jasmolin I, jasmolin II, pyrethrin I, pyrethrin II and mixtures thereof) and pyrethroids (including permethrin cyhalothrin, cypermethrin, deltamethrin, fenvalerate, flucythrinate), and carbamates including, but are not limited to, benomyl, carbanolate, carbaryl, carbofuran, meththiocarb, metolcarb, promacyl, propoxur, aldicarb, butocarboxim, oxamyl, thiocarboxime and thiofanox.

In some embodiments, the isoxazoline compounds of the invention may be combined with one or more antinematodal agents including, but not limited to, active agents in the benzimidazoles, imidazothiazoles, tetrahydropyrimidines, and organophosphate class of compounds. In some embodiments, benzimidazoles including, but not limited to, thiabendazole, cambendazole, parbendazole, oxibendazole, mebendazole, flubendazole, fenbendazole, oxfendazole, albendazole, cyclobendazole, febantel, thiophanate and its o,o-dimethyl analogue may be included in the compositions.

In other embodiments, the isoxazoline compounds of the invention may be combined with an imidazothiazole compounds including, but not limited to, tetramisole, levamisole and butamisole. In still other embodiments, the isoxazoline compounds of the invention may be combined with tetrahydropyrimidine active agents including, but not limited to, pyrantel, oxantel, and morantel. Suitable organophosphate active agents include, but are not limited to, coumaphos, trichlorfon, haloxon, naftalofos and dichlorvos, heptenophos, mevinphos, monocrotophos, TEPP, and tetrachlorvinphos.

In other embodiments, the isoxazoline compounds of the invention may be combined with the antinematodal compounds phenothiazine and piperazine as the neutral compound, or in various salt forms, diethylcarbamazine, phenols such as disophenol, arsenicals such as arsenamide, ethanolamines such as bephenium, thenium closylate, and methyridine; cyanine dyes including pyrvinium chloride, pyrvinium pamoate and dithiazanine iodide; isothiocyanates including bitoscanate, suramin sodium, phthalofyne, and various natural products including, but not limited to, hygromycin B, α-santonin and kainic acid.

In other embodiments, the isoxazoline compounds of the invention may be combined with antitrematodal agents. Suitable antitrematodal agents include, but are not limited to, the miracils such as miracil D and mirasan; praziquantel, clonazepam and its 3-methyl derivative, oltipraz, lucanthone, hycanthone, oxamniquine, amoscanate, niridazole, nitroxynil, various bisphenol compounds known in the art including hexachlorophene, bithionol, bithionol sulfoxide and menichlopholan; various salicylanilide compounds including tribromsalan, oxyclozanide, clioxanide, rafoxanide, brotianide, bromoxanide and closantel; triclabendazole, diamfenetide, clorsulon, hetolin and emetine.

Anticestodal compounds may also be advantageously combined with isoxazoline compounds of the invention including, but not limited to, arecoline in various salt forms, bunamidine, niclosamide, nitroscanate, paromomycin and paromomycin II.

In yet other embodiments, the isoxazoline compounds of the invention may be combined with other active agents that are effective against arthropod parasites. Suitable active agents include, but are not limited to, bromocyclen, chlordane, DDT, endosulfan, lindane, methoxychlor, toxaphene, bromophos, bromophos-ethyl, carbophenothion, chlorfenvinphos, chlorpyrifos, crotoxyphos, cythioate, diazinon, dichlorenthion, diemthoate, dioxathion, ethion, famphur, fenitrothion, fenthion, fospirate, iodofenphos, malathion, naled, phosalone, phosmet, phoxim, propetamphos, ronnel, stirofos, allethrin, cyhalothrin, cypermethrin, deltamethrin, fenvalerate, flucythrinate, permethrin, phenothrin, pyrethrins, resmethrin, benzyl benzoate, carbon disulfide, crotamiton, diflubenzuron, diphenylamine, disulfiram, isobornyl thiocyanato acetate, methoprene, monosulfiram, pirenonylbutoxide, rotenone, triphenyltin acetate, triphenyltin hydroxide, deet, dimethyl phthalate, and the compounds 1,5a,6,9,9a,9b-hexahydro-4a(4H)-dibenzofurancarboxaldehyde (MGK-11), 2-(2-ethylhexyl)-3a,4,7,7a-tetrahydro-4,7-methano-1H-isoindole-1,3(2H)dione (MGK-264), dipropyl-2,5-pyridinedicarboxylate (MGK-326) and 2-(octylthio) ethanol (MGK-874).

In another embodiment, the isoxazoline compounds of the invention be combined with pyrethroid active agents including, but not limited to, permethrin, deltamethrin, cypermethrin, cyphenothrin, etofenprox, fenvalerate and cyfluthrin.

Another antiparasitic agent that can be combined with the isoxazoline compounds of the invention include a biologically active peptide or protein including, but not limited to, depsipeptides, which act at the neuromuscular junction by stimulating presynaptic receptors belonging to the secretin receptor family resulting in the paralysis and death of parasites. In one embodiment, the depsipeptide is emodepside (see Willson et al., Parasitology, January 2003, 126(Pt 1):79-86).

In another embodiment, the isoxazoline compounds of the invention may be combined with an active agent from the neonicotinoid class of pesticides. The neonicotinoids bind and inhibit insect specific nicotinic acetylcholine receptors. In one embodiment, the neonicotinoid insecticidal agent is imidacloprid. Imidacloprid is a well-known neonicotinoid active agent and is the key active ingredient in the topical parasiticide products Advantage®, Advantage® II, K9 Advantix®, and K9 Advantix® II sold by Bayer Animal Health. Agents of this class are described, for example, in U.S. Pat. No. 4,742,060 or in EP 0 892 060 (incorporated herein by reference).

In another embodiment, the neonicotinoid active agent is nitenpyram. Nitenpyram is the active ingredient in the oral product CAPSTAR™ Tablets sold by Novartis Animal Health. Nitenpyram is active against adult fleas when given daily as an oral tablet. Nitenpyram works by interfering with normal nerve transmission and leads to the death of the insect. Nitenpyram has a very fast onset of action against fleas. For example, CAPSTAR™ Tablets begin to act against fleas in as early as 30 minutes after administration and is indicated for use as often as once a day.

In certain embodiments, an insecticidal agent that can be combined with the isoxazoline compounds of the invention is a semicarbazone, such as metaflumizone.

In another embodiment, the isoxazoline compounds of the invention may advantageously be combined with another isoxazoline compounds known in the art. These active agents are described in U.S. Pat. Nos. 7,964,204, 8,410,153, US 2011/0152312, US 2010/0254960 A1, US2011/0159107, US2012/0309620, US2012/0030841, US2010/0069247, WO 2007/125984, WO 2012/086462, U.S. Pat. No. 8,318,757, US 2011/0144349, U.S. Pat. No. 8,053,452; US 2010/0137612, US 2010/0254959, US 2011/152081, WO 2012/089623, WO 2012/089622, U.S. Pat. Nos. 8,119,671; 7,947,715; WO 2102/120135, WO 2012/107533, WO 2011/157748, US 2011/0245274, US 2011/0245239, US 2012/0232026, US 2012/0077765, US 2012/0035122, US 2011/0251247, WO 2011/154433, WO 2011/154434, US 2012/0238517, US 2011/0166193, WO 2011/104088, WO 2011/104087, WO 2011/104089, US 2012/015946, US 2009/0143410, WO 2007/123855 A2, US 2011/0118212, U.S. Pat. No. 7,951,828 & U.S. Pat. No. 7,662,972, US 2010/0137372 A1, US 2010/0179194 A2, US 2011/0086886 A2, US 2011/0059988 A1, US 2010/0179195 A1, U.S. Pat. Nos. 7,897,630, 7,951,828 and 7,662,972, all of which are incorporated herein by reference in their entirety.

In another embodiment of the invention, nodulisporic acid and its derivatives (a class of known acaricidal, anthelmintic, anti-parasitic and insecticidal agents) may be combined with the isoxazoline compounds of the invention. These compounds are used to treat or prevent infections in humans and animals and are described, for example, in U.S. Pat. Nos. 5,399,582, 5,962,499, 6,221,894 and 6,399,786, all of which are hereby incorporated by reference in their entirety.

In another embodiment, anthelmintic compounds of the amino acetonitrile class (AAD) of compounds such as monepantel (ZOLVIX), and the like, may be combined with the isoxazoline compounds of the invention. These compounds are described, for example, in WO 2004/024704 and U.S. Pat. No. 7,084,280 (incorporated by reference); Sager et al., Veterinary Parasitology, 2009, 159, 49-54; Kaminsky et al., Nature vol. 452, 13 Mar. 2008, 176-181.

The isoxazoline compounds of the invention may also be combined with aryloazol-2-yl cyanoethylamino compounds such as those described in U.S. Pat. No. 8,088,801 to Soll et al., which is incorporated herein by reference, and thioamide derivatives of these compounds, as described in U.S. Pat. No. 7,964,621, also incorporated herein by reference.

The isoxazoline compounds of the invention may also be combined with paraherquamide compounds and derivatives of these compounds, including derquantel (see Ostlind et al., *Research in Veterinary Science*, 1990, 48, 260-61; and Ostlind et al., *Medical and Veterinary Entomology*, 1997, 11, 407-408). The paraherquamide family of compounds is a known class of compounds that include a spirodioxepino indole core with activity against certain parasites (see *Tet. Lett.* 1981, 22, 135; *J. Antibiotics* 1990, 43, 1380, and *J Antibiotics* 1991, 44, 492). In addition, the structurally related marcfortine family of compounds, such as marcfortines A-C, are also known and may be combined with the formulations of the invention (see *J. Chem. Soc.—Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004432, U.S. Pat. Nos. 5,703,078 and 5,750,695, all of which are hereby incorporated by reference in their entirety.

In general, the additional active agent is included in the composition in an amount of between about 0.1 µg and about 1000 mg. More typically, the additional active agent may be included in an amount of about 10 µg to about 500 mg, about 1 mg to about 300 mg, about 10 mg to about 200 mg or about 10 mg to about 100 mg.

In other embodiments of the invention, the additional active agent may be included in the composition to deliver a dose of about 5 µg/kg to about 50 mg/kg per weight of the animal. In other embodiments, the additional active agent may be present in an amount sufficient to deliver a dose of about 0.01 mg/kg to about 30 mg/kg, about 0.1 mg/kg to about 20 mg/kg, or about 0.1 mg/kg to about 10 mg/kg of weight of animal. In other embodiments, the additional active agent may be present in a dose of about 5 µg/kg to about 200 µg/kg or about 0.1 mg/kg to about 1 mg/kg of weight of animal. In still another embodiment of the invention, the additional active agent is included in a dose between about 0.5 mg/kg to about 50 mg/kg.

EXAMPLES

List of Abbreviations

ACN acetonitrile
DCM dichloromethane
DIEA diisopropylethylamine
DMF N,N-dimethylformamide
DMSO dimethylsulfoxide
EtOH ethanol
EtOAc or EA ethyl acetate
HATU 1-[bis(dimethylamino)methylene]-1H-1,2,3-triazolo [4,5 b]pyridinium 3-oxide hexafluorophosphate
m-CPBA meta-chloroperoxybenzoic acid
NaOAc sodium acetate
PE petroleum ether TBAF tert-butyl ammonium fluoride
TEA triethylamine
THF tetrahydrofuran
TMSCN trimethylsilyl cyanide

PREPARATION EXAMPLES

The compounds of the invention #1-6 shown in Table 59 above were prepared according to Preparation Examples 1-6 below.

Preparation Example 1: Compound 1

Compound 1 shown in Table 59 was prepared according Schemes 5 to 7 shown below.

Scheme 5

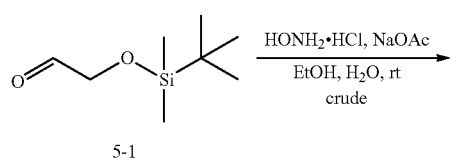

HONH$_2$·HCl, NaOAc
EtOH, H$_2$O, rt
crude

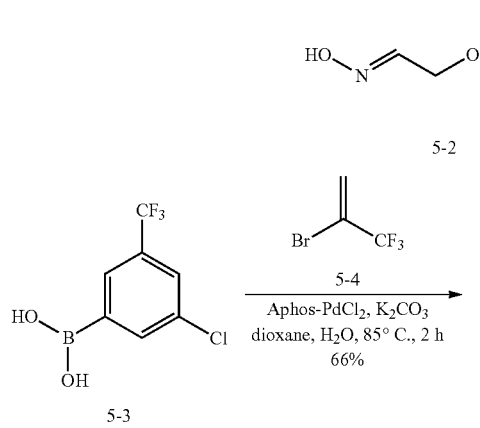

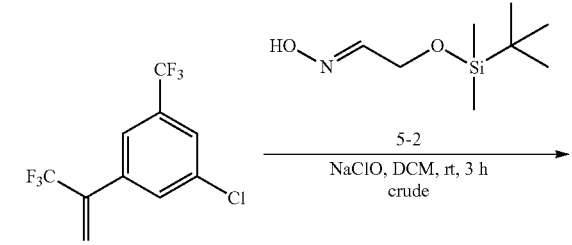

5-2
NaClO, DCM, rt, 3 h
crude

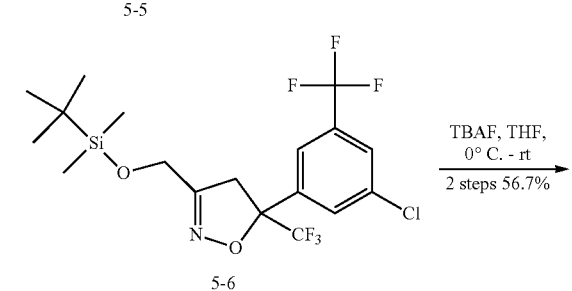

TBAF, THF,
0° C. - rt
2 steps 56.7%

-continued

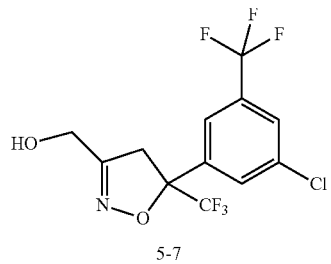

5-7

Scheme 6

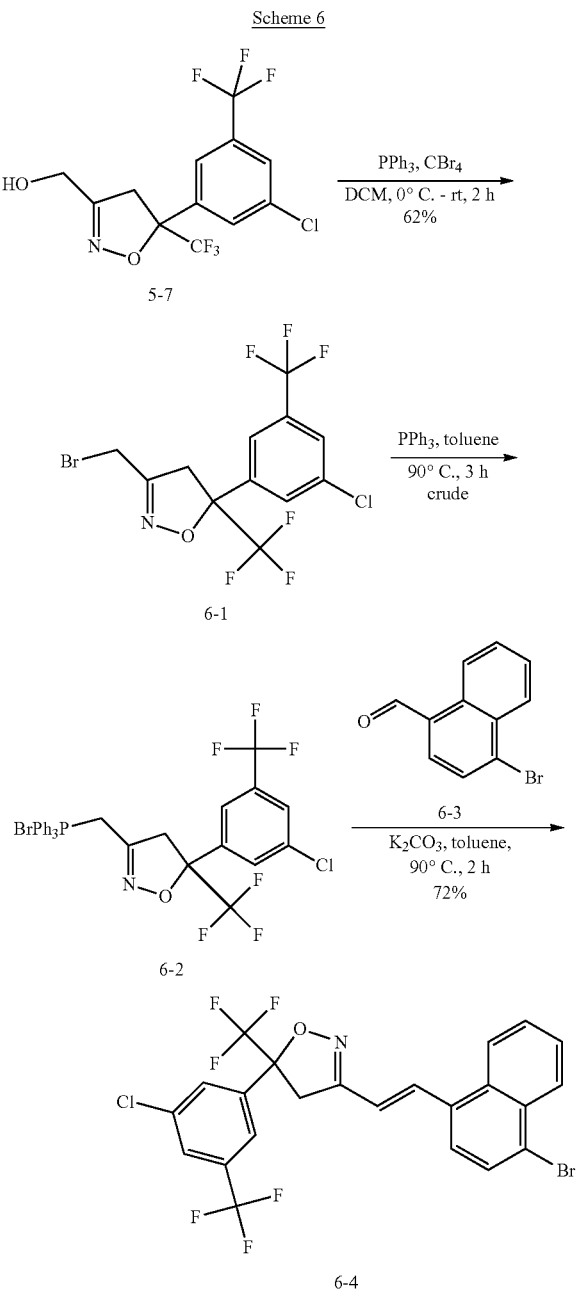

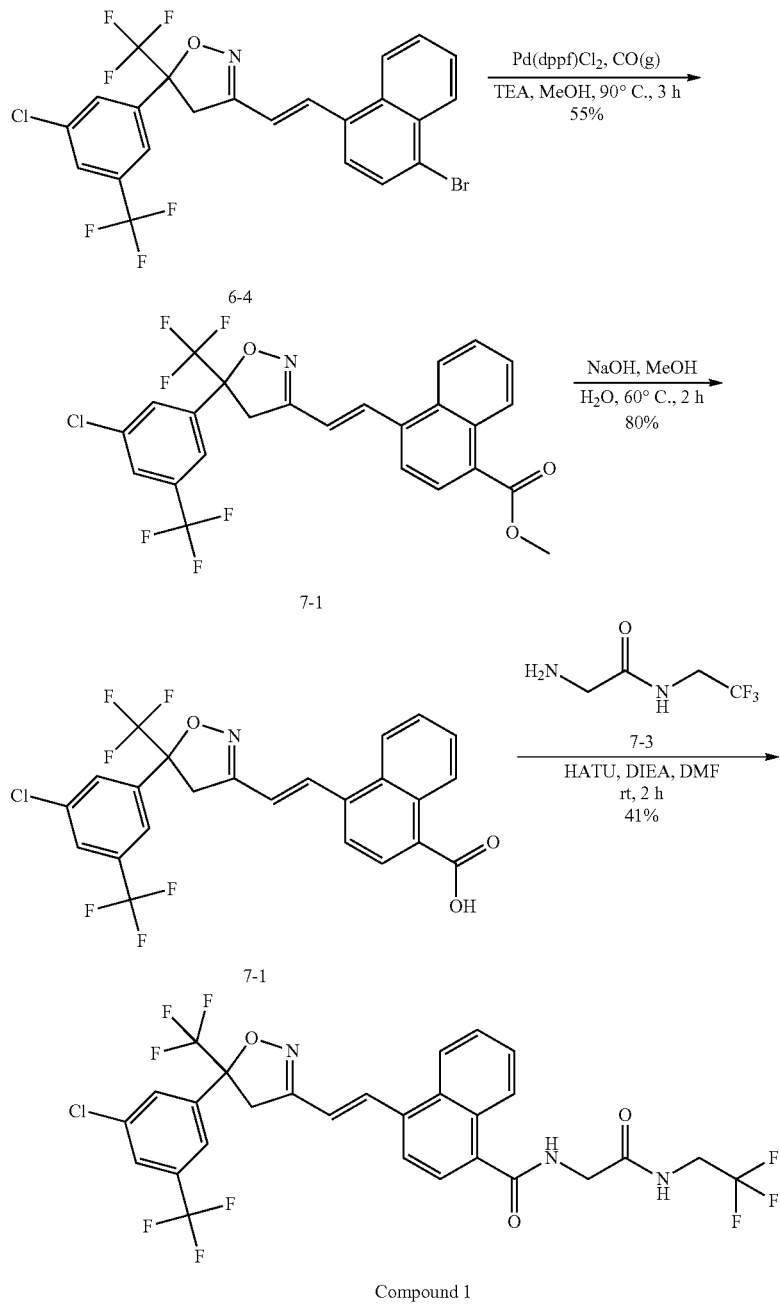

Compound 1

N-[2-[(tert-butyldimethylsilyl)oxy]ethylidene]hydroxylamine (5-2)

Into a 1-L round-bottom flask purged and maintained with an inert atmosphere of nitrogen, was placed a solution of $NH_2OH \cdot HCl$ (30 g) in water (500 mL), NaOAc (70 g). This was followed by the addition of a solution of 2-[(tert-butyldimethylsilyl)oxy]acetaldehyde (5-1, 50 g, 286.84 mmol, 1.00 equiv) in EtOH (100 mL) dropwise with stirring. The resulting solution was stirred overnight at room temperature. The resulting solution was extracted with 3×200 mL of dichloromethane and the organic layers combined. The organic phase was washed with 3×100 mL of brine. The organic layer was collected and dried over anhydrous sodium sulfate. The solids were filtered out. The filtrate was concentrated under vacuum. This resulted in 52 g (crude) of N-[2-[(tert-butyldimethylsilyl)oxy]ethylidene]hydroxylamine, 5-2, as yellow oil.

1-chloro-3-(trifluoromethyl)-5-(3,3,3-trifluoroprop-1-en-2-yl)benzene (5-5)

Into a 1000-mL round-bottom flask purged and maintained with an inert atmosphere of nitrogen, was placed a solution of 2-bromo-3,3,3-trifluoroprop-1-ene (5-4, 58 g, 331.53 mmol, 3 equiv) in dioxane (450 mL), A-Phos-PdCl$_2$ (2.4 g), a solution of potassium carbonate (76 g, 549.89 mmol, 5 equiv) in water (100 mL). This was followed by the addition of a solution of [3-chloro-5-(trifluoromethyl)phenyl]boronic acid (5-3, 25 g, 111.42 mmol, 1.00 equiv) in dioxane (50 mL) dropwise with stirring at 85° C. The resulting mixture was stirred for 2 h at 85° C. The resulting mixture was diluted with 1 L of ethyl acetate (EA) and then was washed with 3×300 mL of $H_2O$. The organic layer was collected and dried over anhydrous sodium sulfate. The solids were filtered out and the filtrate was concentrated under vacuum. The residue was applied onto a silica gel column with petroleum ether. This resulted in 20 g (66%) of 1-chloro-3-(trifluoromethyl)-5-(3,3,3-trifluoroprop-1-en-2-yl)benzene (5-5) as yellow oil.

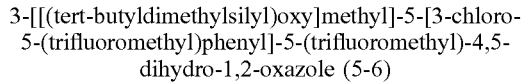

3-[[(tert-butyldimethylsilyl)oxy]methyl]-5-[3-chloro-5-(trifluoromethyl)phenyl]-5-(trifluoromethyl)-4,5-dihydro-1,2-oxazole (5-6)

Into a 2-L round-bottom flask purged and maintained with an inert atmosphere of nitrogen, was placed a solution of 1-chloro-3-(trifluoromethyl)-5-(3,3,3-trifluoroprop-1-en-2-yl)benzene (5-5, 30 g, 109.25 mmol, 1.00 equiv) in dichloromethane (400 mL) and NaClO (13% aq., 750 mL). This was followed by the addition of a solution of N-[2-(tert-butyldimethylsilyl)ethylidene]hydroxylamine (5-2, 40 g, 230.78 mmol, 2.11 equiv) in dichloromethane (100 mL) dropwise with stirring. The resulting solution was stirred for 3 h at room temperature. The resulting solution was extracted with dichloromethane and the organic layers combined and dried over anhydrous sodium sulfate. The solids were filtered out and the filtrate was concentrated under vacuum. This resulted in 45 g (crude) of 3-[[(tert-butyldimethylsilyl)oxy]methyl]-5-[3-chloro-5-(trifluoromethyl)phenyl]-5-(trifluoromethyl)-4,5-dihydro-1,2-oxazole (5-6) as brown oil.

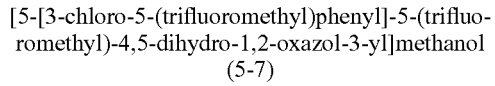

[5-[3-chloro-5-(trifluoromethyl)phenyl]-5-(trifluoromethyl)-4,5-dihydro-1,2-oxazol-3-yl]methanol (5-7)

Into a 500-mL round-bottom flask, was placed a solution of 3-[[(tert-butyldimethylsilyl)oxy]methyl]-5-[3-chloro-5-(trifluoromethyl)phenyl]-5-(trifluoromethyl)-4,5-dihydro-1,2-oxazole (5-6, 20 g, 43.30 mmol, 1.00 equiv) in tetrahydrofuran (200 mL). To this solution was added TBAF (22.7 g, 86.82 mmol, 2.01 equiv) in portions at 0° C. The resulting solution was stirred for 2 h at room temperature, and then concentrated under vacuum. The crude product was purified by Flash-Prep-HPLC with the following conditions (IntelFlash-1): Column, C18 silica gel; mobile phase, $H_2O$ and $CH_3CN$ (20% $CH_3CN$ increasing to 60% within 15 min); Detector, UV 220 nm. This resulted in 11 g (73%) of [5-[3-chloro-5-(trifluoromethyl)phenyl]-5-(trifluoromethyl)-4,5-dihydro-1,2-oxazol-3-yl]methanol (5-7) as brown oil.

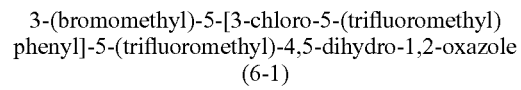

3-(bromomethyl)-5-[3-chloro-5-(trifluoromethyl)phenyl]-5-(trifluoromethyl)-4,5-dihydro-1,2-oxazole (6-1)

Into a 500-mL round-bottom flask purged and maintained with an inert atmosphere of nitrogen, was placed a solution of [5-[3-chloro-5-(trifluoromethyl)phenyl]-5-(trifluoromethyl)-4,5-dihydro-1,2-oxazol-3-yl]methanol (5-7, 17.2 g, 49.48 mmol, 1.00 equiv) in dichloromethane (150 mL) and $PPh_3$ (19.5 g, 74.35 mmol, 1.50 equiv). This was followed by the addition of a solution of $CBr_4$ (19.5 g) in dichloromethane (50 mL) dropwise with stirring at 0° C. The resulting solution was stirred overnight at room temperature. The resulting mixture was concentrated under vacuum, and the residue was applied onto a silica gel column with ethyl acetate/petroleum ether (1/20). This resulted in 12.56 g (62%) of 3-(bromomethyl)-5-[3-chloro-5-(trifluoromethyl) phenyl]-5-(trifluoromethyl)-4,5-dihydro-1,2-oxazole (6-1) as brown oil.

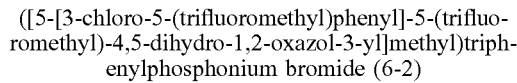

([5-[3-chloro-5-(trifluoromethyl)phenyl]-5-(trifluoromethyl)-4,5-dihydro-1,2-oxazol-3-yl]methyl)triphenylphosphonium bromide (6-2)

Into a 500-mL round-bottom flask purged and maintained with an inert atmosphere of nitrogen, was placed a solution of 3-(bromomethyl)-5-[3-chloro-5-(trifluoromethyl)phenyl]-5-(trifluoromethyl)-4,5-dihydro-1,2-oxazole (6-1, 12 g, 29.23 mmol, 1.00 equiv) in toluene (120 mL) and $PPh_3$ (7.67 g, 29.24 mmol, 1.00 equiv). The resulting solution was stirred for 3 h at 90° C. The resulting mixture was concentrated under vacuum. This resulted in 19.9 g (crude) of ([5-[3-chloro-5-(trifluoromethyl)phenyl]-5-(trifluoromethyl)-4,5-dihydro-1,2-oxazol-3-yl]methyl)triphenylphosphonium bromide (6-2) as a brown solid.

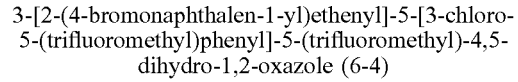

3-[2-(4-bromonaphthalen-1-yl)ethenyl]-5-[3-chloro-5-(trifluoromethyl)phenyl]-5-(trifluoromethyl)-4,5-dihydro-1,2-oxazole (6-4)

Into a 50-mL round-bottom flask, was placed toluene (15 mL), 4-bromonaphthalene-1-carbaldehyde (6-3, 800 mg, 3.40 mmol, 1.21 equiv), 5-[3-chloro-5-(trifluoromethyl)phenyl]-5-(trifluoromethyl)-3-[(triphenyl-[5]-phosphanyl) methyl]-4,5-dihydro-1,2-oxazole bromide (6-2, 1.9 g, 2.82 mmol, 1.00 equiv) and potassium carbonate (1.2 g, 8.68 mmol, 3.08 equiv). The resulting solution was stirred 2 h at 90° C. and then the reaction mixture was cooled to room temperature. The resulting mixture was concentrated under vacuum. The residue was applied onto a silica gel column with ethyl acetate/petroleum ether (1:5). This resulted in 1.12 g (72%) of 3-[2-(4-bromonaphthalen-1-yl)ethenyl]-5-[3-chloro-5-(trifluoromethyl)phenyl]-5-(trifluoromethyl)-4,5-dihydro-1,2-oxazole (6-4) as a yellow solid.

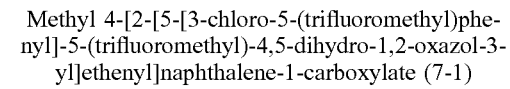

Methyl 4-[2-[5-[3-chloro-5-(trifluoromethyl)phenyl]-5-(trifluoromethyl)-4,5-dihydro-1,2-oxazol-3-yl]ethenyl]naphthalene-1-carboxylate (7-1)

Into a 50-mL pressure tank reactor (20 atm), was placed methanol (15 mL), 3-[(E)-2-(4-bromonaphthalen-1-yl)ethenyl]-5-[3-chloro-5-(trifluoromethyl)phenyl]-5-(trifluoromethyl)-4,5-dihydro-1,2-oxazole (6-4, 300 mg, 0.55 mmol, 1.00 equiv), Pd(dppf)Cl₂ (100 mg, 0.14 mmol, 0.25 equiv), TEA (160 mg, 1.58 mmol, 2.89 equiv). To the solution was introduced CO (g). The resulting solution was stirred for 3 h at 90° C. and then concentrated under vacuum. The residue was applied onto a silica gel column with ethyl acetate/petroleum ether (1:5). This resulted in 160 mg (55%) of methyl 4-[2-[5-[3-chloro-5-(trifluoromethyl)phenyl]-5-(trifluoromethyl)-4,5-dihydro-1,2-oxazol-3-yl]ethenyl]naphthalene-1-carboxylate (7-1) as yellow oil.

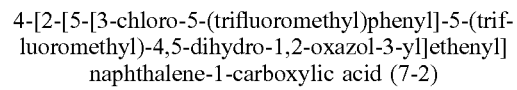

4-[2-[5-[3-chloro-5-(trifluoromethyl)phenyl]-5-(trifluoromethyl)-4,5-dihydro-1,2-oxazol-3-yl]ethenyl] naphthalene-1-carboxylic acid (7-2)

Into a 50-mL round-bottom flask, was placed methanol (10 mL), methyl 4-[2-[5-[3-chloro-5-(trifluoromethyl)phenyl]-5-(trifluoromethyl)-4,5-dihydro-1,2-oxazol-3-yl]ethenyl]naphthalene-1-carboxylate (7-1, 180 mg, 0.34 mmol, 1.00 equiv) and sodium hydroxide (60 mg, 1.50 mmol, 4.40 equiv) in water (3 mL). The resulting solution was stirred for 2 h at 60° C. The pH value of the solution was adjusted to 4 with hydrogen chloride (2 mol/L). The resulting solution was extracted with 3×10 mL of ethyl acetate. The combined organic layers were dried over anhydrous sodium sulfate and concentrated under vacuum.

This resulted in 140 mg (80%) of 4-[2-[5-[3-chloro-5-(trifluoromethyl)phenyl]-5-(trifluoromethyl)-4,5-dihydro-1,2-oxazol-3-yl]ethenyl]naphthalene-1-carboxylic acid (7-2) as a yellow solid.

2-([4-[2-[5-[3-chloro-5-(trifluoromethyl)phenyl]-5-(trifluoromethyl)-4,5-dihydro-1,2-oxazol-3-yl]ethenyl]naphthalen-1-yl]formamido)-N-(2,2,2-trifluoroethyl)acetamide (Compound 1)

Into a 50-mL round-bottom flask, was placed N,N-dimethylformamide (4 mL), 4-[2-[5-[3-chloro-5-(trifluoromethyl)phenyl]-5-(trifluoromethyl)-4,5-dihydro-1,2-oxazol-3-yl]ethenyl]naphthalene-1-carboxylic acid (7-2, 60 mg, 0.12 mmol, 1.00 equiv), 2-amino-N-(2,2,2-trifluoroethyl)acetamide hydrochloride (7-3, 30 mg, 0.19 mmol, 1.65 equiv), HATU (80 mg, 0.21 mmol, 1.80 equiv) and DIEA (50 mg, 0.39 mmol, 3.31 equiv). The resulting solution was stirred for 2 h at room temperature. The crude product was purified by Flash-Prep-HPLC with the following conditions (IntelFlash-1): Column, C18 silica gel; mobile phase, H$_2$O and CH$_3$CN (20% CH$_3$CN increasing to 80% within 25 min); Detector, UV 254 nm. This resulted in 31.3 mg (41%) of 2-([4-[2-[5-[3-chloro-5-(trifluoromethyl)phenyl]-5-(trifluoromethyl)-4,5-dihydro-1,2-oxazol-3-yl]ethenyl]naphthalen-1-yl]formamido)-N-(2,2,2-trifluoroethyl)acetamide (Compound 1) as a white solid. (ES, m/z): 652 [M+H]+; $^1$H-NMR (300 MHz, CDCl$_3$, ppm) δ 8.38-8.35 (m, 1H), 8.15-8.12 (m, 1H), 7.86 (s, 1H), 7.81 (s, 1H), 7.80-7.55 (m, 6H), 7.15 (d, J=15.9 Hz, 1H), 6.79 (br, 1H), 6.66 (br, 1H), 4.35-4.30 (m, 2H), 4.15 (d, J=16.8 Hz, 1H), 4.07-3.96 (m, 2H), 3.73 (d, J=16.5 Hz, 1H); $^{19}$F-NMR (300 MHz, CDCl$_3$, ppm): δ −62.8, −72.4, −79.5.

Preparation Example 2: Compound 2

Compound 2 was prepared starting from intermediate 7-2 according to Scheme 8 below:

Scheme 8

Compound 2

4-[2-[5-[3-chloro-5-(trifluoromethyl)phenyl]-5-(trifluoromethyl)-4,5-dihydro-1,2-oxazol-3-yl]ethenyl]-N-(3,3,3-trifluoropropyl)naphthalene-1-carboxamide (Compound 2)

Into a 50-mL round-bottom flask, was placed N,N-dimethylformamide (4 mL), 4-[2-[5-[3-chloro-5-(trifluoromethyl)phenyl]-5-(trifluoromethyl)-4,5-dihydro-1,2-oxazol-3-yl]ethenyl]naphthalene-1-carboxylic acid (7-2, 60 mg, 0.12 mmol, 1.00 equiv), 3,3,3-trifluoropropan-1-amine (8-1, 20 mg, 0.18 mmol, 1.51 equiv), HATU (80 mg, 0.21 mmol, 1.80 equiv), DIEA (50 mg, 0.39 mmol, 3.31 equiv). The resulting solution was stirred for 2 h at room temperature. The crude product was purified by Flash-Prep-HPLC with the following conditions (IntelFlash-1): Column, C18 silica gel; mobile phase, H$_2$O and CH$_3$CN (20% CH$_3$CN increasing to 80% within 25 min); Detector, UV 254 nm. This resulted in 31.3 mg (44%) of 4-[2-[5-[3-chloro-5-(trifluoromethyl)phenyl]-5-(trifluoromethyl)-4,5-dihydro-1,2-oxazol-3-yl]ethenyl]-N-(3,3,3-trifluoropropyl)naphthalene-1-carboxamide (Compound 2) as a white solid. (ES, m/z): 609 [M+H]+; $^1$H-NMR (300 MHz, CDCl$_3$, ppm) δ 8.37-8.32 (m, 1H), 8.14-8.11 (m, 1H), 7.86 (s, 1H), 7.81 (s, 1H), 7.76-7.52 (m, 6H), 7.14 (d, J=16.2 Hz, 1H), 6.24 (br, 1H), 4.15 (d, J=16.8 Hz, 1H), 3.87-3.81 (m, 2H), 3.73 (d, J=16.8 Hz, 1H), 2.66-2.51 (m, 2H); $^{19}$F-NMR (300 MHz, CDCl$_3$, ppm) δ −62.80, −64.80, −79.50.

Preparation Example 3: Compound 3 Shown in Table 59 was Prepared According to Schemes 9 to 11 Shown Below Scheme 9

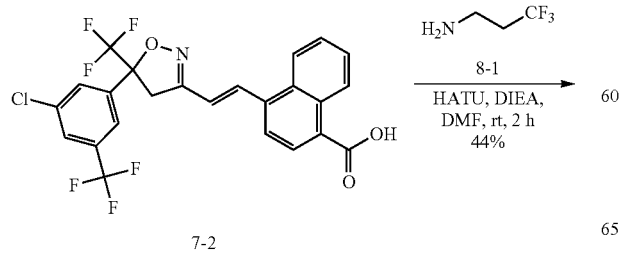

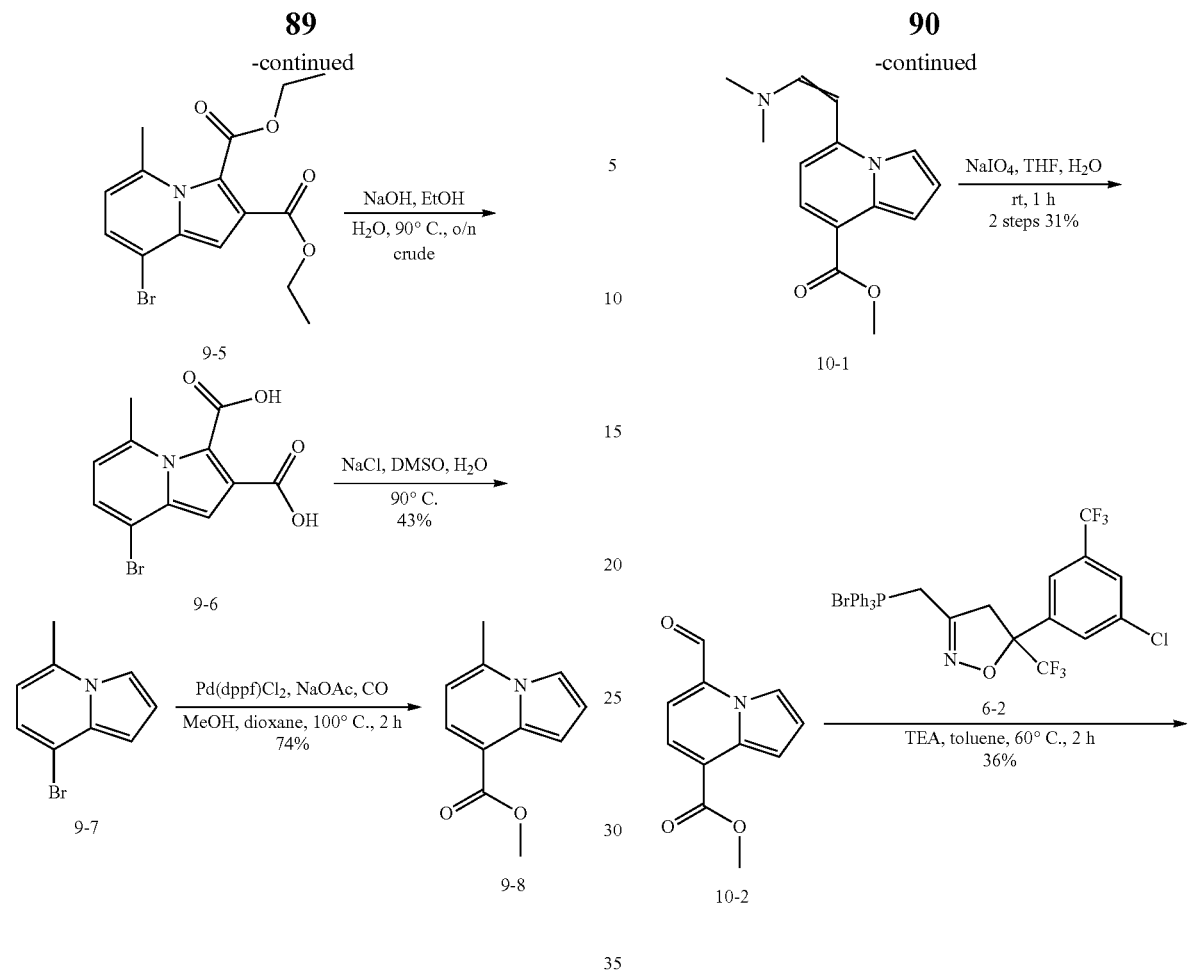
Scheme 10
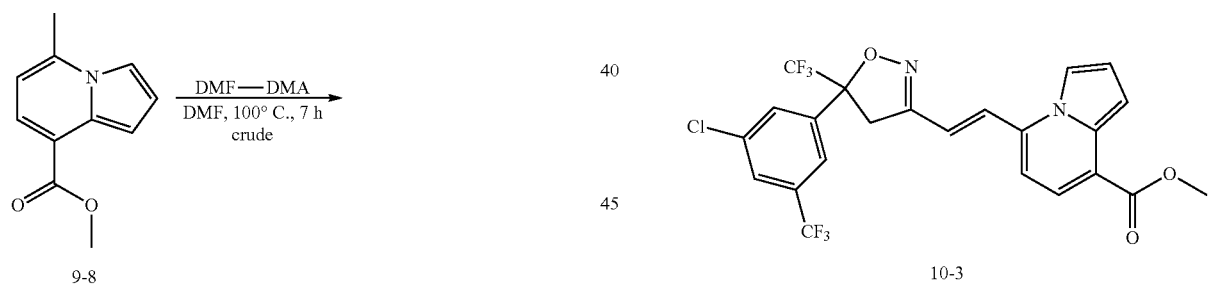
Scheme 11
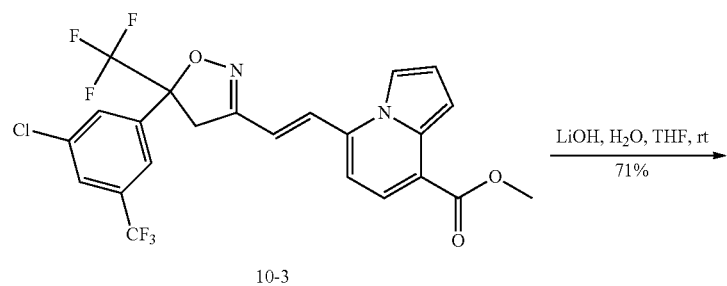

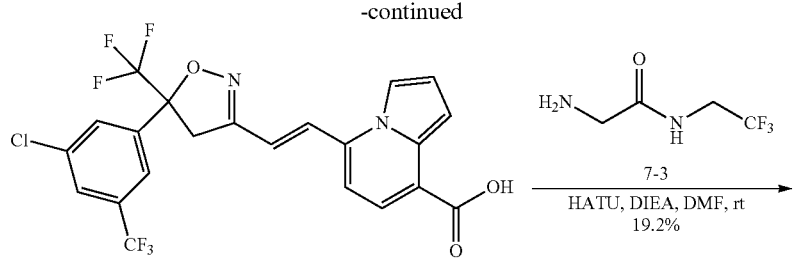

7-3
HATU, DIEA, DMF, rt
19.2%

11-1

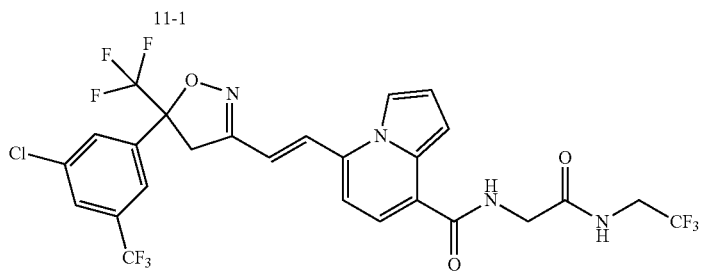

Compound 3

5-bromo-1-(2-ethoxy-2-oxoethyl)-2-methylpyridin-1-ium bromide (9-3)

Into a 1000-mL round-bottom flask, was placed ethyl acetate (200 mL), 5-bromo-2-methylpyridine (9-1, 50 g, 290.66 mmol, 1.00 equiv), ethyl 2-bromoacetate (9-2, 160 g, 1.20 mol, 4.00 equiv). The resulting solution was stirred 3 days at room temperature. The solids were collected by filtration. This resulted in 73.9 g (75%) of 5-bromo-1-(2-ethoxy-2-oxoethyl)-2-methylpyridin-1-ium bromide (9-3) as a white solid.

2,3-diethyl 8-bromo-5-methylindolizine-2,3-dicarboxylate (9-5)

Into a 500-mL round-bottom flask, was placed a solution of 5-bromo-1-(2-ethoxy-2-oxoethyl)-2-methylpyridin-1-ium bromide (9-3, 25 g, 73.74 mmol, 1.00 equiv) in DMSO (200 mL), ethyl prop-2-ynoate (8 g, 81.55 mmol, 1.11 equiv). This was followed by the addition of TEA (25 g, 247.06 mmol, 3.35 equiv) dropwise with stirring at 0° C. The resulting solution was stirred for 2 h at 100° C. and then was quenched by the addition of 500 mL of water/ice. The resulting solution was extracted with 3×200 mL of ethyl acetate and the organic layers combined and dried over anhydrous sodium sulfate. The solids were filtered out. The filtrate was concentrated under vacuum. The residue was applied onto a silica gel column with ethyl acetate/petroleum ether (1/20). This resulted in 16.9 g (64.7%) of 2,3-diethyl 8-bromo-5-methylindolizine-2,3-dicarboxylate (9-5) as brown oil.

8-bromo-5-methylindolizine-2,3-dicarboxylic acid (9-6)

Into a 1-L round-bottom flask, was placed a solution of 2,3-diethyl 8-bromo-5-methylindolizine-2,3-dicarboxylate (9-5, 21 g, 59.29 mmol, 1.00 equiv) in ethanol (200 mL), and a solution of sodium hydroxide (12 g, 300.00 mmol, 5.06 equiv) in water (200 mL). The resulting solution was stirred overnight at 90° C. The resulting mixture was concentrated under vacuum. The pH value of the solution was adjusted to 4 with hydrogen chloride (1 mol/L) and the resulting solution was extracted with 3×100 mL of ethyl acetate. The organic layers were combined and dried over anhydrous sodium sulfate. The solids were filtered out. The filtrate was concentrated under vacuum. This resulted in 10 g (crude) of 8-bromo-5-methylindolizine-2,3-dicarboxylic acid (9-6) as a yellow oil.

8-bromo-5-methylindolizine (9-7)

To a solution of 8-bromo-5-methylindolizine-2,3-dicarboxylic acid (9-6, 10 g, 33.6 mmol) in DMSO (200 mL) was added NaCl (9.8 g, 0.169 mol) in $H_2O$ (200 mL). The resulting solution was stirred overnight at 90° C. The resulting solution was diluted with 500 mL of EA. The resulting mixture was washed with 3×200 mL of $H_2O$. The organic layer was dried over anhydrous sodium sulfate. The solids were filtered out and filtrate was concentrated under vacuum. The residue was applied onto a silica gel column with petroleum ether. This resulted in 3 g (43%) of 8-bromo-5-methylindolizine (9-7) as a brown oil.

Methyl 5-methylindolizine-8-carboxylate (9-8)

Into a 50-mL pressure tank reactor, was placed a solution of 8-bromo-5-methylindolizine (9-7, 2 g, 9.6 mmol, 1 equiv) in dioxane (15 mL), Pd(dppf)$Cl_2$ (0.78 mg), NaOAc (2.35 mg) and MeOH (5 mL). To the above mixture was introduced CO (20 atm). The resulting solution was stirred for 2 h at 100° C. and then the resulting mixture was then concentrated under vacuum. The residue was applied onto a silica gel column with PE. This resulted in 1.34 g (74%) of methyl 5-methylindolizine-8-carboxylate (9-8) as a brown oil.

Methyl 5-[2-(dimethylamino)ethenyl]indolizine-8-carboxylate (10-1)

Into a 100-mL 3-necked round-bottom flask purged and maintained with an inert atmosphere of nitrogen, was placed a solution of methyl 5-methylindolizine-8-carboxylate (9-8, 550 mg, 1 equiv) in DMF (50 mL). This was followed by the addition of DMF-DMA (1.731 g) dropwise with stirring. The resulting solution was stirred for 7 hr at 100° C. and then diluted with 200 mL of EA. The resulting mixture was washed with 3×50 ml of H₂O. The organic layer was dried over anhydrous sodium sulfate. The solids were filtered out. The filtrate was concentrated under vacuum. This resulted in 600 mg (crude) of methyl 5-[2-(dimethylamino)ethenyl]indolizine-8-carboxylate (10-1) as a solid.

Methyl 5-formylindolizine-8-carboxylate (10-2)

Into a 50-mL round-bottom flask, was placed a solution of methyl 5-[2-(dimethylamino)ethenyl]indolizine-8-carboxylate (10-1, 600 mg, 1 mmol, 1 equiv) in THF (20 mL). To the above was added a solution of NaIO₄ (1.05 g) in H₂O (14 mL) with stirring at 0° C. The resulting solution was stirred for 1 h at room temperature and then diluted with 100 mL of EA. The resulting mixture was washed with 2×20 ml of H₂O. The organic layer was dried over anhydrous sodium sulfate. The solids were filtered out and the filtrate was concentrated under vacuum. The residue was applied onto a silica gel column with ethyl acetate/petroleum ether (1:20). This resulted in 183 mg of methyl 5-formylindolizine-8-carboxylate (10-2) as a red oil.

5-[(E)-2-[5-[3-chloro-5-(trifluoromethyl)phenyl]-5-(trifluoromethyl)-4,5-dihydro-1,2-oxazol-3-yl]ethenyl]indolizine-8-carboxylate (10-3)

Into a 50-mL round-bottom flask purged and maintained with an inert atmosphere of nitrogen, was placed a solution of methyl 5-formylindolizine-8-carboxylate (10-2, 100 mg, 1 equiv) in toluene (10 mL), 3-[(bromotriphenyl-1^[5]-phosphanyl)methyl]-5-[3-chloro-5-(trifluoromethyl)phenyl]-5-(trifluoromethyl)-4,5-dihydro-1,2-oxazole (6-2, 275 mg) and TEA (83 mg). The resulting solution was stirred for 2 h at 60° C. and then concentrated under vacuum. The residue was applied onto a silica gel column with ethyl acetate/petroleum ether (1:10). This resulted in 91 mg (36%) of methyl 5-[2-[5-[3-chloro-5-(trifluoromethyl)phenyl]-5-(trifluoromethyl)-4,5-dihydro-1,2-oxazol-3-yl]ethenyl]indolizine-8-carboxylate (10-3) as a red solid.

5-[2-[5-[3-chloro-5-(trifluoromethyl)phenyl]-5-(trifluoromethyl)-4,5-dihydro-1,2-oxazol-3-yl]ethenyl]indolizine-8-carboxylic acid (11-1)

Into a 25-mL round-bottom flask, was placed a solution of methyl 5-[-2-[5-[3-chloro-5-(trifluoromethyl)phenyl]-5-(trifluoromethyl)-4,5-dihydro-1,2-oxazol-3-yl]ethenyl]indolizine-8-carboxylate (10-3, 200 mg, 0.39 mmol, 1 equiv) in THF (5 mL) and a solution of LiOH (81 mg, 3.38 mmol, 8.740 equiv) in H₂O (1 mL). The resulting solution was stirred overnight at room temperature. The pH value of the solution was adjusted to 4 with HCl (1 mol/L). The resulting solution was extracted with 3×10 ml of ethyl acetate dried over anhydrous sodium sulfate. The solids were filtered out and the filtrate was concentrated. This resulted in 138 mg (71%) of 5-[2-[5-[3-chloro-5-(trifluoromethyl)phenyl]-5-(trifluoromethyl)-4,5-dihydro-1,2-oxazol-3-yl]ethenyl]indolizine-8-carboxylic acid (11-1) as a red solid.

2-([5-[2-[5-[3-chloro-5-(trifluoromethyl)phenyl]-5-(trifluoromethyl)-4,5-dihydro-1,2-oxazol-3-yl]ethenyl]indolizin-8-yl]formamido)-N-(2,2,2-trifluoroethyl)acetamide (Compound 3)

Into a 25-mL round-bottom flask, was placed a solution of 5-[2-[5-[3-chloro-5-(trifluorom-ethyl)-4,5-dihydro-1,2-oxazol-3-yl]ethenyl]indolizine-8-carboxylic acid (11-1, 80 mg, 0.16 mmol, 1 equiv) in DMF (3 mL), 2-amino-N-(2,2,2-trifluoroethyl)acetamide (7-3, 37 mg, 0.24 mmol, 1.490 equiv), HATU (121 mg, 0.32 mmol, 2.000 equiv) and DIEA (61 mg, 0.47 mmol, 2.966 equiv). The resulting solution was stirred for 2 h at room temperature. The crude product was purified by Flash-Prep-HPLC with the following conditions (IntelFlash-1): Column, C18 silica gel; mobile phase, H₂O and CH₃CN (40% CH₃CN increasing to 100% within 10 min); Detector, UV 254 nm. This resulted in 19.6 mg (19.22%) of 2-([5-[2-[5-[3-chloro-5-(trifluoromethyl)phenyl]-5-(trifluoromethyl)-4,5-dihydro-1,2-oxazol-3-yl]ethenyl]indolizin-8-yl]formamido)-N-(2,2,2-trifluoroethyl)acetamide (Compound 3) as an orange solid. (ES, m/z): 641 [M+H]⁺; ¹H-NMR (300 MHz, CDCl₃, ppm) δ 7.84 (s, 1H), 7.78 (s, 1H), 7.74 (s, 1H), 7.57 (s, 1H), 7.34-7.26 (m, 1H), 7.11-7.02 (m, 4H), 6.91 (d, J=7.2 Hz, 1H), 6.76 (br, 1H), 4.30 (d, J=5.4 Hz, 2H), 4.09 (d, J=17.1 Hz, 1H), 4.02-3.94 (m, 2H), 3.68 (d, J=16.8 Hz, 1H); ¹⁹F-NMR (CDCl₃, ppm): δ −62.83, −72.45, −79.57.

Preparation Example 4: Compound 4 Shown in Table 59 was Prepared According to Scheme 12 Shown Below

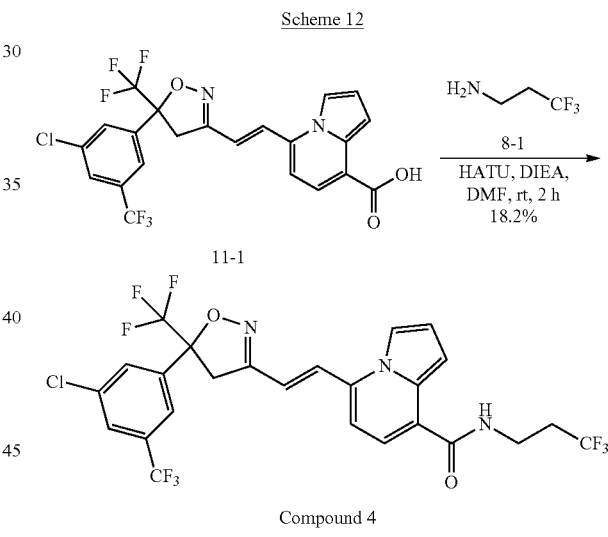

Scheme 12

5-(2-(5-(3-chloro-5-(trifluoromethyl)phenyl)-5-(trifluoromethyl)-4,5-dihydroisoxazol-3-yl)vinyl)-N-(3,3,3-trifluoropropyl)indolizine-8-carboxamide (Compound 4)

Into a 25-mL round-bottom flask, was placed a solution of 5-(2-(5-(3-chloro-5-(trifluoromethyl)phenyl)-5-(trifluoromethyl)-4,5-dihydroisoxazol-3-yl)vinyl)indolizine-8-carboxylic acid (11-1, 80 mg, 0.16 mmol, 1 equiv) in DMF (3 mL), 3,3,3-trifluoropropan-1-amine (8-1, 27 mg, 0.24 mmol, 1.490 equiv), HATU (121 mg, 0.32 mmol, 2.000 equiv), DIEA (61 mg, 0.47 mmol, 2.966 equiv). The resulting solution was stirred for 2 h at room temperature. The crude product was purified by Flash-Prep-HPLC with the following conditions (IntelFlash-1): Column, C18 silica gel; mobile phase, H₂O and CH₃CN (40% CH₃CN increasing to 100% within 10 min); Detector, UV 254 nm. This resulted in 17.3 mg (18.2%) of 5-(2-(5-(3-chloro-5-(trifluoromethyl)phenyl)-5-(trifluoromethyl)-4,5-dihydroisoxazol-3-yl)vinyl)-N-(3,3,3-trifluoropropyl)indolizine-8-carboxamide (Compound 4) as an orange solid. (ES, m/z): 598 [M+H]+; 1H-NMR (300 MHz, CDCl3, ppm) δ 7.84 (s, 1H), 7.78 (s, 1H), 7.73 (s, 1H), 7.56 (s, 1H), 7.35-7.25 (m, 1H), 7.20 (d, J=7.2 Hz, 1H), 7.09-7.01 (m, 2H), 6.92-6.90 (m, 2H), 6.53 (br, 1H), 4.08 (d, J=16.8 Hz, 1H), 3.78-3.75 (m, 2H), 3.67 (d, J=17.1 Hz, 1H), 2.62-2.40 (m, 2H); 19F-NMR (CDCl3, ppm) δ −62.83, −65.39, −79.56.
Preparation Example 5: Compound 5 Shown in Table 59 was Prepared According to Schemes 13-15 Shown Below
Scheme 13
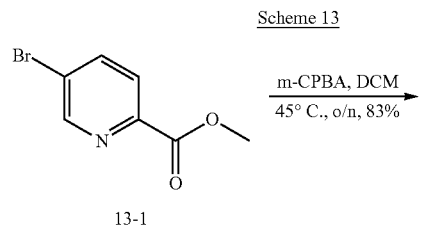
13-1
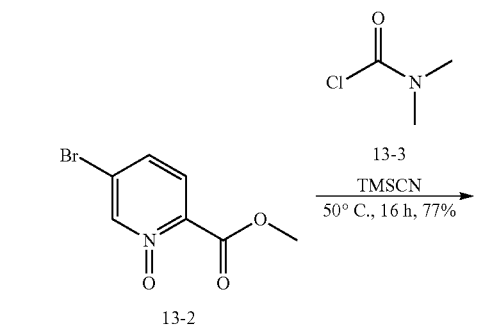
13-2
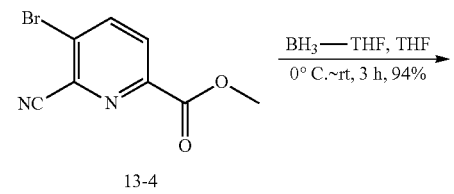
13-4
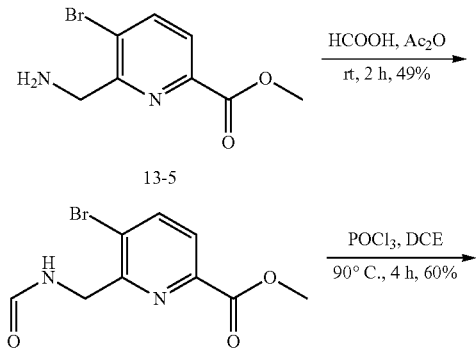
13-5
13-6
Scheme 14
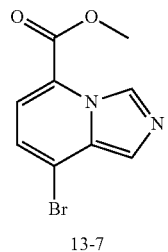
13-7
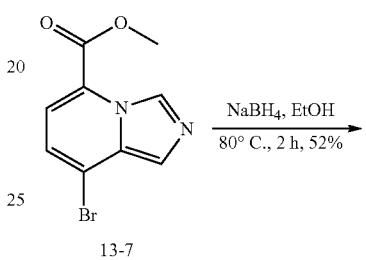
13-7
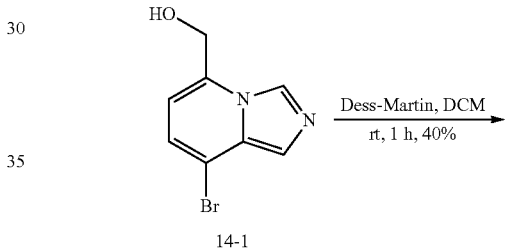
14-1
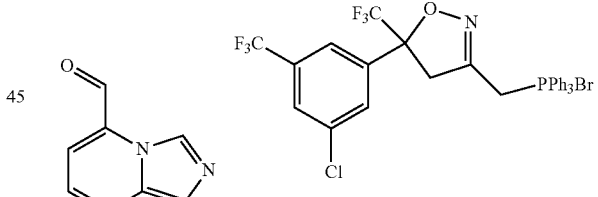
14-2
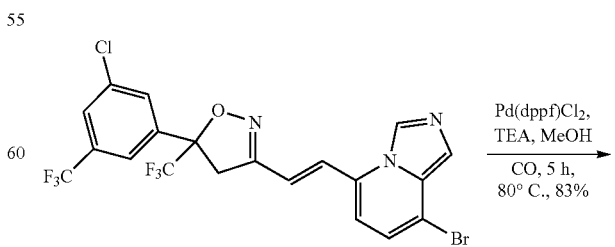
14-3

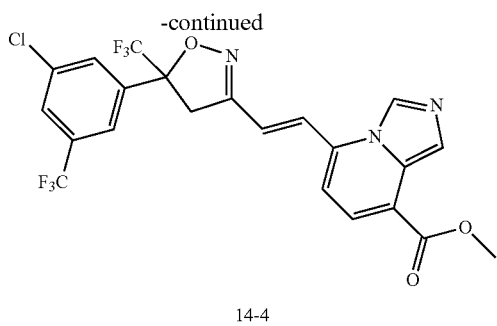

14-4

Scheme 15

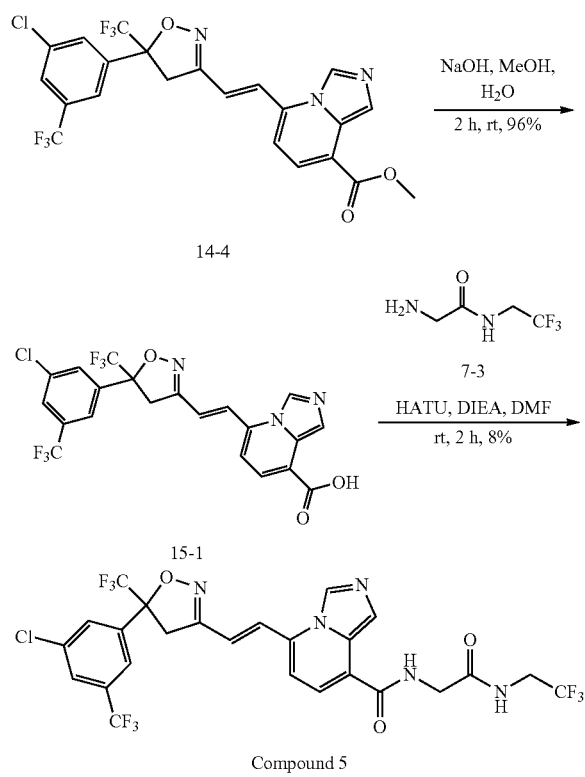

Methyl 5-bromo-6-cyanopyridine-2-carboxylate (13-4)

Into a 500-mL round-bottom flask, was placed methyl 5-bromo-1-oxo-1ˆ[5]-pyridine-2-carboxylate (13-2, 25 g, 107.74 mmol, 1.00 equiv), TMSCN (130 mL), N,N-dimethylcarbamoyl chloride (100 mL). The resulting solution was stirred for 16 h at 50° C. The reaction mixture was cooled to 0° C. with an ice/salt bath. The pH value of the solution was adjusted to 8 with sodium hydroxide. The resulting solution was extracted with 3×500 mL of ethyl acetate. The combined organic layers were dried over anhydrous sodium sulfate and concentrated under vacuum. The residue was applied onto a silica gel column with ethyl acetate/petroleum ether (1/4). This resulted in 20 g (77%) of methyl 5-bromo-6-cyanopyridine-2-carboxylate (13-4) as a white solid.

Methyl 6-(aminomethyl)-5-bromopyridine-2-carboxylate (13-5)

Into a 500-mL 3-necked round-bottom flask, was placed methyl 5-bromo-6-cyanopyridine-2-carboxylate (13-4, 10.5 g, 43.56 mmol, 1.00 equiv), tetrahydrofuran (155 mL). This was followed by the addition of $BH_3$-THF (219 mL) dropwise with stirring at 0° C. The resulting solution was stirred for 3 h at room temperature. The reaction was then quenched by the addition of 100 mL of methanol. The resulting mixture was concentrated under vacuum. This resulted in 10 g (94%) of methyl 6-(aminomethyl)-5-bromopyridine-2-carboxylate (13-5) as a light yellow solid.

Methyl 5-bromo-6-(formamidomethyl)pyridine-2-carboxylate (13-6)

Into a 500-mL round-bottom flask, was placed methyl 6-(aminomethyl)-5-bromopyridine-2-carboxylate (13-5, 6.4 g, 26.11 mmol, 1.00 equiv), $(CH_3CO)_2O$ (60 mL), $HCO_2H$ (200 mL). The resulting solution was stirred for 2 h at room temperature. The resulting mixture was concentrated under vacuum and the residue was dissolved in 100 mL of $H_2O$. The pH value of the solution was adjusted to 9 with potassium carbonate (1N). The resulting solution was extracted with 3×100 mL of dichloromethane and the organic layer were collected and dried over anhydrous sodium sulfate and concentrated under vacuum. This resulted in 3.5 g (49%) of methyl 5-bromo-6-(formamidomethyl)pyridine-2-carboxylate (13-6) as a brown oil.

Methyl 8-bromoimidazo[1,5-a]pyridine-5-carboxylate (13-7)

Into a 250-mL round-bottom flask purged and maintained with an inert atmosphere of nitrogen, was placed methyl 5-bromo-6-(formamidomethyl)pyridine-2-carboxylate (13-6, 2.85 g, 10.48 mmol, 1.00 equiv), 1.2-Dichloroethane (30 mL) and $POCl_3$ (4.78 g, 31.43 mmol, 3.01 equiv). The resulting solution was stirred for 4 h at 90° C. The reaction was then quenched by the addition of 100 mL of water/ice. The pH value of the solution was adjusted to 10 with sodium hydroxide (1N). The resulting solution was extracted with 3×100 mL of ethyl acetate, the organic layers were combined and dried over anhydrous sodium sulfate and concentrated under vacuum. This resulted in 1.6 g (60%) of methyl 8-bromoimidazo[1,5-a]pyridine-5-carboxylate (13-7) as brown oil.

5-bromo-2-(methoxycarbonyl)-1ˆ[5]-pyridin-1-olate (13-2)

Into a 1-L round-bottom flask, was placed methyl 5-bromopyridine-2-carboxylate (13-1, 45 g, 208.30 mmol, 1.00 equiv) and dichloromethane (450 mL). This was followed by the addition of m-CPBA (108.125 g, 626.56 mmol, 3.01 equiv) in portions at 0° C. The resulting solution was stirred overnight at 45° C. The resulting mixture was concentrated under vacuum. The residue was dissolved in 500 mL of EA and the pH value of the solution was adjusted to 8 with sodium carbonate. The resulting solution was extracted with 3×300 mL of ethyl acetate. The organic layer was collected and dried over anhydrous sodium sulfate and concentrated under vacuum. This resulted in 40 g (83%) of 5-bromo-2-(methoxycarbonyl)-1ˆ[5]-pyridin-1-olate (13-2) as a light yellow solid.

[8-bromoimidazo[1,5-a]pyridin-5-yl]methanol (14-1)

Into a 250-mL round-bottom flask, was placed methyl 8-bromoimidazo[1,5-a]pyridine-5-carboxylate (13-7, 1.5 g, 5.88 mmol, 1.00 equiv), ethanol (80 mL) and NaBH$_4$ (449 mg, 11.87 mmol, 2.02 equiv). The resulting solution was stirred for 2 h at 80° C. and the resulting mixture was concentrated under vacuum. The residue was dissolved with 100 mL of EA and the resulting mixture was washed with 3×50 mL of H$_2$O. The organic layer was collected and dried over anhydrous sodium sulfate and concentrated under vacuum. The residue was applied onto a silica gel column with PE (100%) and eluted with dichloromethane/methanol (20/1). This resulted in 700 mg (52%) of [8-bromoimidazo[1,5-a]pyridin-5-yl]methanol (14-1) as a brown solid.

8-bromoimidazo[1,5-a]pyridine-5-carbaldehyde (14-2)

Into a 100-mL round-bottom flask, was placed [8-bromoimidazo[1,5-a]pyridin-5-yl]methanol (14-1, 700 mg, 3.08 mmol, 1.00 equiv), dichloromethane (20 mL) and Dess-Martin periodinane (1.45 g, 3.42 mmol, 1.11 equiv). The resulting solution was stirred for 1 h at room temperature. The reaction was then quenched by the addition of 100 mL of water. The resulting solution was extracted with 3×50 mL of dichloromethane. The combined organic layers were dried over anhydrous sodium sulfate and concentrated under vacuum. The residue was applied onto a silica gel column with ethyl acetate/petroleum ether (1/3). This resulted in 280 mg (40%) of 8-bromoimidazo[1,5-a]pyridine-5-carbaldehyde (14-2) as a yellow solid.

3-[2-[8-bromoimidazo[1,5-a]pyridin-5-yl]ethenyl]-5-[3-chloro-5-(trifluoromethyl)phenyl]-5-(trifluoromethyl)-4,5-dihydro-1,2-oxazole (14-3)

Into a 50-mL round-bottom flask, was placed 3-[(bromotriphenyl-^[5]-phosphanyl)methyl]-5-[3-chloro-5-(trifluoromethyl)phenyl]-5-(trifluoromethyl)-4,5-dihydro-1,2-oxazole (5-2, 699 mg, 1.04 mmol, 1.00 equiv), 8-bromoimidazo[1,5-a]pyridine-5-carbaldehyde (14-2, 280 mg, 1.24 mmol, 1.20 equiv), potassium carbonate (431.3 mg, 3.12 mmol, 3.00 equiv) and toluene (10 mL). The resulting solution was stirred for 3 h at 95° C. The reaction mixture was then cooled to room temperature. The resulting mixture was concentrated under vacuum and the residue was applied onto a silica gel column with ethyl acetate/petroleum ether (1/3). This resulted in 430 mg (77%) of 3-[2-[8-bromoimidazo[1,5-a]pyridin-5-yl]ethenyl]-5-[3-chloro-5-(trifluoromethyl)phenyl]-5-(trifluoromethyl)-4,5-dihydro-1,2-oxazole (14-3) as a light yellow solid.

Methyl 5-[2-[5-[3-chloro-5-(trifluoromethyl)phenyl]-5-(trifluoromethyl)-4,5-dihydro-1,2-oxazol-3-yl]ethenyl]imidazo[1,5-a]pyridine-8-carboxylate (14-4)

Into a 50-mL pressure tank reactor, was placed 3-[2-[8-bromoimidazo[1,5-a]pyridin-5-yl]ethenyl]-5-[3-chloro-5-(trifluoromethyl)phenyl]-5-(trifluoromethyl)-4,5-dihydro-1,2-oxazole (14-3, 200 mg, 0.37 mmol, 1.00 equiv), Pd(dppf)Cl$_2$ (81.7 mg, 0.11 mmol, 0.30 equiv), triethylamine (113 mg, 1.12 mmol, 3.01 equiv) and methanol (20 mL). To this mixture was introduced CO (g). The resulting solution was stirred for 5 h at 80° C. and then cooled to room temperature. The resulting mixture was concentrated under vacuum. The residue was applied onto a silica gel column with ethyl acetate/petroleum ether (1/2). This resulted in 160 mg (83%) of methyl 5-[2-[5-[3-chloro-5-(trifluoromethyl)phenyl]-5-(trifluoromethyl)-4,5-dihydro-1,2-oxazol-3-yl]ethenyl]imidazo[1,5-a]pyridine-8-carboxylate (14-4) as a brown solid.

5-[2-[5-[3-chloro-5-(trifluoromethyl)phenyl]-5-(trifluoromethyl)-4,5-dihydro-1,2-oxazol-3-yl]ethenyl]imidazo[1,5-a]pyridine-8-carboxylic acid (15-1)

Into a 50-mL round-bottom flask, was placed methyl 5-[2-[5-[3-chloro-5-(trifluoromethyl)phenyl]-5-(trifluoromethyl)-4,5-dihydro-1,2-oxazol-3-yl]ethenyl]imidazo[1,5-a]pyridine-8-carboxylate (14-4, 160 mg, 0.31 mmol, 1.00 equiv), sodium hydroxide (62 mg, 1.55 mmol, 5.02 equiv) in water (2 mL) and methanol (5 mL). The resulting solution was stirred for 2 h at room temperature. The pH value of the solution was adjusted to 4 with hydrogen chloride (1 N). The resulting solution was extracted with 3×20 mL of ethyl acetate. The organic layer was collected and dried over anhydrous sodium sulfate and concentrated under vacuum. This resulted in 150 mg (96%) of 5-[2-[5-[3-chloro-5-(trifluoromethyl)phenyl]-5-(trifluoromethyl)-4,5-dihydro-1,2-oxazol-3-yl]ethenyl]imidazo[1,5-a]pyridine-8-carboxylic acid (15-1) as a brown solid.

2-([5-[2-[5-[3-chloro-5-(trifluoromethyl)phenyl]-5-(trifluoromethyl)-4,5-dihydro-1,2-oxazol-3-yl]ethenyl]imidazo[1,5-a]pyridin-8-yl]formamido)-N-(2,2,2-trifluoroethyl)acetamide (Compound 5)

Into a 50-mL round-bottom flask, was placed 5-[2-[5-[3-chloro-5-(trifluoromethyl)phenyl]-5-(trifluoromethyl)-4,5-dihydro-1,2-oxazol-3-yl]ethenyl]imidazo[1,5-a]pyridine-8-carboxylic acid (15-1, 80 mg, 0.16 mmol, 1.00 equiv), 2-amino-N-(2,2,2-trifluoroethyl)acetamide (7-3, 49.6 mg, 0.32 mmol, 2.00 equiv), HATU (121 mg, 0.32 mmol, 2.00 equiv), DIEA (82.1 mg, 0.64 mmol, 4.00 equiv) and N,N-dimethylformamide (5 mL). The resulting solution was stirred for 2 h at room temperature. The crude product was purified by Flash-Prep-HPLC with the following conditions (IntelFlash-1): Column, C18 silica gel; mobile phase, H$_2$O and CH$_3$CN (30% CH$_3$CN increasing to 65% within 25 min); Detector, UV 220 nm. This resulted in 7.9 mg (8%) of 2-([5-[2-[5-[3-chloro-5-(trifluoromethyl)phenyl]-5-(trifluoromethyl)-4,5-dihydro-1,2-oxazol-3-yl]ethenyl]imidazo[1,5-a]pyridin-8-yl]formamido)-N-(2,2,2-trifluoroethyl)acetamide (Compound 5) as an orange solid. (ES, m/z): 642 [M+H]$^+$; $^1$H-NMR (300 MHz, CD$_3$OD, ppm) δ 8.81 (s, 1H), 7.96-7.88 (m, 4H), 7.53 (s, 2H), 7.44 (d, J=7.2 Hz, 1H), 7.28 (d, J=7.2 Hz, 1H), 4.36 (d, J=17.7 Hz, 1H), 4.15-4.06 (m, 3H), 4.02-3.93 (m, 2H).

Preparation Example 6: Compound 6 Shown in Table 59 was Prepared According to Scheme 16 Shown Below Scheme 16

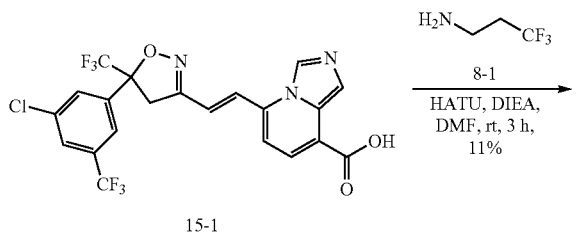

15-1

-continued

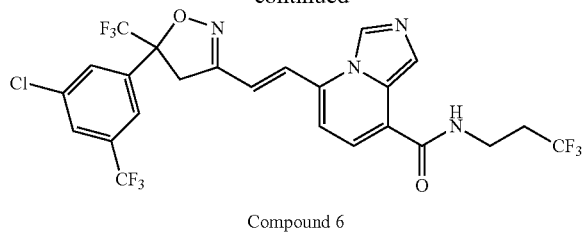

Compound 6

5-[2-[5-[3-chloro-5-(trifluoromethyl)phenyl]-5-(trifluoromethyl)-4,5-dihydro-1,2-oxazol-3-yl]ethenyl]-N-(3,3,3-trifluoropropyl)imidazo[1,5-a]pyridine-8-carboxamide (Compound 6)

Into a 50-mL round-bottom flask, was placed 5-[2-[5-[3-chloro-5-(trifluoromethyl)phenyl]-5-(trifluoromethyl)-4,5-dihydro-1,2-oxazol-3-yl]ethenyl]imidazo[1,5-a]pyridine-8-carboxylic acid (15-1, 80 mg, 0.16 mmol, 1.00 equiv), 3,3,3-trifluoropropan-1-amine (8-1, 36.3 mg, 0.32 mmol, 2.02 equiv), HATU (121 mg, 0.32 mmol, 2.00 equiv), DIEA (82 mg, 0.63 mmol, 4.00 equiv) and N,N-dimethylformamide (5 mL). The resulting solution was stirred for 3 h at room temperature. The crude product was purified by Flash-Prep-HPLC with the following conditions (IntelFlash-1): Column, C18 silica gel; mobile phase, $H_2O$ and $CH_3CN$ (30% $CH_3CN$ increasing to 68% within 25 min); Detector, UV 220 nm. This resulted in 10.9 mg (11%) of 5-[2-[5-[3-chloro-5-(trifluoromethyl)phenyl]-5-(trifluoromethyl)-4,5-dihydro-1,2-oxazol-3-yl]ethenyl]-N-(3,3,3-trifluoropropyl)imidazo[1,5-a]pyridine-8-carboxamide (Compound 6) as an orange solid. (ES, m/z): 599 [M+H]$^+$; $^1$H-NMR (300 MHz, $CDCl_3$, ppm) δ 8.67-8.56 (br, 1H), 7.95 (br, 1H), 7.85 (s, 1H), 7.79 (s, 1H), 7.74 (s, 1H), 7.40-7.28 (m, 2H), 7.12-6.98 (m, 2H), 6.50 (br, 1H), 4.12 (d, J=16.2 Hz, 1H), 3.85-3.71 (m, 3H), 2.64-2.46 (m, 2H)

Efficacy of Compounds Against *A. aegypti* Mosquitos

Compounds were formulated in 100% DMSO are added to microtiter plates containing 180 μl of diluted LB media (Luria-Bertani media is a combination of tryptone, salt and yeast extract). Ten *A. aegypti* L1 larvae are added and the plates are incubated at 25° C. for 48 h. The efficacy of a compound is determined based on the motility of the larvae as compared to average motility of control wells containing DMSO only. A dose response assay was conducted to determine an $EC_{50}$ value. Compounds 1, 2, 5 and 6 were found to have $EC_{50}$ values of ≤20 μM and Compounds 5 and 6 were found to have $EC_{50}$ values of less than 15 μM.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A pesticidal isoxazoline compound of formula (I):

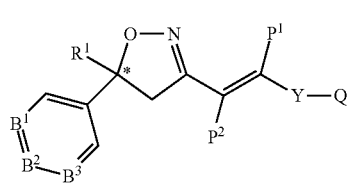

(I)

wherein:
the asterisk (*) signifies a chiral quaternary center;
the squiggly bond (∿) signifies that the double bond may be in the cis- or trans-configuration with respect to $P^1$ and $P^2$;
$B^1$, $B^2$ and $B^3$ are each independently C—R or N;
each R is independently H, halogen, cyano, —$NO_2$, alkyl, haloalkyl, alkoxy, haloalkoxy, alkylthio, haloalkylthio, alkylsulfinyl, haloalkylsulfinyl, alkylsulfonyl, haloalkylsulfonyl, —$SF_5$, —C(=S)—$NH_2$, alkylamino, dialkylamino or alkoxycarbonyl;
$R^1$ is $C_1$-$C_3$alkyl or $C_1$-$C_3$haloalkyl;
$P^1$ and $P^2$ are independently hydrogen, halogen, cyano, nitro, alkyl, haloalkyl, alkenyl, haloalkenyl, alkynyl, haloalkynyl, cycloalkyl, alkoxy, haloalkoxy, alkylthio, haloalkylthio, alkylsulfinyl, haloalkylsulfinyl, alkylsulfonyl or haloalkylsulfonyl;
Y is Y-2, Y-4, Y-5 or Y-6:

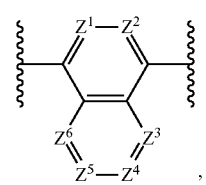

Y-2

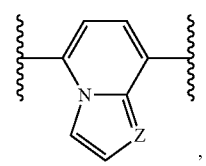

Y-4

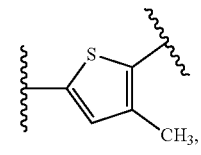

Y-5

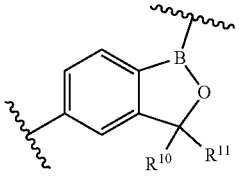

Y-6 wherein Z, $Z^1$, $Z^2$, $Z^3$, $Z^4$, $Z^5$ and $Z^6$ are independently C—H or N, and wherein $R^{10}$ and $R^{11}$ are independently H, $C_1$-$C_3$alkyl or $C_1$-$C_3$haloalkyl;
Q is X—$NR^2R^3$, OH, $NH_2$, alkoxy, haloalkoxy, alkylamino, haloalkylamino, dialkylamino, dihaloalkylamino, thiol, alkylthio, haloalkylthio, alkylsulfinyl, haloalkylsulfinyl, alkylsulfonyl, haloalkylsulfonyl, —$SF_5$, —C(=S)—$NH_2$, or an optionally substituted 5- or 6-membered carbocyclyl, heterocyclyl, heteroaryl ring, wherein the optional substituents of said carbocyclyl, heterocyclyl or heteroaryl ring are selected from halogen, alkyl, haloalkyl, alkoxy, haloalkoxy, alkylthio, haloalkylthio, alkylsulfinyl, haloalkylsulfinyl, alkylsulfonyl, haloalkylsulfonyl, alkylamino, dialkylamino, alkylcarbonyl, haloalkylcarbonyl, alkoxycarbonyl, haloalkoxycarbonyl, —$SF_5$, —CN, —$NO_2$ and —C(=S)—$NH_2$; or the groups T1 or T2:

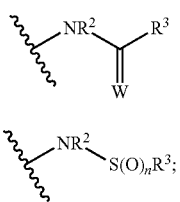
T1

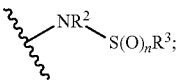
T2 or
Y is Y-3 wherein Q is (—CH$_2$—)(—CH$_2$—)N—R$^3$

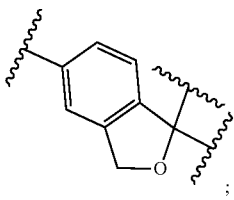
Y-3

W is O or S;
X is (CH$_2$)$_n$, CH(CH$_3$), CH(CN), C(=O) or C(=S);
R$^2$ is H, alkyl, alkenyl, alkynyl, cycloalkyl, alkylcycloalkyl, cycloalkylalkyl, alkylcarbonyl or alkoxycarbonyl;
R$^3$ is H, OR$^7$, NR$^8$R$^9$ or Q$^1$; or alkyl, haloalkyl, alkenyl, haloalkenyl, alkynyl, haloalkynyl, cycloalkyl, alkylcycloalkyl, cycloalkylalkyl, alkylcarbonyl, alkoxycarbonyl, aminocarbonyl, alkylaminocarbonyl or dialkylaminocarbonyl, each optionally substituted with one or more substituents independently selected from R$^4$; or
when Q is X—NR$^2$R$^3$, R$^2$ and R$^3$ taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of alkyl, halogen, —CN, —NO$_2$ and alkoxy;
each R$^4$ is independently halogen; alkyl, cycloalkyl, alkoxy, alkylthio, haloalkylthio, alkylsulfinyl, haloalkylsulfinyl, alkylsulfonyl, haloalkylsulfonyl, alkylamino, haloalkylamino, dialkylamino, dihaloalkylamino, cycloalkylamino, alkylcarbonyl, alkoxycarbonyl, alkylaminocarbonyl, dialkylaminocarbonyl, haloalkylcarbonyl, haloalkoxycarbonyl, haloalkylaminocarbonyl, dihaloalkylaminocarbonyl, hydroxy, —SF$_5$, —C(=S)NH$_2$, —NH$_2$, —CN or —NO$_2$; or Q$^2$;
each R$^5$ is independently halogen, alkoxy, haloalkoxy, alkylthio, haloalkylthio, alkylsulfinyl, haloalkylsulfinyl, alkylsulfonyl, haloalkylsulfonyl, alkylamino, dialkylamino, alkoxycarbonyl, —SF$_5$, —C(=S)NH$_2$, —CN or —NO$_2$;
each R$^6$ is independently halogen, alkyl, haloalkyl, cycloalkyl, halocycloalkyl, alkoxy, haloalkoxy, alkylthio, haloalkylthio, alkylsulfinyl, haloalkylsulfinyl, alkylsulfonyl, haloalkylsulfonyl, alkylamino, dialkylamino, —SF$_5$, —C(=S)NH$_2$, —CN, —NO$_2$, phenyl or pyridinyl;
R$^7$ is H; or alkyl, alkenyl, alkynyl, cycloalkyl, alkylcycloalkyl or cycloalkylalkyl, each optionally substituted with one or more halogens;

R$^8$ is H, alkyl, alkenyl, alkynyl, cycloalkyl, alkylcycloalkyl, cycloalkylalkyl, alkylcarbonyl or alkoxycarbonyl;
R$^9$ is H; Q$^3$; or alkyl, alkenyl, alkynyl, cycloalkyl, alkylcycloalkyl or cycloalkylalkyl, each optionally substituted with one or more substituents independently selected from R$^4$; or
R$^8$ and R$^9$ taken together with the nitrogen to which they are attached form a ring containing 2 to 6 atoms of carbon and optionally one additional atom selected from the group consisting of N, S and O, said ring optionally substituted with 1 to 4 substituents independently selected from the group consisting of alkyl, halogen, —CN, —NO$_2$ and alkoxy;
Q$^1$ is a phenyl ring, a 5- or 6-membered heterocyclic ring, or an 8-, 9- or 10-membered fused bicyclic ring system optionally containing one to three heteroatoms selected from up to 1 O, up to 1 S and up to 3 N, each ring or ring system optionally substituted with one or more substituents independently selected from R$^5$;
Q$^2$ is independently a phenyl ring or a 5- or 6-membered heterocyclic ring, each ring optionally substituted with one or more substituents independently selected from R$^6$;
Q$^3$ is a phenyl ring or a 5- or 6-membered heterocyclic ring, each ring optionally substituted with one or more substituents independently selected from R$^6$; and
n is 0, 1 or 2.

2. The pesticidal isoxazoline compound of claim 1, wherein B$^1$, B$^2$ and B$^3$ are each independently C—R; and R is H, halogen, C$_1$-C$_3$alkyl, C$_1$-C$_3$haloalkyl, C$_1$-C$_3$alkoxy, C$_1$-C$_3$haloalkoxy, C$_1$-C$_3$alkylthio, C$_1$-C$_3$haloalkylthio or SF$_5$.

3. The pesticidal isoxazoline compound of claim 1, wherein one or two of B$^1$, B$^2$ and B$^3$ are each N and the others of B$^1$, B$^2$ and B$^3$ are C—R; and R is H, halogen, C$_1$-C$_3$alkyl, C$_1$-C$_3$haloalkyl, C$_1$-C$_3$alkoxy, C$_1$-C$_3$haloalkoxy, C$_1$-C$_3$alkylthio, C$_1$-C$_3$haloalkylthio or SF$_5$.

4. The pesticidal isoxazoline compound of any of claim 1, 2 or 3, wherein R$^1$ is CF$_3$.

5. The pesticidal isoxazoline compound of claim 1, wherein Y is Y-2:

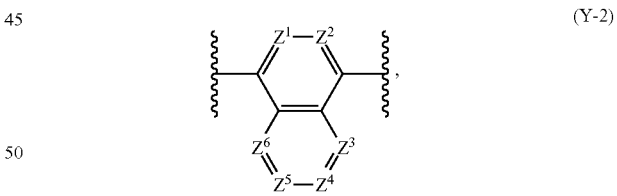
(Y-2)

wherein Z$^1$, Z$^2$, Z$^3$, Z$^4$, Z$^5$ and Z$^6$ are CH or N, provided at at most 3 of Z$^1$, Z$^2$, Z$^3$, Z$^4$, Z$^5$ and Z$^6$ are N.

6. The pesticidal isoxazoline compound of claim 1, wherein Y is Y-4:

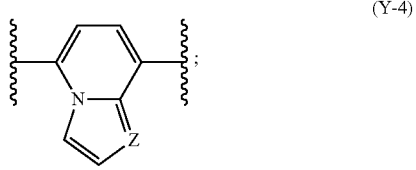
(Y-4)

wherein Z is N or CH.

7. The pesticidal isoxazoline compound of claim 1, wherein Y is Y-5:

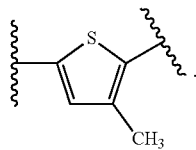 [SMILES: *c1cc(C)c(*)s1]

8. The pesticidal isoxazoline compound of claim 1, wherein Y is Y-3:

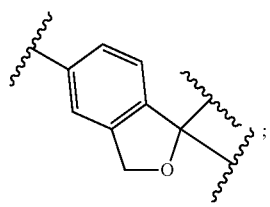

(Y-3)

and
Q is group (—CH$_2$—)(—CH$_2$—)N—R$^3$.

9. The pesticidal isoxazoline compound of claim 1, wherein y is Y-6:

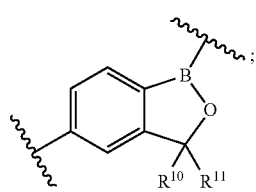

(Y-6)

wherein R$^{10}$ and R$^{11}$ are independently H, C$_1$-C$_3$alkyl or C$_1$-C$_3$haloalkyl.

10. The pesticidal isoxazoline compound of claim 1, wherein:
Q is X—NR$^2$R$^3$;
R$^2$ is H or C$_1$-C$_3$alkyl; and
R$^3$ is C$_1$-C$_3$alkyl optionally substituted by halogen, alkylthio, haloalkylthio, alkylaminocarbonyl, dialkylaminocarbonyl, haloalkylaminocarbonyl or dihaloalkylaminocarbonyl.

11. The pesticidal isoxazoline compound of claim 1, wherein:
Q is T1;
R$^2$ is H or C$_1$-C$_3$alkyl; and
R$^3$ is Q$^1$; or alkyl, haloalkyl, alkenyl, haloalkenyl, alkynyl, haloalkynyl, cycloalkyl, alkylcycloalkyl, cycloalkylalkyl, alkylcarbonyl, alkoxycarbonyl, aminocarbonyl, alkylaminocarbonyl or dialkylaminocarbonyl, each optionally substituted with one or more substituents independently selected from R$^4$.

12. The pesticidal isoxazoline compound of claim 1, wherein:
Q is T2;
R$^2$ is H or C$_1$-C$_3$alkyl; and
R$^3$ is Q$^1$; or alkyl, haloalkyl, alkenyl, haloalkenyl, alkynyl, haloalkynyl, cycloalkyl, alkylcycloalkyl, cycloalkylalkyl, alkylcarbonyl, alkoxycarbonyl, aminocarbonyl, alkylaminocarbonyl or dialkylaminocarbonyl, each optionally substituted with one or more substituents independently selected from R$^4$.

13. The pesticidal isoxazoline compound of claim 1, wherein:
Y is Y-2 or Y-4;
B$^1$, B$^2$ and B$^3$ are independently C—H, C—Cl, C—F or C—CF$_3$;
R$^1$ is CF$_3$;
P$^1$ and P$^2$ are each independently hydrogen, halogen, cyano, C$_1$-C$_8$alkyl, C$_1$-C$_8$haloalkyl or C$_3$-C$_8$cycloalkyl;
Q is X—NR$^2$R$^3$;
X is C(=O) or C(=S);
R$^2$ is H or C$_1$-C$_3$alkyl; and
R$^3$ is C$_1$-C$_3$haloalkylcarbonyl or C$_1$-C$_3$alkyl optionally substituted by halogen, alkylthio, haloalkylthio, alkylaminocarbonyl, dialkylaminocarbonyl, haloalkylaminocarbonyl or dihaloalkylaminocarbonyl.

14. The pesticidal isoxazoline compound of claim 12, wherein:
X is C(=O);
R$^2$ is H;
R$^3$ is —C(=O)CF$_3$, —C(=O)CH$_2$CF$_3$, —C(=O)CH$_2$CH$_2$CF$_3$, -CH$_2$C(=O)NHCH$_2$CF$_3$ or —CH$_2$CH$_2$SCH$_3$.

15. The pesticidal isoxazoline compound of claim 13 or 14, wherein Y is Y-2.

16. The pesticidal isoxazoline compound of claim 13 or 14, wherein Y is Y-4.

17. The pesticidal isoxazoline compound of claim 1 wherein the isoxazoline compound is substantially enriched in the (S)-enantiomer.

18. A pesticidal composition comprising an effective amount of the isoxazoline compound of formula (I) in claim 1, or an agriculturally acceptable salt thereof, in combination with a agriculturally acceptable carrier.

19. A parasiticidal composition comprising an effective amount of the isoxazoline compound of formula (I) in claim 1, or a pharmaceutically acceptable salt thereof, in combination with a pharmaceutically acceptable carrier.

20. A method for controlling pests on crops, plants, plant propagation material or material derived from wood, which comprises treating the crops, plants, plant propagation material, or the soil in which the infected plant grows, or the wood-derived material with a pesticidally effective amount of a compound of formula (I) in claim 1.

21. A method for the treatment or prevention of a parasitic infestation or infection in or on an animal, comprising treating the animal with a parasiticidally effective amount of a compound of formula (I) in claim 1.

22. A method for controlling pests at a locus, comprising administering a pesticidally effective amount of a compound of formula (I) of claim 1, or an agriculturally acceptable salt thereof, to the locus.

* * * * *